US012582752B2

(12) United States Patent
Ueno et al.

(10) Patent No.: US 12,582,752 B2
(45) Date of Patent: Mar. 24, 2026

(54) MEDICAL DEVICE AND METHOD FOR MANUFACTURING SAME

(71) Applicant: TERUMO KABUSHIKI KAISHA, Tokyo (JP)

(72) Inventors: Yuki Ueno, Matsuda (JP); Masanori Kuramoto, Hiratsuka (JP); Hiroki Hosono, Hadano (JP); Hiromasa Kohama, Hadano (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 559 days.

(21) Appl. No.: 17/675,343

(22) Filed: Feb. 18, 2022

(65) Prior Publication Data

US 2022/0168475 A1 Jun. 2, 2022

Related U.S. Application Data

(63) Continuation of application No. PCT/JP2020/031645, filed on Aug. 21, 2020.

(30) Foreign Application Priority Data

Aug. 21, 2019 (JP) ................................ 2019-151587

(51) Int. Cl.
*A61L 29/06* (2006.01)
*A61L 31/06* (2006.01)
(Continued)

(52) U.S. Cl.
CPC ............... *A61L 29/06* (2013.01); *A61L 31/06* (2013.01); *A61L 29/085* (2013.01); *A61L 29/14* (2013.01);
(Continued)

(58) Field of Classification Search
CPC .......... A61L 29/06; A61L 31/06; A61L 31/10; A61L 29/085; C08L 77/00; C08L 71/02
See application file for complete search history.

(56) References Cited

U.S. PATENT DOCUMENTS

2007/0264503 A1 11/2007 Lai et al.
2014/0190846 A1 7/2014 Belt
(Continued)

FOREIGN PATENT DOCUMENTS

CN 103561789 A 2/2014
CN 106999636 A 8/2017
(Continued)

OTHER PUBLICATIONS

U.S. Appl. No. 17/674,891, filed Feb. 18, 2022, Masanori Kuramoto et al.
(Continued)

*Primary Examiner* — James C Yager
(74) *Attorney, Agent, or Firm* — BUCHANAN INGERSOLL & ROONEY PC

(57) ABSTRACT

A medical device that exhibits an excellent lubricating property includes: a substrate layer; and a surface lubricious layer formed on at least a part of the substrate layer, and containing a hydroxy group-containing compound selected from a group consisting of a non-volatile alcohol, a partially esterified product thereof, and a partially etherified product thereof, and soluble in water, and a hydrophilic copolymer containing a structural unit derived from a polymerizable monomer (A) having a sulfobetaine structure, a structural unit derived from a polymerizable monomer (B) having at least one group selected from a group consisting of a sulfonic acid group ($—SO_3H$), a sulfuric acid group ($—OSO_3H$), a sulfurous acid group ($—OSO_2H$), and salt
(Continued)

10 groups thereof, and a structural unit derived from a polymerizable monomer (C) having a photoreactive group.

21 Claims, 4 Drawing Sheets

(51) Int. Cl.

| | |
|---|---|
| *A61L 29/08* | (2006.01) |
| *A61L 29/14* | (2006.01) |
| *A61L 31/10* | (2006.01) |
| *A61L 31/14* | (2006.01) |

(52) U.S. Cl.
CPC ............... *A61L 31/10* (2013.01); *A61L 31/14* (2013.01); *Y10T 428/1352* (2015.01); *Y10T 428/1393* (2015.01)

(56) References Cited

U.S. PATENT DOCUMENTS

| | | | | |
|---|---|---|---|---|
| 2017/0258966 | A1 | 9/2017 | Kohama et al. | |
| 2018/0126035 | A1* | 5/2018 | O'Mahony | C10M 107/22 |
| 2019/0185776 | A1* | 6/2019 | Kuramoto | C09D 133/14 |
| 2020/0376171 | A1 | 12/2020 | Kuramoto et al. | |
| 2022/0168476 | A1 | 6/2022 | Kuramoto | |
| 2022/0168479 | A1 | 6/2022 | Kuramoto | |
| 2022/0176022 | A1 | 6/2022 | Kuramoto | |
| 2022/0177618 | A1 | 6/2022 | Kuramoto et al. | |

FOREIGN PATENT DOCUMENTS

| | | | |
|---|---|---|---|
| CN | 109384882 | A | 2/2019 |
| CN | 109641994 | A | 4/2019 |
| EP | 1 809 345 | B1 | 3/2009 |
| JP | 2001079082 | A | 3/2001 |
| JP | 2004-215710 | A | 8/2004 |
| JP | 2008515495 | A | 5/2008 |
| JP | 2009107176 | A | 5/2009 |
| JP | 2020028639 | A | 2/2020 |
| WO | 2018038063 | A1 | 3/2018 |
| WO | 2018038603 | A1 | 3/2018 |
| WO | 2019163764 | A1 | 8/2019 |

OTHER PUBLICATIONS

U.S. Appl. No. 17/675,063, filed Feb. 18, 2022, Masanori Kuramoto.
U.S. Appl. No. 17/675,334, filed Feb. 18, 2022, Masanori Kuramoto.
U.S. Appl. No. 17/675,565, filed Feb. 18, 2022, Masanori Kuramoto.
English Translations of the International Search Report (Form PCT/ISA/210) and the Written Opinion of the International Searching Authority (Form PCT/ISA/237) issued Nov. 2, 2020, by the Japanese Patent Office in corresponding International Application No. PCT/JP2020/031645. (6 pages).
Office Action (Notice of Reasons for Refusal) issued on Apr. 2, 2024, in corresponding Japanese Patent Application No. 2021-540991 and English translation of the Office Action. (7 pages).
International Search Report (PCT/ISA/210) with translation and Written Opinion (PCT/ISA/237) mailed on Nov. 2, 2020, by the Japan Patent Office as the International Searching Authority for International Application No. PCT/JP2020/031645. (9 pages).
The extended European Search Report issued Aug. 16, 2022, by the European Patent Office in corresponding European Patent Application No. 20854113.6-1109. (7 pages).
Office Action (The First Office Action) issued Aug. 10, 2022, by the State Intellectual Property Office of People's Republic of China in corresponding Chinese Patent Application No. 202080058582.2 and an English Translation of the Office Action. (23 pages).

* cited by examiner

FIG. 1
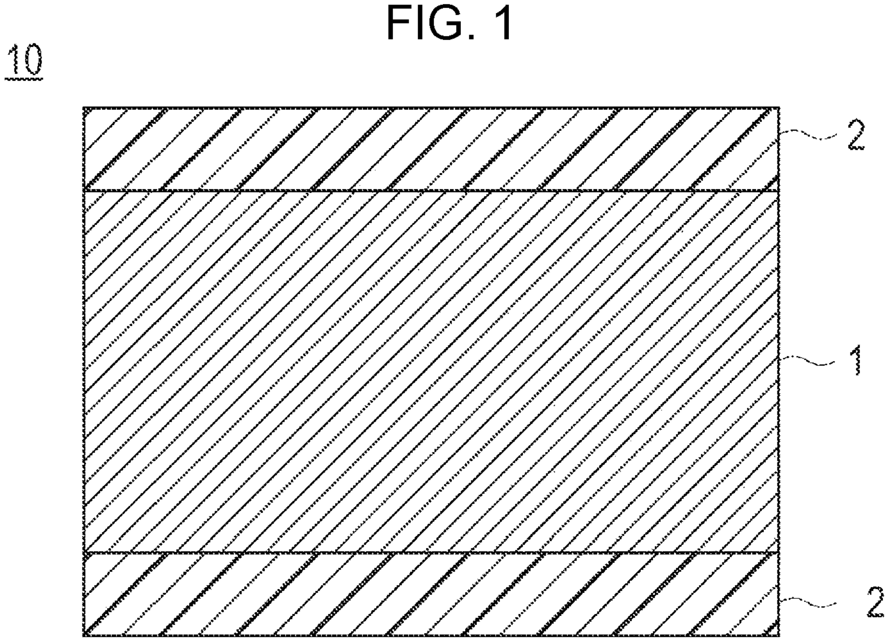
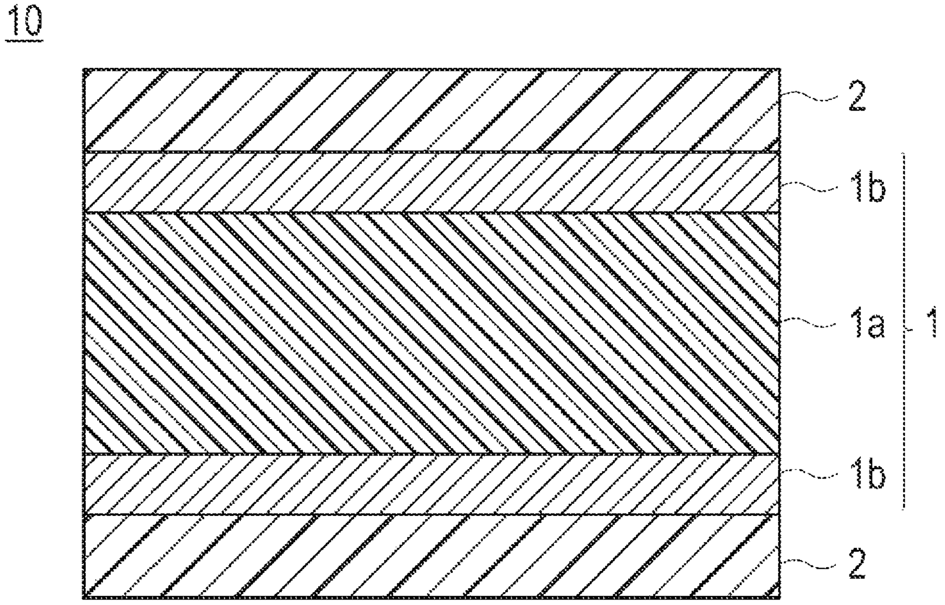
FIG. 2

FIG. 3
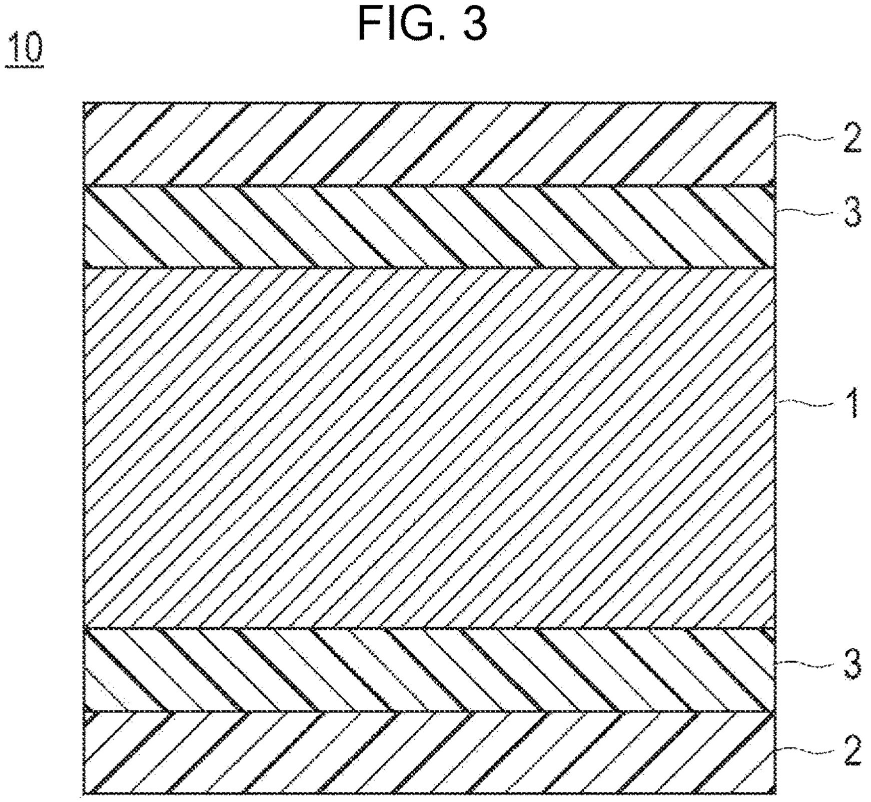
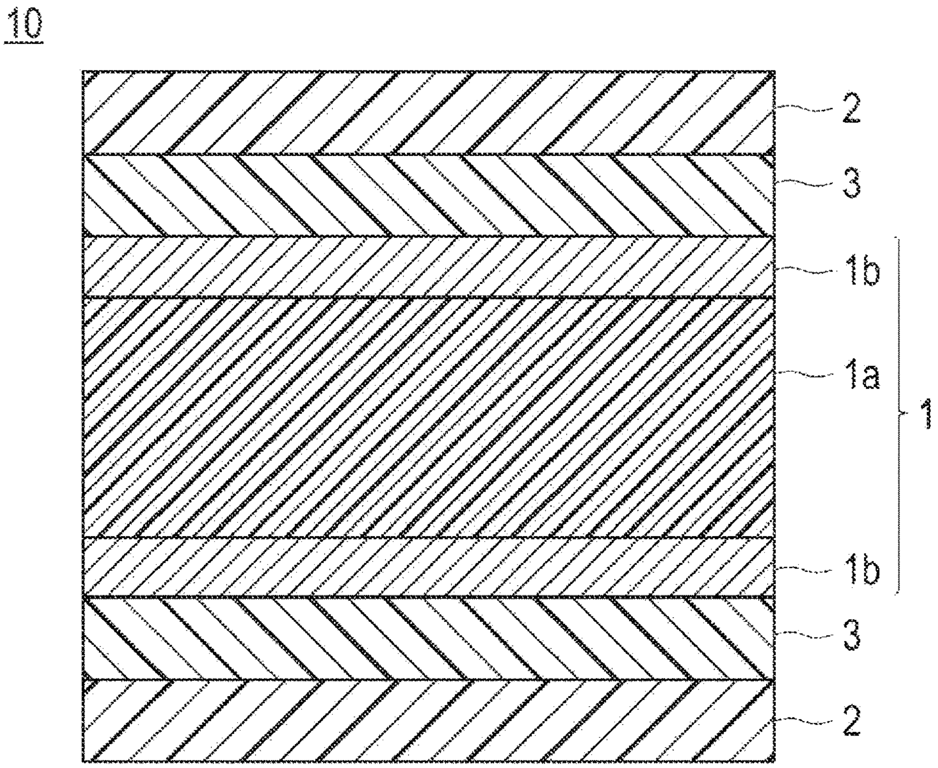
FIG. 4

FIG. 5
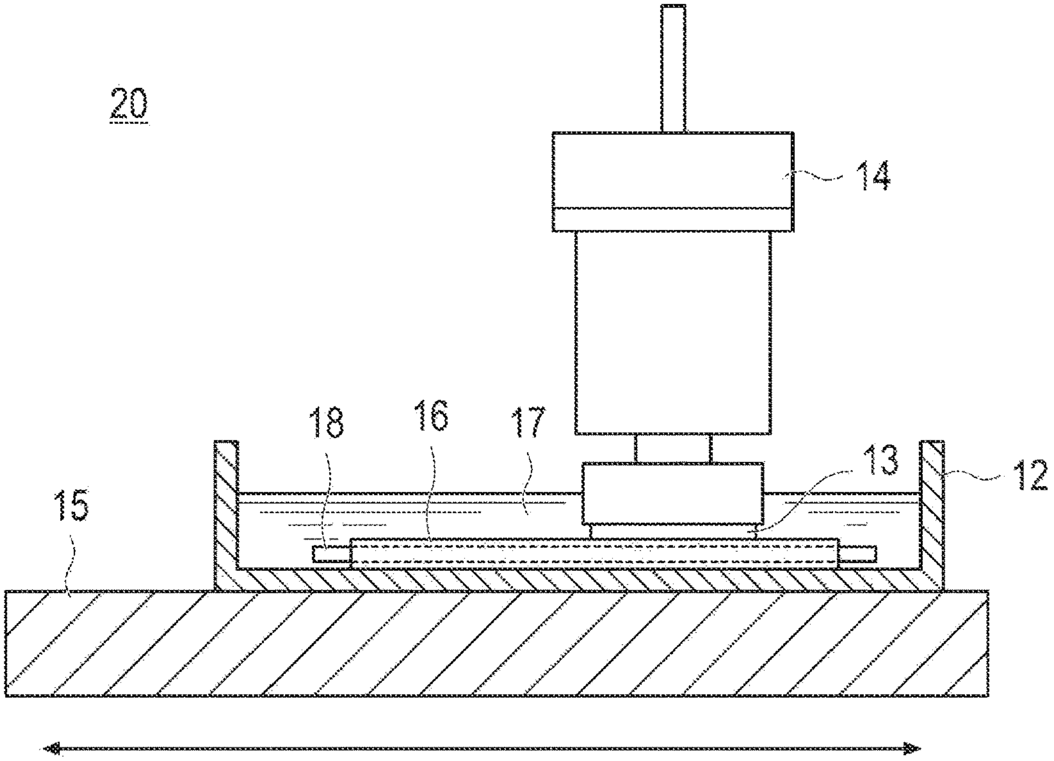
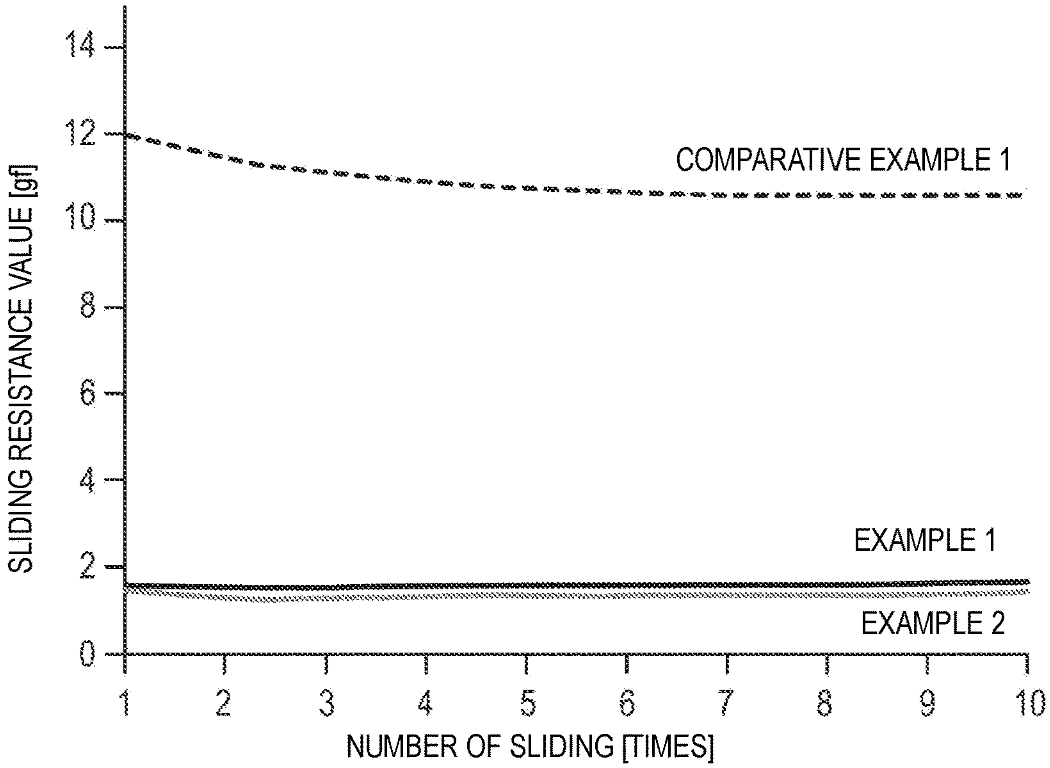
FIG. 6

MEDICAL DEVICE AND METHOD FOR MANUFACTURING SAME

CROSS-REFERENCES TO RELATED APPLICATIONS

This application is a continuation of International Patent Application No. PCT/JP2020/031645 filed on Aug. 21, 2020, which claims priority to Japanese Patent Application No. 2019-151587 filed on Aug. 21, 2019, the entire content of both of which is incorporated herein by reference.

FIELD OF THE INVENTION

The disclosure here relates to a medical device and a method for manufacturing the same. In particular, the disclosure relates to a medical device including a surface lubricious layer exhibiting an excellent lubricating property and a method for manufacturing the same.

BACKGROUND DISCUSSION

In recent years, a catheter has a reduced outer diameter to improve an insertion property thereof to a peripheral portion of a blood vessel, and is thereby used for diagnosis and treatment of various lesion sites. In the diagnosis or the treatment using the catheter, a clearance between the catheter and an inner surface of a lumen in a living body is extremely small, which may result in high frictional resistance on a surface of the catheter. Therefore, the catheter is required to include a coating that imparts a lubricating property and durability (lubrication retaining property) to the surface of the catheter.

For example, WO 2018/038063 (corresponding to US 2019/0185776 A1) discloses that a hydrophilic copolymer is used for a surface lubricious layer, the hydrophilic copolymer containing a structural unit derived from a polymerizable monomer (A) having a sulfobetaine structure, a structural unit derived from a polymerizable monomer (B) having a group such as a sulfonic acid group, and a structural unit derived from a polymerizable monomer (C) having a photoreactive group.

SUMMARY

The surface lubricious layer disclosed in WO 2018/038063 (corresponding to US 2019/0185776 A1) certainly exhibits an excellent lubricating property and excellent durability (lubrication retaining property). On the other hand, a medical technique for advancing a more flexible medical device to a narrower lesion site in a living body becomes widespread, and in recent years, a demand for operability for making the medical device reach the lesion site increases. Therefore, a technique for further improving the lubricating property in order to operate the medical device satisfactorily even in a narrower lesion site is demanded.

The disclosure here provides a way for improving the lubricating property.

The present inventors have made diligent studies to solve the above problem. As a result, the present inventors have found that the above problem can be solved by providing, on a substrate layer, a surface lubricious layer containing a hydrophilic copolymer containing specific structural units and a specific water-retaining material such as a hydroxy group-containing compound soluble in water, and have thus completed the discovery described below.

Disclosed here is a medical device including: a substrate layer; and a surface lubricious layer formed on at least a part of the substrate layer, and containing a hydroxy group-containing compound selected from the group consisting of a non-volatile alcohol, a partially esterified product thereof, and a partially etherified product thereof, and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group.

According to another aspect, a medical device including: a substrate layer; and a surface lubricious layer formed on at least a part of the substrate layer, and containing a hydroxy group-containing compound represented by the following formula and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group.

$$X—O\text{-}(A\text{-}O)_n\text{-}Y \qquad \text{[Chem. 1]}$$

In the above formula,

X represents a hydrogen atom or a substituted or unsubstituted monovalent hydrocarbon group having 1 to 22 carbon atoms, A represents a group represented by $—CH_2—$, $—(CH_2)_2—$, $—(CH_2)_3—$, or $—CH_2—CH(CH_3)—$, n represents a number of 1 or more, Y represents a hydrogen atom or an acyl group, and when Y represents an acyl group, X represents a hydrogen atom or a monovalent hydrocarbon group having 1 to 7 carbon atoms substituted with a hydroxy group.

Also disclosed is a medical device including: a substrate layer; and a surface lubricious layer formed on at least a part of the substrate layer, and containing a hydroxy group-containing compound selected from the group consisting of glycerol, a glycerol condensate, partially esterified products thereof, and partially etherified products thereof, and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group.

BRIEF DESCRIPTION OF THE DRAWINGS

FIG. 1 is a partial cross-sectional view schematically showing a surface lamination structure of a medical device according to an exemplary embodiment of the invention.

FIG. 2 is a partial cross-sectional view schematically showing a configuration example having a different surface lamination structure as a first application example of the embodiment in FIG. 1.

FIG. 3 is a partial cross-sectional view schematically showing a configuration example having a different surface lamination structure as a second application example of the embodiment in FIG. 1.

FIG. 4 is a partial cross-sectional view schematically showing a configuration example having a different surface lamination structure as a third application example of the embodiment in FIG. 1.

FIG. 5 is a schematic view showing a lubricating property and durability test device (friction meter) used in Examples and Comparative Examples.

FIG. 6 is a graph showing lubricating property and durability test results in Examples 1 and 2 and Comparative Example 1.

DETAILED DESCRIPTION

Figure 7:
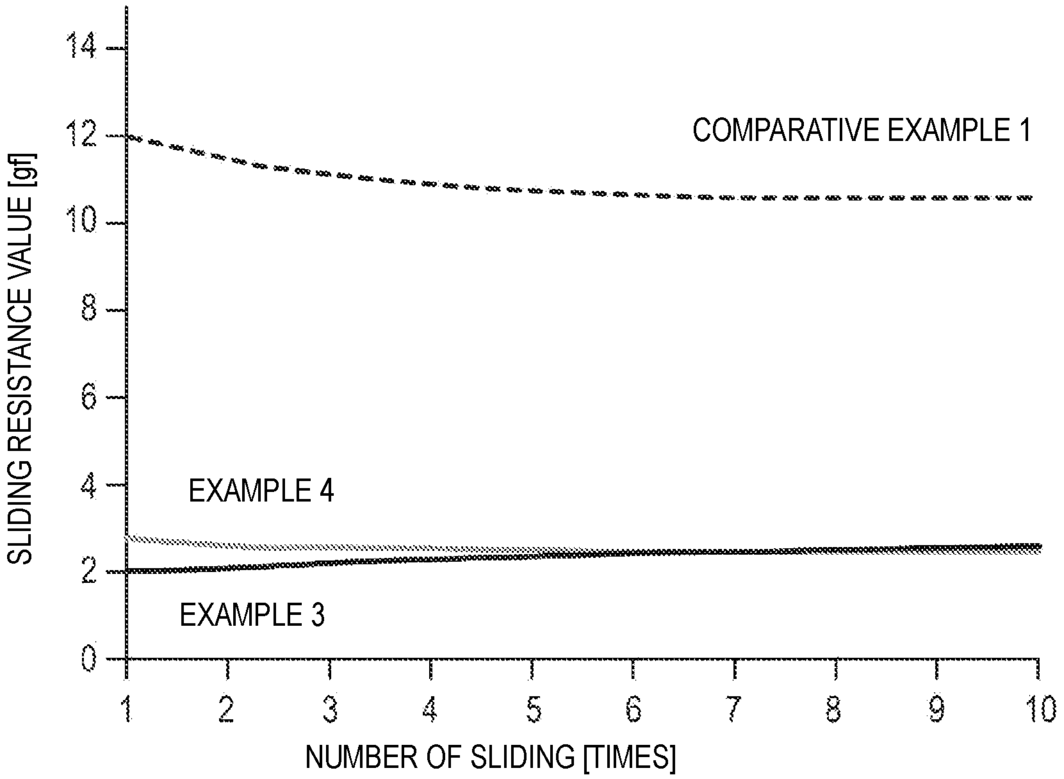
FIG. 7 is a graph showing lubricating property and durability test results in Examples 3 and 4 and Comparative Example 1.

Set forth below with reference to the accompanying drawings is a detailed description of embodiments of a medical device and a manufacturing method representing examples of the inventive medical device and a manufacturing method disclosed here. The invention is not limited to the following embodiments. In the present description, "x to y" indicating a range includes x and y, and means "x or more and y or less". In the present description, "x and/or y" means to include at least one of x and y, and includes "x alone", "y alone", and "a combination of x and y". Unless otherwise specified, operations, measurements of physical properties, and the like are performed under conditions of room temperature (20° C. to 25° C.) and a relative humidity of 40% to 60% RH.

In the present description, the term "(meth)acrylic" includes both acrylic and methacrylic. Therefore, for example, the term "(meth)acrylic acid" includes both acrylic acid and methacrylic acid. Similarly, the term "(meth) acryloyl" includes both acryloyl and methacryloyl. Therefore, for example, the term "(meth)acryloyl group" includes both an acryloyl group and a methacryloyl group.

In the present description, unless otherwise specified, the term "substituted" refers to being substituted with a C1 to C30 alkyl group, a C2 to C30 alkenyl group, a C2 to C30 alkynyl group, a C1 to C30 alkoxy group, an alkoxycarbonyl group (—COOR, R represents a C1 to C30 alkyl group), a halogen atom (F, Cl, Br, or I atom), a C6 to C30 aryl group, a C6 to C30 aryloxy group, an amino group, a C1 to C30 alkylamino group, a cyano group, a nitro group, a thiol group, a C1 to C30 alkylthio group, or a hydroxy group. Note that, when a group is substituted, a substitution in which a structure after substitution falls under a definition before the substitution is excluded. For example, when a substituent is an alkyl group, this alkyl group as a substituent is not further substituted with another alkyl group.

In the present description, a "polymerizable monomer (A) having a sulfobetaine structure" is also simply referred to as a "polymerizable monomer (A)" or a "polymerizable monomer (A) according to the invention". Similarly, a "structural unit derived from a polymerizable monomer (A) having a sulfobetaine structure" is also simply referred to as a "structural unit (A)" or a "structural unit (A) according to the invention".

In the present description, a "polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof" is also simply referred to as a "polymerizable monomer (B)" or a "polymerizable monomer (B) according to the invention". Similarly, a "structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof" is also simply referred to a "structural unit (B)" or a "structural unit (B) according to the invention".

In the present description, a "polymerizable monomer (C) having a photoreactive group" is also simply referred to as a "polymerizable monomer (C)" or a "polymerizable monomer (C) according to the invention". Similarly, a "structural unit derived from a polymerizable monomer (C) having a photoreactive group" is also simply referred to as a "structural unit (C)" or a "structural unit (C) according to the invention".

In the present description, a "hydrophilic copolymer containing a structural unit (A), a structural unit (B), and a structural unit (C)" is also simply referred to as a "hydrophilic copolymer" or a "hydrophilic copolymer according to the invention".

In the present description, a "polymerizable monomer" is also simply referred to as a "monomer".

In the present description, the term "soluble in water" refers to being dissolved by an amount of 0.001 g or more in 100 mL of distilled water under a condition of room temperature (23° C.). Note that an upper limit is not particularly limited, and is, for example, 100 g or less.

In the present description, when a structural unit is said to be "derived" from a monomer, it means that the structural unit is a divalent structural unit generated by a polymerizable unsaturated double bond (C═C) present in the monomer corresponding to the structural unit becoming a single bond (—C—C—).

According to a first aspect of the disclosure, a medical device is provided, the medical device including: a substrate layer; and a surface lubricious layer formed on at least a part of the substrate layer, and containing a hydroxy group-containing compound (hereinafter, also referred to as a "hydroxy group-containing compound (1)") selected from the group consisting of a non-volatile alcohol, a partially esterified product thereof (a partially esterified product of a non-volatile alcohol), and a partially etherified product thereof (a partially etherified product of a non-volatile alcohol), and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group.

According to a second aspect, a medical device is provided, the medical device including: a substrate layer; and a surface lubricious layer formed on at least a part of the substrate layer, and containing a hydroxy group-containing compound (hereinafter, also referred to as a "hydroxy group-containing compound (2)") represented by the following formula and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group.

$$X—O—(A-O)_n—Y \quad \text{[Chem. 2]}$$

In the above formula,

X represents a hydrogen atom or a substituted or unsubstituted monovalent hydrocarbon group having 1 to 22 carbon atoms, A represents a group represented by $—CH_2—$, $—(CH_2)_2—$, $—(CH_2)_3—$, or $—CH_2—CH(CH_3)—$, n represents a number of 1 or more, Y represents a hydrogen atom or an acyl group, and when Y represents an acyl group, X represents a hydrogen atom or a monovalent hydrocarbon group having 1 to 7 carbon atoms substituted with a hydroxy group.

According to a third aspect of the disclosure, a medical device is provided, the medical device including: a substrate layer; and a surface lubricious layer formed on at least a part of the substrate layer, and containing a hydroxy group-containing compound (hereinafter, also referred to as a "hydroxy group-containing compound (3)") selected from the group consisting of glycerol, a glycerol condensate, partially esterified products thereof (a partially esterified product of glycerol and a partially esterified product of the glycerol condensate), and partially etherified products thereof (a partially etherified product of glycerol and a partially etherified product of the glycerol condensate), and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group.

The medical device having a configuration according to the above first, second, or third aspect can exhibit an excellent lubricating property.

In recent years, miniaturization and diameter reduction of medical devices are advanced, and a medical technique for advancing a more flexible medical device to a narrower lesion site in a living body becomes widespread. A device that can maintain good operability even in a site where a clearance between the medical device and an inner surface of a lumen in the living body is small is demanded. The present inventors have made diligent studies to meet such a demand. As a result, the present inventors have found that a high lubricating property can be exhibited even under a high load condition (that is, even in a site where the clearance between the medical device and the inner surface of the lumen in the living body is small) by providing, on the substrate layer, a surface lubricious layer containing the above hydrophilic copolymer and a specific water-retaining material (the above hydroxy group-containing compound (1), (2), or (3)). A mechanism by which such an effect is produced is unclear, but the following mechanism is theorized. Note that the following mechanism is theory, and the invention is not limited to the following theory. Specifically, the hydrophilic copolymer contained in the surface lubricious layer exhibits a lubricating property when wet (for example, when in contact with an aqueous liquid such as a body fluid or physiological saline). The surface lubricious layer contains the water-retaining material (in the first aspect, the hydroxy group-containing compound (1); in the second aspect, the hydroxy group-containing compound (2); in the third aspect, the hydroxy group-containing compound (3); the same applies hereinafter) in addition to the hydrophilic copolymer. In such a surface lubricious layer, in addition to a water absorption effect of the water-retaining material, a crosslink density is moderately low due to the presence of the water-retaining material. Therefore, the aqueous liquid easily enters the surface lubricious layer (the hydrophilic copolymer easily exhibits a lubricating property (surface gel hydration lubrication) when in contact with the aqueous liquid). Under a high load condition, the surface lubricious layer according to the disclosure can maintain a sufficient hydrated layer on a surface of the medical device by the aqueous liquid retained by the surface lubricious layer. Therefore, it is considered that the hydrophilic copolymer can exhibit a sufficient lubricating property even under a high load condition.

The hydrophilic copolymer contained in the surface lubricious layer has a photoreactive group. When the surface lubricious layer is irradiated with active energy rays, the photoreactive group generates reactive species, and the hydrophilic copolymer in the surface lubricious layer reacts with a material constituting a layer adjacent to the surface lubricious layer (for example, the substrate layer) to form a covalent bond between the surface lubricious layer and the layer adjacent to the surface lubricious layer. In addition, the hydrophilic copolymer in the surface lubricious layer reacts with the water-retaining material in the surface lubricious layer, so as to firmly immobilize the water-retaining material in the surface lubricious layer. Therefore, the medical device disclosed here can maintain an initial lubricating property for a longer period of time and have further improved durability (lubrication retaining property).

Therefore, the medical device can exhibit an excellent lubricating property even under a condition where the clearance between the medical device and the inner surface of the lumen in the living body is small (high load condition). In addition, the disclosed medical device can exhibit excellent durability (lubrication retaining property).

In the medical device disclosed here, the surface lubricious layer contains the hydrophilic copolymer and the water-retaining material (the above hydroxy group-containing compound (1), (2), or (3)), but as described above, a form in which the hydrophilic copolymer and the water-retaining material are bonded to each other in the surface lubricious layer is included. That is, in the description of the application, the expression "the surface lubricious layer contains the hydroxy group-containing compound and the hydrophilic copolymer" is inclusive of not only a form in which the hydrophilic copolymer and the hydroxy group-containing compound are present independently in the surface lubricious layer, but also a form in which the hydrophilic copolymer and the hydroxy group-containing compound are present in the surface lubricious layer in a manner bonded to each other.

Hereinafter, a preferred embodiment of the medical device disclosed here will be described with reference to the attached drawings.

FIG. 1 is a partial cross-sectional view schematically showing a surface lamination structure of a medical device according to an exemplary embodiment (hereinafter, also simply referred to as a "medical device"). FIG. 2 is a partial cross-sectional view schematically showing a configuration example having a different surface lamination structure as an application example in the present embodiment. Note that in FIGS. 1 and 2, 1 represents a substrate layer, 1$a$ represents a substrate layer core portion, 1$b$ represents a substrate surface layer, 2 represents a surface lubricious layer, and 10 represents a medical device.

As shown in FIGS. 1 and 2, the medical device 10 according to the present embodiment includes: the substrate layer 1; and the surface lubricious layer 2 containing a hydrophilic copolymer and a water-retaining material, and immobilized (disposed) so as to cover at least a part of a surface of the substrate layer 1 (the drawings show an example of being immobilized (disposed) on the whole surface (entire surface) of the substrate layer 1 in the drawings). The surface lubricious layer 2 is bonded to the substrate layer 1 via the photoreactive group of the hydrophilic copolymer.

FIG. 3 is a partial cross-sectional view schematically showing a surface lamination structure of a medical device according to another exemplary embodiment (hereinafter, also simply referred to as a "medical device")

FIG. 3 is a partial cross-sectional view schematically showing a configuration example having a different surface lamination structure as an application example in the present embodiment. Note that in FIGS. 3 and 4, 1 represents a substrate layer, 1*a* represents a substrate layer core portion, 1*b* represents a substrate surface layer, 3 represents an adhesive layer, 2 represents a surface lubricious layer, and 10 represents a medical device.

As shown in FIGS. 3 and 4, the medical device 10 according to the present embodiment includes: the substrate layer 1; the adhesive layer 3 containing the hydrophilic copolymer (1), and immobilized (disposed) so as to cover at least a part of a surface of the substrate layer 1 (the drawings show an example of being immobilized (disposed) on the whole surface (entire surface) of the substrate layer 1 in the drawings); and the surface lubricious layer 2 containing the hydrophilic copolymer (2) and a water-retaining material (in the first aspect, the hydroxy group-containing compound (1); in the second aspect, the hydroxy group-containing compound (2); and in the third aspect, the hydroxy group-containing compound (3)), and immobilized (disposed) so as to cover at least a part of a surface of the adhesive layer 3 (the drawings show an example of being immobilized (disposed) on the whole surface (entire surface) of the adhesive layer 3 in the drawings). The adhesive layer 3 is bonded to the substrate layer 1, and the hydrophilic copolymer (2) and the water-retaining material in the surface lubricious layer 2 via the photoreactive group of the hydrophilic copolymer (1). Note that, in the present description, the hydrophilic copolymer contained in the adhesive layer in the present embodiment is also referred to as the "hydrophilic copolymer (1)", and the hydrophilic copolymer contained in the surface lubricious layer is also referred to as the "hydrophilic copolymer (2)".

Hereinafter, each configuration of the medical device according to the present embodiment will be described.

<First Aspect>

The first aspect relates to a medical device including: a substrate layer; and a surface lubricious layer formed on at least a part of the substrate layer, and containing a hydroxy group-containing compound (hydroxy group-containing compound (1)) selected from the group consisting of a non-volatile alcohol, a partially esterified product thereof, and a partially etherified product thereof, and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($-SO_3H$), a sulfuric acid group ($-OSO_3H$), a sulfurous acid group ($-OSO_2H$), and salt groups thereof, and a structural unit derived from a polymerizable monomer (C) having a photoreactive group.

[Substrate Layer (Substrate)]

The substrate layer used in this aspect may be constituted by any material as long as the material can react with the photoreactive group contained in the hydrophilic copolymer, which will be described later, to form a chemical bond. Specifically, examples of the material constituting (forming) the substrate layer 1 include a metal material, a polymer material, and ceramics. Here, as shown in FIGS. 1 and 3, the substrate layer 1 may be entirely (wholly) constituted (formed) by any one of the above materials, or, as shown in FIGS. 2 and 4, the substrate layer 1 may have a configuration in which a surface of the substrate layer core portion 1*a* constituted (formed) by any one of the above materials is covered (coated) with any other of the above materials by an appropriate method to constitute (form) the substrate surface layer 1*b*. Examples of the latter case include a configuration in which a metal material is covered (coated) by an appropriate method (a known method in the related art such as plating, metal deposition, and sputtering) on the surface of the substrate layer core portion 1*a* formed by a resin material or the like to form the substrate surface layer 1*b*, and a configuration in which, on the surface of the substrate layer core portion 1*a* formed by a hard reinforcing material such as a metal material or a ceramic material, a polymer material that is more flexible than the reinforcing material such as a metal material is covered (coated) by an appropriate method (a known method in the related art such as dipping, spraying, coating, and printing), or the reinforcing material of the substrate layer core portion 1*a* and the polymer material of the substrate surface layer 1*b* are composited (an appropriate reaction treatment), so as to form the substrate surface layer 1*b*. Therefore, the substrate layer core portion 1*a* may be a multilayer structure in which different materials are laminated in multiple layers, a structure (composite) in which members made of different materials for each part of the medical device are connected to each other, or the like. Another middle layer (not shown) may be formed between the substrate layer core portion 1*a* and the substrate surface layer 1*b*. The substrate surface layer 1*b* may also be a multilayer structure in which different materials are laminated in multiple layers, a structure (composite) in which members made of different materials for each part of the medical device are connected to each other, or the like.

Among the materials constituting (forming) the substrate layer 1, the metal material is not particularly limited, and metal materials commonly used in medical devices such as a catheter, a stent, and a guide wire are used. Specific examples thereof include various stainless steels (SUS) such as SUS304, SUS316, SUS316L, SUS420J2, and SUS630, gold, platinum, silver, copper, nickel, cobalt, titanium, iron, aluminum, tin, and various alloys such as a nickel-titanium (Ni—Ti) alloy, a nickel-cobalt (Ni—Co) alloy, a cobalt-chromium (Co—Cr) alloy, and a zinc-tungsten (Zn—W) alloy. These metal materials may be used alone or in combination of two or more types thereof. The most suitable metal material as a substrate layer for a catheter, a stent, a guide wire, or the like, which is the intended use, may be appropriately selected for the above metal materials.

Among the materials constituting (forming) the above substrate layer 1, the polymer material is not particularly limited, and polymer materials commonly used in medical devices such as a catheter, a stent, and a guide wire are used. Specific examples thereof include polyamide resins, polyethylenes such as a linear low density polyethylene (LLDPE), a low density polyethylene (LDPE), a high density polyethylene (HDPE), and a modified polyethylene, polyolefin resins such as polypropylene, polyester resins such as polyethylene terephthalate, polystyrene resins such as polystyrene, cyclic polyolefin resins, modified polyolefin resins, epoxy resins, urethane resins, diallyl phthalate resins (allyl resin), polycarbonate resins, fluororesin, amino resins (a urea resin, a melamine resin, and a benzoguanamine resin), acrylic resins, polyacetal resins, vinyl acetate resins, phenol resins, vinyl chloride resins, silicone resins (silicon resins), polyether resins such as polyetheretherketone (PEEK), and polyimide resins.

These polymer materials may be used alone or in combination of two or more types thereof. The most suitable polymer material as a substrate layer for a catheter, a stent, a guide wire, or the like, which is the intended use, may be appropriately selected for the above polymer materials.

A shape of the above substrate layer is not particularly limited, and is appropriately selected as a sheet shape, a linear (wire) shape, a tubular shape, and the like depending on the form of the substrate layer to be used.

[Surface Lubricious Layer]

The surface lubricious layer is formed on at least a part of the substrate layer, and contains (i) a hydroxy group-containing compound (hydroxy group-containing compound (1)) selected from the group consisting of a non-volatile alcohol, a partially esterified product thereof, and a partially etherified product thereof, and soluble in water, and (ii) a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group. Here, the surface lubricious layer is not necessarily formed on the entire surface of the substrate layer. The surface lubricious layer may be formed on a surface portion (a part) of the substrate layer to be in contact with a body fluid.

The surface lubricious layer contains the hydroxy group-containing compound (1) and the hydrophilic copolymer. Of these, the hydrophilic copolymer exhibits a lubricating property when wet (for example, when in contact with an aqueous liquid such as a body fluid or physiological saline). On the other hand, the hydroxy group-containing compound (1) acts to retain the aqueous liquid. The presence of the hydroxy group-containing compound (1) moderately reduces the crosslink density of the surface lubricious layer. Therefore, the aqueous liquid easily enters the surface lubricious layer, and the hydrophilic copolymer easily exhibits a lubricating property (gel hydration lubrication). In addition, under a high load condition, the surface lubricious layer forms a hydrated layer between the inner surface of the lumen in the living body and the medical device due to the aqueous liquid retained on the surface lubricious layer. Therefore, it is considered that the hydrophilic copolymer can exhibit a lubricating property by being in contact with a sufficient amount of the aqueous liquid even under a high load condition. Note that the above mechanism is theory, and the invention is not limited to the above theory.

In this aspect, the surface lubricious layer may be directly disposed above the substrate layer.

Alternatively, another layer (for example, an adhesive layer) may be provided between the surface lubricious layer and the substrate layer as long as the layer does not influence functions and effects of the medical device. Note that a preferred embodiment in a case where an adhesive layer is provided between the surface lubricious layer and the substrate layer will be described in the following <First Aspect (Embodiment Including Adhesive Layer)>.

In addition, another layer may be provided on the surface lubricious layer as long as the functions and effects of the medical device are not influenced, and it is preferable that another layer is not disposed on the surface lubricious layer (the surface lubricious layer is an outermost layer). According to this embodiment, the effect (lubricating property) of the medical device can be effectively exhibited.

A thickness of the surface lubricious layer is not particularly limited. From the viewpoints of the lubricating property, the durability (lubrication retaining property), the adhesiveness to an adjacent layer (for example, the substrate layer), and the like, the thickness (dry film thickness) of the surface lubricious layer is preferably 0.01 m to 100 m, and more preferably 0.1 m to 50 m.

Hereinafter, compositions (the hydroxy group-containing compound (1), the hydrophilic copolymer, and the like) contained in the surface lubricious layer according to this aspect will be described.

(Hydroxy Group-Containing Compound (1))

The hydroxy group-containing compound (1) contained in the surface lubricious layer is a hydroxy group-containing compound that is selected from the group consisting of a non-volatile alcohol, a partially esterified product thereof, and a partially etherified product thereof, and is soluble in water. That is, the hydroxy group-containing compound (1) is a hydroxy group-containing compound that is selected from the group consisting of a non-volatile alcohol, a partially esterified product of the non-volatile alcohol, and a partially etherified product of the non-volatile alcohol, and is soluble in water. Here, the term "non-volatile" means having a low vapor pressure at normal temperature (23° C.), and specifically means having a boiling point at normal pressure (1 atm=101.325 kPa) of 130° C. or higher. The term "alcohol" refers to a compound obtained by substituting at least one hydrogen atom with a hydroxy group in an aliphatic hydrocarbon in which a part of methylene groups ($—CH_2—$) may be substituted with an ether group (—O—). The aliphatic hydrocarbon may be linear or branched, and is not particularly limited. Examples thereof include saturated aliphatic hydrocarbons such as ethane, propane, butane, pentane, and hexane, and unsaturated aliphatic hydrocarbons such as butene, pentene, and hexene.

Note that in the present description, unless otherwise specified, the "boiling point" means a boiling point at normal pressure (1 atm=101.325 kPa).

The partially esterified product of the non-volatile alcohol refers to a compound obtained by substituting a part of hydroxy groups (—OH) in a non-volatile alcohol having a plurality of hydroxy groups with —OC(═O)R (wherein R represents a monovalent hydrocarbon group) or $—OS(═O)_2R$ (wherein R represents a monovalent hydrocarbon group). That is, the partially esterified product of the non-volatile alcohol has at least one hydroxy group.

The partially etherified product of the non-volatile alcohol refers to a compound obtained by substituting a part of hydroxy groups (—OH) in a non-volatile alcohol having a plurality of hydroxy groups with —OR (wherein R represents a monovalent hydrocarbon group). That is, the partially etherified product of the non-volatile alcohol has at least one hydroxy group.

The above monovalent hydrocarbon group is not particularly limited, and examples thereof include an alkyl group having 1 to 24 carbon atoms, an alkenyl group having 2 to 24 carbon atoms, a cycloalkyl group having 3 to 9 carbon atoms, and an aryl group having 6 to 30 carbon atoms.

The alkyl group having 1 to 24 carbon atoms may be linear or branched, and examples thereof include a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, a neopentyl group, a 1,2-dimethylpropyl group, an n-hexyl group, an isohexyl group, a 1,3-dimethylbutyl group, a 1-isopropylpropyl group, a 1,2-dimethylbutyl group, an n-heptyl group, a 1,4-dimethylpentyl group, a 3-ethylpentyl group, a 2-methyl-1-isopropylpropyl group, a 1-ethyl-3-methylbutyl group, an n-octyl group, a 2-ethylhexyl group, a 3-methyl-1-isopropylbutyl group, a 2-methyl-1-isopropyl group, a 1-t-butyl-2-methylpropyl group, an n-nonyl group, a 3,5,5-trimethylhexyl group, an n-decyl group, an isodecyl group, an n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, and an n-tetracosyl group.

The alkenyl group having 2 to 24 carbon atoms may be linear or branched, and examples thereof include a vinyl group, a 1-propenyl group, a 2-propenyl group (allyl group), an isopropenyl group, a 1-butenyl group, a 2-butenyl group, a 3-butenyl group, a 1-pentenyl group, a 2-pentenyl group, a 3-pentenyl group, a 1-hexenyl group, a 2-hexenyl group, a 3-hexenyl group, a 1-heptenyl group, a 2-heptenyl group, a 5-heptenyl group, a 1-octenyl group, a 3-octenyl group, a 5-octenyl group, a dodecenyl group, and an octadecenyl group.

The cycloalkyl group having 3 to 9 carbon atoms is not particularly limited, and examples thereof include a cyclopropyl group, a cyclobutyl group, a cyclopentyl group, a cyclohexyl group, a cycloheptyl group, and a cyclooctyl group.

Examples of the aryl group having 6 to 30 carbon atoms include a phenyl group, a biphenyl group, a terphenyl group, a pentarenyl group, an indenyl group, a naphthyl group, an azulenyl group, a heptalenyl group, a biphenylenyl group, a fluorenyl group, an acenaphthylenyl group, a pleiadenyl group, an acenaphthenyl group, a phenalenyl group, a phenanthryl group, an anthryl group, a fluoranthenyl group, an acephenanthrylenyl group, an aceanthrylenyl group, a triphenylenyl group, a pyrenyl group, a chrysenyl group, and a naphthacenyl group.

The hydroxy group-containing compound (1) is a hydroxy group-containing compound soluble in water, among the non-volatile alcohol, the partially esterified product thereof, and the partially etherified product thereof. That is, the hydroxy group-containing compound (1) is a hydroxy group-containing compound that is dissolved by an amount of 0.001 g or more in 100 mL of distilled water under a condition of room temperature (23° C.), among the non-volatile alcohol, the partially esterified product thereof, and the partially etherified product thereof.

An upper limit of a molecular weight of the hydroxy group-containing compound (1) is not particularly limited, and is preferably 10,000 or less, more preferably 5,000 or less, still more preferably 2,000 or less, even more preferably 1,000 or less, and particularly preferably 500 or less. A lower limit of the molecular weight of the hydroxy group-containing compound (1) is not particularly limited, and is, for example, 50 or more. Note that when a structure of the hydroxy group-containing compound (1) is specified, the molecular weight of the compound is a molecular weight calculated based on the structure. Alternatively, when the structure of the compound is not specified, the molecular weight is a weight average molecular weight (Mw) measured in terms of polyethylene glycol by gel permeation chromatography (GPC).

Examples of the non-volatile alcohol, the partially esterified product thereof, and the partially etherified product thereof include ethylene glycol (boiling point: 198° C.), polyethylene glycol, propylene glycol (boiling point: 188° C.), polypropylene glycol, glycerol (boiling point: 290° C.), a glycerol condensate, dipropylene glycol (boiling point: 232° C.), tripropylene glycol (boiling point: 270° C.), polyvinyl alcohol, glycerol 1,2-carbonate (boiling point: 160° C.), trehalose (boiling point: 398° C.), erythritol (boiling point: 331° C.), partially esterified products thereof, and partially etherified products thereof. These materials may be used alone or in combination of two or more types thereof. Note that the glycerol condensate is a compound described in (Hydroxy Group-Containing Compound (3)) in the following <Third Aspect>, and examples thereof include diglycerol (glycerol dimer, boiling point: 270° C.), triglycerol (glycerol trimer, boiling point: 271° C.), and polyglycerin.

That is, in a preferred embodiment of this aspect, the hydroxy group-containing compound (1) is a hydroxy group-containing compound that is selected from the group consisting of ethylene glycol, polyethylene glycol, propylene glycol, polypropylene glycol, glycerol, a glycerol condensate, dipropylene glycol, tripropylene glycol, polyvinyl alcohol, glycerol 1,2-carbonate, trehalose, erythritol, partially esterified products thereof, and partially etherified products thereof, and is soluble in water. In a more preferred embodiment of this aspect, the hydroxy group-containing compound (1) is a hydroxy group-containing compound that is selected from the group consisting of ethylene glycol, polyethylene glycol, propylene glycol, polypropylene glycol, glycerol, a glycerol condensate, dipropylene glycol, tripropylene glycol, polyvinyl alcohol, partially esterified products thereof, and partially etherified products thereof, and is soluble in water.

From the viewpoint of further improving the lubricating property and the durability (lubrication retaining property), the hydroxy group-containing compound (1) is preferably a compound having two or more hydroxy groups (—OH), and more preferably a compound having 2 to 8 hydroxy groups (—OH). Alternatively, from the viewpoint of further improving the lubricating property and the durability (lubrication retaining property), the hydroxy group-containing compound (1) is preferably a compound having 2 or 3 carbon atoms between oxygen atoms. From the above viewpoint, the hydroxy group-containing compound (1) is more preferably at least one hydroxy group-containing compound that is selected from the group consisting of ethylene glycol, polyethylene glycol, propylene glycol, polypropylene glycol, glycerol, diglycerol, triglycerol, dipropylene glycol, tripropylene glycol, polyvinyl alcohol, trehalose, and erythritol, and is soluble in water, and particularly preferably polyethylene glycol, glycerol, diglycerol, tripropylene glycol, trehalose, or erythritol.

As the hydroxy group-containing compound (1), either a synthetic product or a commercially available product may be used. The commercially available product is available from Sigma-Aldrich Co. LLC., Tokyo Chemical Industry Co., Ltd., FUJIFILM Wako Pure Chemical Corporation, and the like.

(Hydrophilic Copolymer)

The surface lubricious layer contains a hydrophilic copolymer in addition to the hydroxy group-containing compound (1). The hydrophilic copolymer contains a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group.

In the surface lubricious layer, an abundance ratio (mixing ratio) of the hydroxy group-containing compound (1) with respect to the hydrophilic copolymer is not particularly limited. In the surface lubricious layer, for the abundance ratio (mixing ratio) of the hydroxy group-containing compound (1) with respect to the hydrophilic copolymer, the hydrophilic copolymer is preferably 0.1 parts by weight or more, more preferably 0.5 parts by weight or more, still more preferably 1 part by weight or more, and particularly preferably 2 parts by weight or more, with respect to 1 part by weight of the hydroxy group-containing compound (1). In the surface lubricious layer, for the abundance ratio (mixing ratio) of the hydroxy group-containing compound (1) with respect to the hydrophilic copolymer, the hydrophilic copolymer is preferably 1,000 parts by weight or less, more preferably 100 parts by weight or less, still more preferably 50 parts by weight or less, and particularly preferably 20 parts by weight or less, with respect to 1 part by weight of the hydroxy group-containing compound (1). With such an abundance ratio (mixing ratio), the water retention effect of the hydroxy group-containing compound (1) and the lubricating property of the hydrophilic copolymer can be exhibited in a good balance. Note that when the surface lubricious layer contains two or more types of the hydroxy group-containing compounds (1), the above "1 part by weight" means that a total amount of these hydroxy group-containing compounds (1) is 1 part by weight. Similarly, when the surface lubricious layer contains two or more types of hydrophilic copolymers, the above amount (part by weight) of the hydrophilic copolymers means a total amount of these hydrophilic copolymers. The above abundance ratio (mixing ratio) is substantially equal to a ratio of a total charge amount (weight) of the hydrophilic copolymers with respect to a total charge amount (weight) of the hydroxy group-containing compounds (1) during formation of the surface lubricious layer.

Here, the presence and the ratio (composition) of the structural unit derived from each polymerizable monomer in the hydrophilic copolymer and the presence of the hydroxy group-containing compound (1) in the surface lubricious layer can be confirmed by, for example, analyzing a peak intensity of a group contained in each structural unit using a known means such as IR, NMR, and mass spectrometry. In the present description, the presence and the ratio of the structural unit derived from each polymerizable monomer in the hydrophilic copolymer in the surface lubricious layer are measured according to the following method.

(Method for Detecting and Measuring Presence and Ratio of Structural Unit Derived from Each Polymerizable Monomer in Hydrophilic Copolymer in Surface Lubricious Layer)

With the surface of the medical device swollen with heavy water or the like, precision diagonal cutting is performed on the medical device to prepare an inclined cross section of the medical device.

From the cross section, (i) a surface lubricious layer portion located on a surface of the substrate of the medical device is cut in a case where no other layers are provided between the substrate layer and the surface lubricious layer, or (ii) a surface lubricious layer portion located near the surface of the medical device is cut in a case where another layer (for example, an adhesive layer) is provided between the substrate layer and the surface lubricious layer, and a material of the surface lubricious layer portion is collected. Next, the material of the surface lubricious layer portion is filled into a sample tube for solid NMR without any gap to prepare a sample, and $^1$H-NMR or $^{13}$C-NMR measurement is performed. Here, peaks specific to a site (for example, a sulfobetaine structure) specific to the structural unit (A), a site (for example, a salt of a sulfonic acid group) specific to the structural unit (B), and a site (for example, a benzophenone group) specific to the structural unit (C) are to be confirmed, and when these peaks are confirmed, it is determined that the corresponding structural units are present in the sample. A concentration of the site (for example, the sulfobetaine structure) specific to the structural unit (A) (concentration (a)), a concentration of the site (for example, the salt of the sulfonic acid group) specific to the structural unit (B) (concentration (b)), and a concentration of the site (for example, the benzophenone group) specific to the structural unit (C) (concentration (c)) are measured. A ratio of each of the concentrations (a), (b), and (c) is regarded as an abundance ratio of the structural unit derived from each polymerizable monomer in the hydrophilic copolymer. Note that an analyzer and measurement conditions used in the above measurement are as follows.

Analyzer: ECZ500R, NM080006, manufactured by JEOL Ltd.

Measurement conditions: heavy water or a mixed liquid of heavy water and a heavy solvent of a lower alcohol.

The presence of the hydroxy group-containing compound (1) in the surface lubricious layer can be confirmed by preparing a sample of the material of the surface lubricious layer portion and performing $^1$H-NMR and $^{13}$C-NMR measurement in the same manner as in the above (Method for Detecting and Measuring Presence and Ratio of Structural Unit Derived from Each Polymerizable Monomer in Hydrophilic Copolymer in Surface Lubricious Layer). Here, a peak specific to a site (for example, carbon atoms and protons of a hydrocarbon group bonded to a hydroxy group) specific to the hydroxy group-containing compound (1) is to be confirmed, and when the peak is confirmed, it is determined that the hydroxy group-containing compound (1) is present in the sample. Note that an analyzer and measurement conditions used in the above measurement are as follows.

Analyzer: ECZ500R, NM080006, manufactured by JEOL Ltd.

Measurement conditions: heavy water or a mixed liquid of heavy water and a heavy solvent of a lower alcohol.

The abundance ratio (mixing ratio) of the hydroxy group-containing compound (1) with respect to the hydrophilic copolymer in the surface lubricious layer can also be measured using the same known means as described above. In the present description, the abundance ratio (mixing ratio) of the hydroxy group-containing compound (1) with respect to the hydrophilic copolymer in the surface lubricious layer is measured according to the following method.

(Method for Measuring Abundance Ratio (Mixing Ratio) of Hydroxy Group-Containing Compound (1) with Respect to Hydrophilic Copolymer in Surface Lubricious Layer)

Precision diagonal cutting is performed on the medical device to prepare an inclined cross section of the medical device. From the cross section, a surface lubricious layer portion located near the surface of the medical device is cut, and a material of the surface lubricious layer portion is collected. Next, the material of the surface lubricious layer portion is placed in a pyrolysis GC/MS furnace to be decomposed, and a degradation product thereof is subjected to GC/MS measurement. A value obtained by calculating a ratio of a chromatogram peak derived from a decomposition product of the hydroxy group-containing compound (1) (for example, paraffin or ethers) with respect to a chromatogram peak derived from a decomposition product of the hydrophilic copolymer (for example, benzophenone or an amine compound) is the abundance ratio (mixing ratio) of the hydroxy group-containing compound (1) with respect to the hydrophilic copolymer in the surface lubricious layer. Note that an analyzer and measurement conditions used in the above measurement are as follows.

Analyzer: TMS-Q1000GC, RY2020D, manufactured by JEOL Ltd.

Measurement conditions: decomposition temperature: 600° C.

Hereinafter, each polymerizable monomer constituting the hydrophilic copolymer contained in the surface lubricious layer will be described.

(Polymerizable Monomer (A))

The hydrophilic copolymer contains the structural unit derived from the polymerizable monomer (A) having a sulfobetaine structure (structural unit (A)). Here, the structural unit (A) constituting the hydrophilic copolymer may be one type alone or a combination of two or more types. That is, the structural unit (A) may be constituted by only one type of structural unit (A), or may be constituted by two or more types of structural units (A). Note that a plurality of structural units (A) may be present in a block shape or in a random shape.

The polymerizable monomer (A) (monomer A) is a polymerizable monomer having a sulfobetaine structure. The sulfobetaine structure included in the structural unit derived from the monomer A is excellent in effect of imparting the lubricating property. Therefore, the hydrophilic copolymer having the structural unit derived from the monomer A is considered to be excellent in lubricating property. A homopolymer of the monomer A is soluble in an aqueous NaCl solution, but is insoluble or difficult to dissolve in water or a lower alcohol. Therefore, it is suggested that the sulfobetaine structure may have a strong electrostatic interaction. Therefore, a strong cohesive force acts inside the surface lubricious layer containing the hydrophilic copolymer according to the disclosure here. Accordingly, the surface lubricious layer is considered to have a high strength (excellent in durability). Note that the above is theory, and the invention is not limited to the above theory.

Here, the "sulfobetaine structure" refers to a structure in which a positive charge and a negative charge containing a sulfur element are present in positions not adjacent to each other, a dissociable hydrogen atom is not bonded to an atom having the positive charge, and a sum of the charges is zero.

The monomer A is not particularly limited, and examples thereof include compounds represented by the following general formulas.

[Chem. 3]

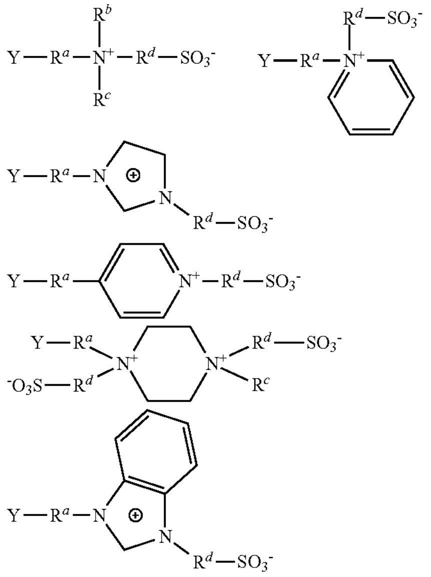

In the above general formulas, $R^a$ and $R^d$ may each independently represent a substitutable alkylene group having 1 to 30 carbon atoms or a substitutable arylene group having 6 to 30 carbon atoms. $R^b$ and $R^c$ may each independently represent a substitutable alkyl group having 1 to 30 carbon atoms or a substitutable aryl group having 6 to 30 carbon atoms. Y may represent a group having an ethylenically unsaturated group such as an acryloyl group ($CH_2{=}CH{-}C({=}O){-}$), a methacryloyl group ($CH_2{=}C(CH_3){-}C({=}O){-}$), and a vinyl group ($CH_2{=}CH{-}$). Here, in the above general formulas, the sum of the positive charges and the negative charges is zero.

Examples of the alkylene group having 1 to 30 carbon atoms include a methylene group, an ethylene group, a trimethylene group, a propylene group, an isopropylene group, a butylene group, an isobutylene group, a sec-butylene group, a tert-butylene group, and a pentylene group.

Examples of the arylene group having 6 to 30 carbon atoms include a phenylene group, a naphthylene group, an anthracenylene group, a phenanthrenylene group, a pyrenylene group, a peryleneylene group, a fluorenylene group, and a biphenylene group.

Examples of the alkyl group having 1 to 30 carbon atoms include a methyl group, an ethyl group, an n-propyl group, an isopropyl group, an n-butyl group, an isobutyl group, a sec-butyl group, a tert-butyl group, an n-pentyl group, an iso-amyl group, a tert-pentyl group, a neopentyl group, and an n-hexyl group.

Examples of the aryl group having 6 to 30 carbon atoms include a phenyl group, a biphenyl group, a terphenyl group, a pentarenyl group, an indenyl group, a naphthyl group, an azulenyl group, a heptalenyl group, and a biphenylenyl group.

Among these, from the viewpoint of further improving the lubricating property and the durability (lubrication retaining property), the monomer A is preferably a compound represented by the following formula (1). That is, in a preferred embodiment the polymerizable monomer (A) is represented by the following formula (1).

[Chem. 4]

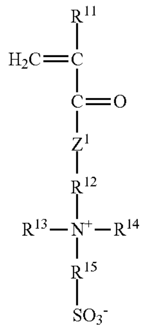

(1)

In the formula (1), $R^{11}$ represents a hydrogen atom or a methyl group. $Z^1$ represents an oxygen atom (—O—) or —NH—, preferably an oxygen atom (—O—).

In the above formula (1), from the viewpoint of further improving the lubricating property and the durability (lubrication retaining property), $R^{12}$ and $R^{15}$ each independently represent a linear or branched alkylene group having 1 to 20 carbon atoms, preferably a linear or branched alkylene group having 1 to 12 carbon atoms, more preferably a linear or branched alkylene group having 1 to 8 carbon atoms, still more preferably a linear or branched alkylene group having 1 to 6 carbon atoms, even more preferably a linear alkylene group having 1 to 4 carbon atoms (methylene group, ethylene group, trimethylene group, or tetramethylene group), and particularly preferably a linear alkylene group having 1 to 3 carbon atoms (methylene group, ethylene group, or trimethylene group). From the viewpoint of further improving the lubricating property and the durability (lubrication retaining property), as a combination of $R^{12}$ and $R^{15}$, $R^{12}$ preferably represents an ethylene group and $R^{15}$ preferably represents a trimethylene group, or $R^{12}$ preferably represents a trimethylene group and $R^{15}$ preferably represents a tetramethylene group.

In the above formula (1), from the viewpoint of further improving the lubricating property and the durability (lubrication retaining property), $R^{13}$ and $R^{14}$ each independently represent a linear or branched alkyl group having 1 to 20 carbon atoms, preferably a linear or branched alkyl group having 1 to 12 carbon atoms, more preferably a linear or branched alkyl group having 1 to 8 carbon atoms, still more preferably a linear or branched alkyl group having 1 to 4 carbon atoms, and particularly preferably a methyl group.

Examples of the compound represented by the above formula (1) include {2-[(meth)acryloyloxy]ethyl}dimethyl-(3-sulfopropyl)ammonium hydroxide, {2-[(meth)acryloyloxy]ethyl}dimethyl-(2-sulfoethyl)ammonium hydroxide, {2-[(meth)acryloyloxy]ethyl}dimethyl-(2-sulfobutyl)ammonium hydroxide, {2-[(meth)acryloyloxy]ethyl}diethyl-(2-sulfoethyl)ammonium hydroxide, {2-[(meth)acryloyloxy]ethyl}diethyl-(3-sulfopropyl)ammonium hydroxide, {2-[(meth)acryloyloxy]ethyl}diethyl-(2-sulfobutyl)ammonium hydroxide, {3-[(meth)acryloyloxy]propyl}dimethyl-(2-sulfoethyl)ammonium hydroxide, {3-[(meth)acryloyloxy]propyl}dimethyl-(3-sulfopropyl)ammonium hydroxide, {3-[(meth)acryloylamino)propyl}dimethyl(3-sulfobutyl)ammonium hydroxide, {3-[(meth)acryloyloxy]propyl}diethyl-(2-sulfoethyl)ammonium hydroxide, {3-[(meth)acryloyloxy]propyl}diethyl-(3-sulfopropyl) ammonium hydroxide, and {3-[(meth)acryloyloxy]propyl}diethyl-(3-sulfobutyl)ammonium hydroxide. Among these, {2-[(meth)acryloyloxy]ethyl}dimethyl-(3-sulfopropyl)ammonium hydroxide and {3-[(meth)acryloyloxy)propyl]dimethyl(3-sulfobutyl)ammonium hydroxide are preferred, {2-[methacryloyloxy]ethyl}dimethyl-(3-sulfopropyl)ammonium hydroxide (MSPB) and [3-(methacryloylamino)propyl]dimethyl(3-sulfobutyl) ammonium hydroxide (MSBB) are more preferred, and {2-[methacryloyloxy]ethyl}dimethyl-(3-sulfopropyl)ammonium hydroxide (MSPB) is still more preferred. The above compounds may be used alone or in combination of two or more types thereof.

As the monomer A, either a synthetic product or a commercially available product may be used. The commercially available product is available from Sigma-Aldrich Co. LLC., FUJIFILM Wako Pure Chemical Corporation, and the like. An exemplary compound may be synthesized with reference to A. Laschewsky, polymers, 6, 1544-1601 (2014), and the like.

The monomer A is not limited to the compounds represented by the above general formulas, and may be a compound having a form in which a positive charge is present at a terminal end.

In the hydrophilic copolymer, when a total of structural units derived from all the monomers is 100 mol %, a content of the structural unit derived from the monomer A is preferably 0.1 mol % to 99 mol %, more preferably 1 mol % to 99 mol %, still more preferably 5 mol % to 99 mol %, and particularly preferably 10 mol % to 99 mol %. Within such a range, a balance between the lubricating property and the solvent solubility is good. Note that when the structural unit (A) is constituted by two or more types of structural units (A), a composition of the above structural unit (A) occupies a ratio (molar ratio (mol %)) of all the structural units (A) with respect to the total of the structural units derived from all the monomers (100 mol %). The mol % is substantially equivalent to a ratio of a charge amount (mol) of the monomer A with respect to a total charge amount (mol) of all the monomers in the production of the polymer.

(Polymerizable Monomer (B))

The hydrophilic copolymer contains the structural unit derived from the polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof (the structural unit (B)). Here, the structural unit (B) constituting the hydrophilic copolymer may be one type alone or a combination of two or more types. That is, the structural unit (B) may be constituted by only one type of structural unit (B), or may be constituted by two or more types of structural units (B). Note that a plurality of structural units (B) may be present in a block shape or in a random shape.

The polymerizable monomer (B) (monomer B) is a polymerizable monomer having at least one group selected from the group consisting of a sulfonic acid group (—$SO_3H$), a sulfuric acid group (—$OSO_3H$), a sulfurous acid group (—$OSO_2H$), and salt groups thereof. By introducing such a group, anionization occurs in an aqueous solvent, and electrostatic repulsion occurs between the hydrophilic copolymers. As a result, an electrostatic interaction between the sulfobetaine structures and a hydrophobic interaction between the photoreactive groups in the hydrophilic copolymers are reduced. Therefore, the solvent solubility of the copolymer (particularly the solubility in water, a lower alcohol, or a mixed solvent of water and a lower alcohol) is improved. This improving effect is particularly remarkable when the photoreactive group of the monomer C is a benzophenone group. Since the benzophenone group has a plurality of aromatic rings, the benzophenone groups are likely to associate with each other by a π-π interaction, which makes the polymers containing the benzophenone group to aggregate and insolubilize. Therefore, it is considered that by introducing the structural unit derived from the monomer B, the electrostatic repulsion occurs as described above, and the association between the benzophenone groups is reduced, and thus the solubility or dispersibility of the polymer is rapidly improved. Note that the above mechanism is theory, and the invention is not limited to the above theory. Alternatively, even when the monomer C has an ester group, the above improving effect can be obtained satisfactorily. In addition to the above groups, the monomer B preferably has an ethylenically unsaturated group such as a (meth)acryloyl group, a vinyl group, or an allyl group.

Among these, from the viewpoint of further improving the solvent solubility, the monomer B is preferably a compound represented by the following formula (2), (3), or (4), and more preferably a compound represented by the following formula (2). That is, in a preferred embodiment, the polymerizable monomer (B) is represented by the following formula (2), (3), or (4). In a more preferred embodiment, the polymerizable monomer (B) is represented by the following formula (2).

[Chem. 5]

(2)

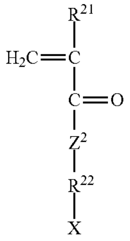

In the above formula (2), $R^{21}$ represents a hydrogen atom or a methyl group. $Z^2$ represents an oxygen atom (—O—) or —NH—, and preferably —NH—.

In the above formula (2), from the viewpoint of further improving the solvent solubility, $R^{22}$ represents a linear or branched alkylene group having 1 to 20 carbon atoms, preferably a linear or branched alkylene group having 1 to 12 carbon atoms, more preferably a linear or branched alkylene group having 1 to 8 carbon atoms, still more preferably a linear or branched alkylene group having 1 to 6 carbon atoms, and particularly preferably a branched alkylene group having 3 to 5 carbon atoms. The branched alkylene group having 3 to 5 carbon atoms is a group represented by $—CH(CH_3)—CH_2—$, $—C(CH_3)_2—CH_2—$, $—CH(CH_3)—CH(CH_3)—$, $—C(CH_3)_2—CH_2—CH_2—$, $—CH(CH_3)—CH(CH_3)—CH_2—$, $—CH(CH_3)—CH_2—CH(CH_3)—$, $—CH_2—C(CH_3)_2—CH_2—$, $—C(CH_3)_2—CH(CH_3)—$, or the like (a connection order of the above groups in the formula (2) is not particularly limited), and among these, a group represented by $—C(CH_3)_2—CH_2—$ is particularly preferred.

In the above formula (2), X represents a group selected from the group consisting of a sulfonic acid group ($—SO_3H$), a sulfuric acid group ($—OSO_3H$), a sulfurous acid group ($—OSO_2H$), and salt groups thereof. From the viewpoints of acid dissociation (that is, ease of anionization) and even the solvent solubility of the copolymer, X preferably represents a group selected from the group consisting of a sulfonic acid group, a sulfuric acid group, and salt groups thereof. From the viewpoint of easy availability of monomers, X more preferably represents a sulfonic acid group or a salt group thereof. Here, the salt is not particularly limited, and for example, the salt may be an alkali metal salt (sodium salt, potassium salt, or the like) of the above group.

Examples of the compound represented by the above formula (2) include 2-(meth)acrylamide-2-methyl-1-propanesulfonic acid, 1-[(meth)acryloyloxymethyl]-1-propanesulfonic acid, 2-[(meth)acryloyloxy]-2-propanesulfonic acid, 3-[(meth)acryloyloxy]-1-methyl-1-propanesulfonic acid, 2-sulfoethyl(meth)acrylate, 3-sulfopropyl(meth)acrylate, and salts thereof (preferably a sodium salt or a potassium salt). Among these, 2-(meth)acrylamide-2-methyl-1-propanesulfonic acid or a salt thereof (particularly alkali metal salt) is preferred, and 2-acrylamide-2-methyl-1-propanesulfonic acid or a salt thereof (particularly sodium salt) is more preferred. These compounds may be used alone or in combination of two or more types thereof.

The compound represented by the above formula (2) may be either a synthetic product or a commercially available product, and the commercially available product is available from Tokyo Chemical Industry Co., Ltd., Sigma-Aldrich Co. LLC., and the like.

[Chem. 6]

(3)

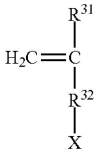

In the above formula (3), $R^{31}$ represents a hydrogen atom or a methyl group.

In the above formula (3), $R^{32}$ represents a single bond or a linear or branched alkylene group having 1 to 20 carbon atoms, preferably a single bond or a linear or branched alkylene group having 1 to 12 carbon atoms, more preferably a single bond or a linear or branched alkylene group having 1 to 8 carbon atoms, still more preferably a single bond or a linear or branched alkylene group having 1 to 4 carbon atoms, and particularly preferably a single bond. Here, since specific examples of the alkylene group are the same as those for the above formula (2), description thereof is omitted here.

In the above formula (3), X represents a group selected from the group consisting of a sulfonic acid group ($—SO_3H$), a sulfuric acid group ($—OSO_3H$), a sulfurous acid group ($—OSO_2H$), and salt groups thereof. From the viewpoints of the acid dissociation (that is, the ease of anionization) and even the solvent solubility of the copolymer, X preferably represents a group selected from the group consisting of a sulfonic acid group, a sulfuric acid group, and salt groups thereof. From the viewpoint of easy availability of monomers, X more preferably represents a sulfonic acid group or a salt group thereof.

Examples of the compound represented by the above formula (3) include vinyl sulfonic acid, allyl sulfonic acid, methallyl sulfonic acid, 2-propene-1-sulfonic acid, 2-methyl-2-propene-1-sulfonic acid, and salts thereof. These compounds may be used alone or in combination of two or more types thereof.

The compound represented by the above formula (3) may be either a synthetic product or a commercially available product, and the commercially available product is available from Asahi Kasei Finechem Co., Ltd., Tokyo Chemical Industry Co., Ltd. (for example, sodium salt of 2-methyl-2-propene-1-sulfonic acid), and the like.

[Chem. 7]

(4)

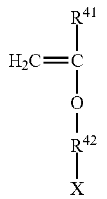

In the above formula (4), $R^{41}$ represents a hydrogen atom or a methyl group.

In the above formula (4), $R^{42}$ represents a linear or branched alkylene group having 1 to 20 carbon atoms, preferably a linear or branched alkylene group having 1 to 12 carbon atoms, more preferably a linear or branched alkylene group having 1 to 8 carbon atoms, and still more preferably a linear or branched alkylene group having 1 to 6 carbon atoms. Here, since specific examples of the alkylene group are the same as those for the above formula (2), description thereof is omitted here.

In the above formula (4), X represents a group selected from the group consisting of a sulfonic acid group ($—SO_3H$), a sulfuric acid group ($—OSO_3H$), a sulfurous acid group ($—OSO_2H$), and salt groups thereof. From the viewpoints of the acid dissociation (that is, the ease of anionization) and even the solvent solubility of the copolymer, X preferably represents a group selected from the group consisting of a sulfonic acid group, a sulfuric acid group, and salt groups thereof. From the viewpoint of easy availability of monomers, X more preferably represents a sulfonic acid group or a salt group thereof.

Examples of the compound represented by the above formula (4) include 2-sulfoxyethyl vinyl ether, 3-sulfoxy-n-propyl vinyl ether, and salts thereof. These compounds may be used alone or in combination of two or more types thereof.

As the compound represented by the above formula (4), either a synthetic product or a commercially available product may be used.

In the hydrophilic copolymer, when the total of the structural units derived from all the monomers is 100 mol %, a content of the structural unit derived from the monomer B is preferably 0.1 mol % to 99 mol %, more preferably 0.2 mol % to 99 mol %, still more preferably 0.5 mol % to 99 mol %, and particularly preferably 1 mol % to 99 mol %. Within such a range, a balance between the lubricating property and the solvent solubility is good. Note that when the structural unit (B) is constituted by two or more types of structural units (B), a composition of the above structural unit (B) occupies a ratio (molar ratio (mol %)) of all the structural units (B) with respect to the total of the structural units derived from all the monomers (100 mol %). The mol % is substantially equivalent to a ratio of a charge amount (mol) of the monomer B with respect to the total charge amount (mol) of all the monomers in the production of the polymer.

(Polymerizable Monomer (C))

The hydrophilic copolymer contains the structural unit derived from the polymerizable monomer (C) having a photoreactive group (structural unit (C)). Here, the structural unit (C) constituting the hydrophilic copolymer may be one type alone or a combination of two or more types. That is, the structural unit (C) may be constituted by only one type of structural unit (C), or may be constituted by two or more types of structural units (C). Note that a plurality of structural units (C) may be present in a block shape or in a random shape.

The polymerizable monomer (C) (monomer C) is a polymerizable monomer having a photoreactive group. Here, the "photoreactive group" refers to a group that can generate reactive species such as radicals, nitrenes, and carbenes by being irradiated with active energy rays, and react with a material constituting a layer adjacent to the surface lubricious layer (for example, the substrate layer) and the water-retaining material in the surface lubricious layer to form a chemical bond.

Accordingly, the surface lubricious layer containing the hydrophilic copolymer can be firmly immobilized to the adjacent layer (for example, the substrate layer). The water-retaining material can be firmly immobilized in the surface lubricious layer. Therefore, the medical device disclosed here can exhibit sufficient durability (lubrication retaining property). The monomer C preferably has an ethylenically unsaturated group such as a (meth)acryloyl group, a vinyl group, or an allyl group, in addition to the above photoreactive group.

Examples of the photoreactive group include an azide group, a diazo group, a diazirine group, a ketone group, and a quinone group.

Examples of the azide group include an aryl azide group of phenyl azide and 4-fluoro-3-nitrophenyl azide, an acyl azide group of benzoyl azide and p-methylbenzoyl azide, an azidoformate group of ethyl azideformate and phenyl azideformate, a sulfonyl azide group of benzenesulfonyl azide, and a phosphoryl azide group of diphenylphosphoryl azide and diethyl phosphoryl azide.

Examples of the diazo group include a group derived from diazoalkanes such as diazomethane and diphenyldiazomethane, diazoketones such as diazoacetophenone and 1-trifluoromethyl-1-diazo-2-pentanone, diazoacetates such as t-butyldiazoacetate and phenyldiazoacetate, and α-diazoacetoacetates such as t-butyl-α-diazoacetoacetate.

Examples of the diazirine group include a group derived from 3-trifluoromethyl-3-phenyldiazirine.

Examples of the ketone group include a group having a structure such as acetophenone, benzophenone, anthrone, xanthine, and thioxanthone.

Examples of the quinone group include a group derived from anthraquinone.

These photoreactive groups are appropriately selected depending on the type of the substrate layer of the medical device and the like. For example, when the substrate layer is made of a polyolefin resin such as a polyethylene resin, a polyamide resin, a polyurethane resin, a polyester resin, or the like, the photoreactive group is preferably a ketone group or a phenyl azide group, and more preferably a group having a benzophenone structure (a benzophenone group) from the viewpoint of easy availability of monomers. That is, in a preferred embodiment, the polymerizable monomer (C) has a group having a benzophenone structure.

Examples of the monomer C include 2-azidoethyl (meth) acrylate, 2-azidopropyl (meth)acrylate, 3-azidopropyl (meth)acrylate, 4-azidobutyl (meth)acrylate, 4-(meth)acryloyloxybenzophenone, 4-(meth)acryloyloxyethoxybenzophenone, 4-(meth)acryloyloxy-4'-methoxybenzophenone, 4-(meth)acryloyloxyethoxy-4'-methoxybenzophenone, 4-(meth)acryloyloxy-4'-bromobenzophenone, 4-(meth) acryloyloxyethoxy-4'-bromobenzophenone, 4-styrylmethoxybenzophenone, 4-(meth)acryloyloxythioxanthone, and 2-(meth)chryloyloxyethyl-4-azidobenzoate.

As the monomer C, either a synthetic product or a commercially available product may be used, and the commercially available product is available from MCC UNITEC Co., Ltd. and the like.

In the hydrophilic copolymer, when the total of the structural units derived from all the monomers is 100 mol %, a content of the structural unit derived from the monomer C is preferably 0.1 mol % to 40 mol %, more preferably 0.1 mol % to 30 mol %, still more preferably 0.1 mol % to 25 mol %, and particularly preferably 0.1 mol % to 20 mol %. Within such a range, the hydrophilic copolymer can be sufficiently bonded to a material constituting the layer adjacent to the surface lubricious layer (in particular, the substrate layer), and thus the surface lubricious layer can be more firmly immobilized to the adjacent layer (in particular, the substrate layer). Therefore, the medical device according can exhibit sufficient durability (lubrication retaining property). Within such a range, a sufficient amount of other monomers (the monomers A and B) can be present, so that the sufficient lubricating property and durability by the monomer A and the solvent solubility by the monomer B in the hydrophilic copolymer can be more effectively improved. Note that when the structural unit (C) is constituted by two or more types of structural units (C), a composition of the above structural unit (C) occupies a ratio (molar ratio (mol %)) of all the structural units (C) with respect to the total of the structural units derived from all the monomers (100 mol %). The mol % is substantially equivalent to a ratio of a charge amount (mol) of the monomer C with respect to the total charge amount (mol) of all the monomers in the production of the polymer.

The hydrophilic copolymer may contain a structural unit derived from a polymerizable monomer other than the above monomer A, monomer B, and monomer C (hereinafter, also referred to as "other monomer") in a range that does not impair the effects intended. In the hydrophilic copolymer according to the disclosure here, a content of the structural unit derived from the other monomer is preferably less than 10 mol %, more preferably less than 5 mol %, and still more preferably less than 1 mol % (lower limit: more than 0 mol %), with respect to 100 mol %, which is the total of the structural units derived from all the monomers. Note that when the structural unit derived from the other monomer is constituted by two or more types of structural units, a composition of the above structural unit derived from the other monomer occupies a ratio (molar ratio (mol %)) of all the structural units derived from the other monomer with respect to the total of the structural units derived from all the monomers (100 mol %). Preferably, the hydrophilic copolymer is constituted by the monomer A, the monomer B, and the monomer C (the composition of the other monomer=0 mol %). Note that the mol % is substantially equivalent to a ratio of a charge amount (mol) of the other monomer with respect to the total charge amount (mol) of all the monomers in the production of the polymer.

A terminal end of the hydrophilic copolymer is not particularly limited, and is appropriately defined depending on types of raw materials to be used, and is usually a hydrogen atom. A structure of the copolymer is not particularly limited, and may be any of a random copolymer, an alternating copolymer, a periodic copolymer, and a block copolymer.

A weight average molecular weight (Mw) of the hydrophilic copolymer is preferably several thousand to several million, more preferably 1,000 to 1,000,000, and particularly preferably 5,000 to 500,000. In the disclosure here, the "weight average molecular weight" shall be a value measured by gel permeation chromatography (GPC) using polyethylene glycol as a standard substance.

[Method for Manufacturing Hydrophilic Copolymer]

A method for manufacturing the hydrophilic copolymer is not particularly limited, and known polymerization methods such as radical polymerization, anionic polymerization, and cationic polymerization can be adopted. The radical polymerization that is easy in production is preferably used.

As the polymerization method, a method of copolymerizing the above monomer A, monomer B, monomer C, and if necessary, the other monomer by stirring and heating together with a polymerization initiator in a polymerization solvent is usually adopted.

A polymerization temperature is not particularly limited, and is preferably 25° C. to 100° C., and more preferably 30° C. to 80° C. A polymerization time is also not particularly limited, and is preferably 30 minutes to 24 hours, and more preferably 1 hour to 8 hours.

The polymerization solvent is preferably water, and an aqueous solvent such as alcohols such as methanol, ethanol, propanol, n-butanol, and 2,2,2-trifluoroethanol. From the viewpoint of dissolving raw materials to be used for the polymerization, these polymerization solvents may be used alone or in combination of two or more types thereof.

A concentration of the polymerizable monomers is not particularly limited, and a total solid content (g) of each polymerizable monomer with respect to the polymerization solvent (mL) is preferably 0.05 g/mL to 1 g/mL, and more preferably 0.1 g/mL to 0.5 g/mL. The preferred ratio of the charge amount (mol) of each monomer to the total charge amount (mol) of all the monomers is as described above.

A reaction solution containing the polymerizable monomers may be subjected to a degassing treatment before the polymerization initiator is added. The degassing treatment may be performed by, for example, bubbling the reaction solution with an inert gas such as nitrogen gas and argon gas for approximately 0.5 hours to 5 hours. During the degassing treatment, the reaction solution may be heated to approximately 30° C. to 100° C.

Known polymerization initiators in the related art can be used in the production of the polymer, and the polymerization initiator is not particularly limited. For example, an azo-based polymerization initiator such as 2,2'-azobisisobutyronitrile, 2,2'-azobis(4-methoxy-2,4-dimethylvaleronitrile), 4,4'-azobis(4-cyanovaleric acid), and 2,2'-azobis(2,4-dimethylvaleronitrile), and a redox-based polymerization initiator in which a reducing agent such as sodium sulfite, sodium hydrogen sulfite, and ascorbic acid is combined with an oxidizing agent such as a persulfate such as potassium persulfate (KPS), sodium persulfate, and ammonium persulfate, and a peroxide such as hydrogen peroxide, t-butyl peroxide, and methyl ethyl ketone peroxide can be used.

A blending amount of the polymerization initiator is preferably 0.001 mol % to 10 mol %, and more preferably 0.01 mol % to 5 mol % with respect to a total amount (mol) of the polymerizable monomers.

Further, if necessary, a chain transfer agent, a polymerization rate adjusting agent, a surfactant, and other additives may be appropriately used in the polymerization.

An atmosphere in which the polymerization reaction is performed is not particularly limited, and the polymerization reaction can be performed in air atmosphere, an atmosphere of an inert gas such as nitrogen gas and argon gas, and the like. During the polymerization reaction, the reaction solution may be stirred.

The copolymer may be precipitated during the polymerization reaction. The copolymer after polymerization can be purified by a general purification method such as a reprecipitation method, a dialysis method, an ultrafiltration method, and an extraction method.

The copolymer after purification can be dried by any method such as freeze drying, vacuum drying, spray drying, and heat drying, but from the viewpoint of having a small influence on physical properties of the polymer, freeze drying or vacuum drying is preferred.

Unreacted monomers contained in the obtained copolymer are preferably 0.01 wt % or less with respect to the total amount of the copolymer. A smaller amount of unreacted monomers is preferred (lower limit: 0 wt %). A content of the remaining monomers can be measured by a known method such as high performance liquid chromatography.

[Method for Manufacturing Medical Device]

A method for manufacturing the medical device is not particularly limited except that the surface lubricious layer is formed using the hydrophilic copolymer and the hydroxy group-containing compound (1), and a known method can be applied in the same manner or after appropriate modification. For example, preferred is a method in which a coating liquid is prepared by dissolving the hydrophilic copolymer and the hydroxy group-containing compound (1) in a solvent, and is coated onto the substrate layer of the medical device to form the surface lubricious layer. That is, the disclosure here also provides the method for manufacturing a medical device, the method including coating a coating liquid containing the hydroxy group-containing compound (1) and the hydrophilic copolymer onto the substrate layer to form the surface lubricious layer. With such a method, the lubricating property and the durability (lubrication retaining property) can be imparted to the surface of the medical device.

(Coating Step for Surface Lubricious Layer)

Here, a coating liquid is prepared by dissolving the hydrophilic copolymer and the hydroxy group-containing compound (1) in a solvent, and is coated onto the substrate layer. In the above method, the solvent used for dissolving the hydrophilic copolymer and the hydroxy group-containing compound (1) is preferably water, a lower alcohol, or a mixed solvent of water and a lower alcohol from the viewpoints of working safety (low toxicity) and solubility. Here, the lower alcohol refers to a primary alcohol having 1 to 3 carbon atoms, that is, methanol, ethanol, n-propanol, or isopropanol. The above lower alcohols may be used alone or in combination of two or more types thereof. Here, the hydrophilic copolymer and the hydroxy group-containing compound (1) may be added to the solvent together, may be sequentially added to the same solvent (the hydrophilic copolymer and then the hydroxy group-containing compound (1), or the hydroxy group-containing compound (1) and then the hydrophilic copolymer), or the hydrophilic copolymer and the hydroxy group-containing compound (1) may be dissolved in different solvents and then mixed with each other. Note that when the hydrophilic copolymer and the hydroxy group-containing compound (1) may be dissolved in different solvents, the solvents may be the same or different from each other, and are preferably the same in consideration of ease of operation and the like.

A lower limit of a concentration of the hydrophilic copolymer in the coating liquid is preferably 0.01 wt % or more, more preferably 0.1 wt % or more, still more preferably 1 wt % or more, and particularly preferably 5 wt % or more. Within such a range, a strong and uniform chemical bond can be formed with the material constituting the substrate layer by subsequent irradiation with active energy rays (immobilizing step for surface lubricious layer). As a result, a medical device having excellent lubricating property and durability (lubrication retaining property) can be obtained. An upper limit of the concentration of the hydrophilic copolymer in the coating liquid is not particularly limited, and is preferably 50 wt % or less, more preferably 30 wt % or less, still more preferably 20 wt % or less, and particularly preferably 15 wt % or less. Within such a range, the coating liquid is excellent in terms of coatability and production efficiency.

A concentration of the hydroxy group-containing compound (1) in the coating liquid is not particularly limited, and is, for example, 0.1 wt % to 5 wt %, preferably 0.4 wt % to 4 wt %, and particularly preferably 0.5 wt % to 3 wt %. Within such a range, the coatability of the coating liquid is good, and the obtained surface lubricious layer can exhibit a sufficient water-retaining effect (therefore, the surface lubricious layer can exhibit excellent lubricating property even under a high load condition).

A mixing ratio of the hydrophilic copolymer with respect to the hydroxy group-containing compound (1) in the coating liquid is not particularly limited, and is preferably the same mixing ratio as described in the section of Surface Lubricious Layer.

A coating amount of the coating liquid is not particularly limited, and is preferably an amount that corresponds to the thickness of the above surface lubricious layer.

Before coating the coating liquid, the surface of the substrate layer may be treated in advance by an ultraviolet irradiation treatment, a plasma treatment, a corona discharge treatment, a flame treatment, an oxidation treatment, a silane coupling treatment, a phosphoric acid coupling treatment, or the like. When the solvent of the coating liquid is only water, it is difficult to coat the coating liquid onto the surface of the hydrophobic substrate layer, and the surface of the substrate layer is made hydrophilic by performing a plasma treatment on the surface of the substrate layer. Accordingly, wettability of the coating liquid to the surface of the substrate layer is improved, and a uniform surface lubricious layer can be formed. By applying the above treatment to the surface of the substrate layer, which does not have any C—H bond of a metal, a fluororesin, or the like, a covalent bond with the photoreactive group of the hydrophilic copolymer can be formed.

A method for coating the coating liquid onto the surface of the substrate layer is not particularly limited, and a known method in the related art can be applied, such as a coating printing method, an immersion method (dipping method, dip coating method), a spraying method (spray method), a spin coating method, and a mixed solution impregnated sponge coating method. Among these, the immersion method (dipping method, dip coating method) is preferred.

(Drying Step for Surface Lubricious Layer)

As described above, it is preferable that, after immersing the substrate layer in the coating liquid, the substrate layer is taken out from the coating liquid, and a coating film is dried. Drying conditions are not particularly limited as long as the solvent can be removed from the coating film, and a warm air treatment may be performed using a dryer or the like, or natural drying may be performed. A pressure condition during the drying is also not limited at all, and the drying may be performed under a normal pressure (atmospheric pressure), or under a pressure or a reduced pressure. As a drying unit (device), for example, an oven, a decompression dryer, or the like can be used, and in the case of natural drying, no drying unit (device) is particularly required.

(Immobilizing Step for Surface Lubricious Layer)

The coating film after the drying step is irradiated with active energy rays. Accordingly, the photoreactive group of the hydrophilic copolymer (monomer C) in the surface lubricious layer is activated, and a chemical bond is formed between the photoreactive group and a hydrocarbon group of the material constituting the substrate layer, and between the photoreactive group and the hydrocarbon group of the hydroxy group-containing compound (1) in the surface lubricious layer. For example, a case of a combination of the photoreactive group having a benzophenone structure of the hydrophilic copolymer and the hydroxy group-containing compound (1) in the surface lubricious layer will be described. When the hydrophilic copolymer has the photoreactive group having a benzophenone structure, two radicals are generated in the photoreactive group of the hydrophilic copolymer by irradiation with ultraviolet rays. One of these radicals abstracts the hydrogen atom from the hydrocarbon group of the hydroxy group-containing compound (1), and instead one radical is generated in the hydroxy group-containing compound (1). Then, the remaining radical in the photoreactive group and the radical generated in the hydroxy group-containing compound (1) are bonded to each other, whereby a covalent bond is formed between the photoreactive group of the hydrophilic copolymer and the hydroxy group-containing compound (1) in the surface lubricious layer. With such a chemical bond between the hydroxy group-containing compound (1) and the hydrophilic copolymer in the surface lubricious layer, the hydroxy group-containing compound (1) is firmly immobilized in the surface lubricious layer. In addition, one of the two radicals of the hydrophilic copolymer generated by the irradiation with the ultraviolet rays abstracts the hydrogen atom from the hydrocarbon group in the material constituting the substrate layer, and instead one radical is generated in the material constituting the substrate layer. Then, the remaining radical in the photoreactive group of the hydrophilic copolymer and the radical generated in the material constituting the substrate layer are bonded to each other, whereby a covalent bond is formed between the photoreactive group of the hydrophilic copolymer in the surface lubricious layer and the material constituting the substrate layer. As a result, the surface lubricious layer is firmly immobilized on the substrate layer. Therefore, the surface lubricious layer can effectively exhibit the water retention effect of the hydroxy group-containing compound (1) and can exhibit excellent lubricating property. The water retention effect of the hydroxy group-containing compound (1) can be maintained for a long period of time, and the excellent durability (lubrication retaining property) can also be exhibited. Further, a surface lubricious layer that is excellent in lubricating property and durability (lubrication retaining property) can be obtained even by irradiating with active energy rays for a short period of time (for example, less than 5 minutes). The reason thereof is considered as that the hydroxy group contained in the hydroxy group-containing compound (1) promotes the formation of the chemical bond by the photoreactive group. Note that it is considered that the hydroxy group-containing compound (2) in the second aspect and the hydroxy group-containing compound (3) in the third aspect also act in the same manner as the hydroxy group-containing compound (1). Note that the above is theory, and the invention is not limited to the above theory.

Examples of the active energy rays include ultraviolet rays (UV), electron beams, and gamma rays, and are preferably ultraviolet rays or electron beams, and more preferably ultraviolet rays in consideration of an influence on a human body. When the active energy rays are ultraviolet rays, a wavelength at which the photoreactive group can be activated can be appropriately selected as an irradiation wavelength. Specifically, a wavelength range of the ultraviolet rays is preferably 200 nm to 400 nm, and more preferably 220 nm to 390 nm. The irradiation with ultraviolet rays is preferably performed under a temperature condition of 10° C. to 100° C., and more preferably 20° C. to 80° C. An irradiation intensity of the ultraviolet rays is not particularly limited, and is preferably 1 $mW/cm^2$ to 5000 $mW/cm^2$, more preferably 1 $mW/cm^2$ to 1000 $mW/cm^2$, and still more preferably 10 $mW/cm^2$ to 1000 $mW/cm^2$. An integrated light amount of the ultraviolet rays is not particularly limited, and is preferably 50 $mJ/cm^2$ to 100,000 $mJ/cm^2$, more preferably 50 $mJ/cm^2$ to 50,000 $mJ/cm^2$, still more preferably 100 $mJ/cm^2$ to 75,000 $mJ/cm^2$, and particularly preferably 100 $mJ/cm^2$ to 10,000 $mJ/cm^2$.

Examples of a device for emitting the ultraviolet rays include a high-pressure mercury lamp, a low-pressure mercury lamp, a metal halide lamp, a xenon lamp, and a halogen lamp. Note that a method for emitting the active energy rays is not particularly limited, and the irradiation may be performed from one direction, or from multiple directions, or the irradiation may be performed while rotating an irradiation source, or while rotating an object to be irradiated (one in which the coating film of the surface lubricious layer is formed on the substrate layer).

After performing the above irradiation with the active energy rays, the coating film may be washed with a solvent (for example, the solvent used for preparing the coating liquid) to remove the unreacted hydrophilic copolymer.

The immobilization of the coating film (surface lubricious layer) on the substrate layer can be confirmed by using a known analytical method such as FT-IR, XPS, and TOF-SIMS. For example, the immobilization can be confirmed by performing FT-IR measurement before and after the irradiation with active energy rays, and comparing ratios of a peak of bonds formed by the irradiation with active energy rays with respect to a peak of invariant bonds.

With the above method, in the medical device disclosed here, the surface lubricious layer containing the hydrophilic copolymer and the hydroxy group-containing compound (1) is formed on the surface of the substrate layer.

<Second Aspect>

The second aspect of the disclosure here relates to a medical device including: a substrate layer; and a surface lubricious layer formed on at least a part of the substrate layer, and containing a hydroxy group-containing compound (hydroxy group-containing compound (2)) represented by the following formula and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($-SO_3H$), a sulfuric acid group ($-OSO_3H$), a sulfurous acid group ($-OSO_2H$), and salt groups thereof, and a structural unit derived from a polymerizable monomer (C) having a photoreactive group.

$$X-O\{A-O\}_nY \quad \text{[Chem. 8]}$$

In the above formula,

X represents a hydrogen atom or a substituted or unsubstituted monovalent hydrocarbon group having 1 to 22 carbon atoms, A represents a group represented by $-CH_2-$, $-(CH_2)_2-$, $-(CH_2)_3-$, or $-CH_2-CH(CH_3)-$, n represents a number of 1 or more, Y represents a hydrogen atom or an acyl group, and when Y represents an acyl group, X represents a hydrogen atom or a monovalent hydrocarbon group having 1 to 7 carbon atoms substituted with a hydroxy group.

[Substrate Layer (Substrate)]

Since the substrate layer used in this aspect is the same as [Substrate Layer (Substrate)] in the above <First Aspect>, description thereof is omitted here.

[Surface Lubricious Layer]

The surface lubricious layer used in this aspect is mainly different from that in the first aspect in that the water-retaining material is not the hydroxy group-containing compound (1), but the hydroxy group-containing compound (2). Therefore, in the following, only matters different from [Surface Lubricious Layer] in the above <First Aspect> will be described. Therefore, matters not described below are understood to be the same as those in [Surface Lubricious Layer] in the above <First Aspect>.

In this aspect, the surface lubricious layer may be directly disposed above the substrate layer. Alternatively, another layer (for example, an adhesive layer) may be provided between the surface lubricious layer and the substrate layer as long as the layer does not influence functions and effects disclosed here. Note that a preferred embodiment in a case where an adhesive layer is provided between the surface lubricious layer and the substrate layer will be described in the following <Second Aspect (Embodiment Including Adhesive Layer)>.

(Hydroxy Group-Containing Compound (2))

The hydroxy group-containing compound (2) is a hydroxy group-containing compound represented by the following formula and soluble in water.

$$X-O\{A-O\}_nY \quad \text{[Chem. 9]}$$

In the above formula, X represents a hydrogen atom or a substituted or unsubstituted monovalent hydrocarbon group having 1 to 22 carbon atoms. A substituent that may be present when X is a substituted monovalent hydrocarbon group is not particularly limited, and examples thereof include the groups described above. For example, a hydroxy group is preferred. Note that when Y represents an acyl group, X represents a hydrogen atom or a monovalent hydrocarbon group having 1 to 7 carbon atoms substituted with a hydroxy group. Examples of the monovalent hydrocarbon group include those described in (Hydroxy Group-Containing Compound (1)) in the above <First Aspect>.

In the above formula, A represents a group represented by $-CH_2-$, $-(CH_2)_2-$, $-(CH_2)_3-$, or $-CH_2-CH(CH_3)-$, preferably $-CH_2-$ or $-CH_2-CH(CH_3)-$, and more preferably $-(CH_2)_2-$.

In the above formula, n represents a number of 1 or more, preferably a number of 2 or more. Moreover, n preferably represents a number of 20 or less, and more preferably a number of 12 or less.

In the above formula, Y represents a hydrogen atom or an acyl group. Here, the acyl group is a residue of a fatty acid (RCOOH), and is a group represented by $-C(=O)R$. The fatty acid is not particularly limited, and examples thereof include a saturated or unsaturated fatty acid having 10 to 24 carbon atoms, such as an oleic acid, an isostearic acid, a myristic acid, a palmitic acid, an isopalmitic acid, a lauric acid, a stearic acid, and a behenic acid. That is, the above R represents, for example, an alkyl group having 10 to 24 carbon atoms or an alkenyl group having 10 to 24 carbon atoms.

The hydroxy group-containing compound (2) is a hydroxy group-containing compound soluble in water among the hydroxy group-containing compounds described above. That is, the hydroxy group-containing compound (2) is a hydroxy group-containing compound that is dissolved by an amount of 0.001 g or more in 100 mL of distilled water under a condition of room temperature (23° C.), among the hydroxy group-containing compounds described above.

An upper limit of a molecular weight of the hydroxy group-containing compound (2) is not particularly limited, and is preferably 10,000 or less, more preferably 5,000 or less, still more preferably 2,000 or less, even more preferably 1,000 or less, and particularly preferably 500 or less. A lower limit of the molecular weight of the hydroxy group-containing compound (2) is not particularly limited, and is, for example, 50 or more. Note that when a structure of the hydroxy group-containing compound (2) is specified, the molecular weight of the compound is a molecular weight calculated based on the structure. Alternatively, when the structure of the compound is not specified, the molecular weight is a weight average molecular weight (Mw) measured in terms of polyethylene glycol by gel permeation chromatography (GPC) method.

Examples of the compound represented by the above formula include ethylene glycol, propylene glycol, diethylene glycol, dipropylene glycol, triethylene glycol, tripropylene glycol, polyethylene glycol, polypropylene glycol, a polyoxyethylene mono-fatty acid ester (for example, polyethylene glycol monolaurate and the like), a polyoxypropylene mono-fatty acid ester (for example, polypropylene glycol monolaurate and the like), a polyoxyethylene monoalkyl ether, a polyoxypropylene monoalkyl ether, a polyoxyethylene monoalkyl phenyl ether (for example, Triton (registered trademark) X-100 and the like), and a polyoxypropylene monoalkyl phenyl ether. These compounds may be used alone or in combination of two or more types thereof.

That is, in a preferred embodiment of this aspect, the hydroxy group-containing compound (2) is a hydroxy group-containing compound that is selected from the group consisting of ethylene glycol, propylene glycol, diethylene glycol, dipropylene glycol, triethylene glycol, tripropylene glycol, polyethylene glycol, polypropylene glycol, a polyoxyethylene mono-fatty acid ester, a polyoxypropylene mono-fatty acid ester, a polyoxyethylene monoalkyl ether, a polyoxypropylene monoalkyl ether, a polyoxyethylene monoalkyl phenyl ether, and a polyoxypropylene monoalkyl phenyl ether, and is soluble in water.

From the viewpoint of further improving the lubricating property and the durability (lubrication retaining property), the hydroxy group-containing compound (2) is preferably a compound having two or more hydroxy groups ($-OH$), and more preferably a compound having two hydroxy groups ($-OH$).

Alternatively, from the viewpoint of further improving the lubricating property and the durability (lubrication retaining property), the hydroxy group-containing compound (2) is preferably a compound having 2 or 3 carbon atoms between oxygen atoms. From the above viewpoint, the hydroxy group-containing compound (2) is more preferably at least one hydroxy group-containing compound that is selected from the group consisting of ethylene glycol, propylene glycol, diethylene glycol, dipropylene glycol, triethylene glycol, tripropylene glycol, polyethylene glycol, polypropylene glycol, and a polyoxyethylene monoalkyl phenyl ether, and is soluble in water, and particularly preferably polyethylene glycol, triethylene glycol, polypropylene glycol, or tripropylene glycol.

As the hydroxy group-containing compound (2), either a synthetic product or a commercially available product may be used. The commercially available product is available from Sigma-Aldrich Co. LLC., Kao Corporation, and the like.

In the surface lubricious layer, an abundance ratio (mixing ratio) of the hydroxy group-containing compound (2) with respect to the hydrophilic copolymer is not particularly limited. In the surface lubricious layer, for the abundance ratio (mixing ratio) of the hydroxy group-containing compound (2) with respect to the hydrophilic copolymer, the hydrophilic copolymer is preferably 0.1 parts by weight or more, more preferably 0.5 parts by weight or more, still more preferably 1 part by weight or more, and particularly preferably 2 parts by weight or more, with respect to 1 part by weight of the hydroxy group-containing compound (2). In the surface lubricious layer, for the abundance ratio (mixing ratio) of the hydroxy group-containing compound (2) with respect to the hydrophilic copolymer, the hydrophilic copolymer is preferably 1,000 parts by weight or less, more preferably 100 parts by weight or less, still more preferably 50 parts by weight or less, and particularly preferably 20 parts by weight or less, with respect to 1 part by weight of the hydroxy group-containing compound (2).

With such an abundance ratio (mixing ratio), the water retention effect of the hydroxy group-containing compound (2) and the lubricating property of the hydrophilic copolymer can be exhibited in a good balance. Note that when the surface lubricious layer contains two or more types of the hydroxy group-containing compounds (2), the above "1 part by weight" means that a total amount of these hydroxy group-containing compounds (2) is 1 part by weight. Similarly, when the surface lubricious layer contains two or more types of hydrophilic copolymers, the above amount (part by weight) of the hydrophilic copolymers means a total amount of these hydrophilic copolymers. The above abundance ratio (mixing ratio) is substantially equal to a ratio of a total charge amount (weight) of the hydrophilic copolymers with respect to a total charge amount (weight) of the hydroxy group-containing compounds (2) during formation of the surface lubricious layer.

Here, the presence and the ratio of the structural unit derived from each polymerizable monomer in the hydrophilic copolymer and the presence of the hydroxy group-containing compound (2) in the surface lubricious layer can be confirmed by the same method as described in the above <First Aspect>. The abundance ratio (mixing ratio) of the hydroxy group-containing compound (2) with respect to the hydrophilic copolymer in the surface lubricious layer is also measured by the same method as described in the above <First Aspect>.

[Method for Manufacturing Medical Device]

A method for manufacturing the medical device is not particularly limited except that the surface lubricious layer is formed using the hydrophilic copolymer and the hydroxy group-containing compound (2), and a known method can be applied in the same manner or after appropriate modification. For example, preferred is a method in which a coating liquid is prepared by dissolving the hydrophilic copolymer and the hydroxy group-containing compound (2) in a solvent, and is coated onto a substrate layer of the medical device to form a surface lubricious layer. That is, the disclosure here also provides a method for manufacturing the medical device, the method including coating a coating liquid containing the hydroxy group-containing compound (2) and the hydrophilic copolymer onto the substrate layer to form the surface lubricious layer. With such a method, the lubricating property and the durability (lubrication retaining property) can be imparted to the surface of the medical device. Since the details of the method are the same as those in [Method for Manufacturing Medical Device] in the above <First Aspect>, description thereof is omitted here.

<Third Aspect>

The third aspect relates to a medical device including: a substrate layer; and a surface lubricious layer formed on at least a part of the substrate layer, and containing a hydroxy group-containing compound (hydroxy group-containing compound (3)) selected from the group consisting of glycerol, a glycerol condensate, partially esterified products thereof, and partially etherified products thereof, and soluble in water, and a hydrophilic copolymer containing a structural unit derived from a polymerizable monomer (A) having a sulfobetaine structure, a structural unit derived from a polymerizable monomer (B) having at least one group selected from the group consisting of a sulfonic acid group ($-SO_3H$), a sulfuric acid group ($-OSO_3H$), a sulfurous acid group ($-OSO_2H$), and salt groups thereof, and a structural unit derived from a polymerizable monomer (C) having a photoreactive group.

[Substrate Layer (Substrate)]

Since the substrate layer used in this aspect is the same as [Substrate Layer (Substrate)] in the above <First Aspect>, description thereof is omitted here.

[Surface Lubricious Layer]

The surface lubricious layer used in this aspect is mainly different from that in the first aspect in that the water-retaining material is not the hydroxy group-containing compound (1), but the hydroxy group-containing compound (3). Therefore, in the following, only matters different from [Surface Lubricious Layer] in the above <First Aspect> will be described. Therefore, matters not described below are understood to be the same as those in [Surface Lubricious Layer] in the above <First Aspect>.

In this aspect, the surface lubricious layer may be directly disposed above the substrate layer. Alternatively, another layer (for example, an adhesive layer) may be provided between the surface lubricious layer and the substrate layer as long as another layer does not influence functions and effects disclosed here. Note that a preferred embodiment in a case where an adhesive layer is provided between the surface lubricious layer and the substrate layer will be described in <Third Aspect (Embodiment Including Adhesive Layer)> described later.

(Hydroxy Group-Containing Compound (3))

The hydroxy group-containing compound (3) is a hydroxy group-containing compound that is selected from the group consisting of glycerol, a glycerol condensate, partially esterified products thereof, and partially etherified products thereof, and is soluble in water. That is, the hydroxy group-containing compound (3) is a hydroxy group-containing compound that is selected from the group consisting of glycerol, a partially esterified product of glycerol, a partially etherified product of glycerol, a glycerol condensate, a partially esterified product of the glycerol condensate, and a partially etherified product of the glycerol condensate, and is soluble in water.

The glycerol condensate is a compound represented by the following formula, and in the formula, n is a number of 2 or more.

[Chem. 10]

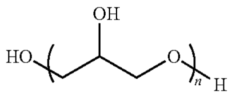

Examples of the glycerin condensate include diglycerol (glycerol dimer, in the above formula, n=2), triglycerol (glycerol trimer, in the above formula, n=3), and polyglycerin (in the above formula, n is 4 or more).

The partially esterified product of glycerol refers to a compound obtained by substituting one or two hydroxy groups (—OH) among three hydroxy groups contained in glycerol with —OC(═O)R (wherein R represents a monovalent hydrocarbon group) or —OS(═O)$_2$R (wherein R represents a monovalent hydrocarbon group). That is, the partially esterified product of glycerol has at least one hydroxy group. Similarly, the partially esterified product of the glycerol condensate refers to a compound obtained by substituting a part of hydroxy groups (—OH) among a plurality of hydroxy groups contained in a glycerol condensate with —OC(═O)R (wherein R represents a monovalent hydrocarbon group) or —OS(—O)$_2$R (wherein R represents a monovalent hydrocarbon group). That is, the partially esterified product of the glycerol condensate has at least one hydroxy group.

The partially etherified product of glycerol refers to a compound obtained by substituting one or two hydroxy groups (—OH) among three hydroxy groups contained in glycerol with —OR (wherein R represents a monovalent hydrocarbon group). That is, the partially etherified product of glycerol has at least one hydroxy group. Similarly, the partially etherified product of the glycerol condensate refers to a compound obtained by substituting a part of hydroxy groups (—OH) among a plurality of hydroxy groups contained in the glycerol condensate with —OR (wherein R represents a monovalent hydrocarbon group). That is, the partially etherified product of the glycerol condensate has at least one hydroxy group.

Examples of the monovalent hydrocarbon group include those described in (Hydroxy Group-Containing Compound (1)) in the above <First Aspect>.

The hydroxy group-containing compound (3) is a hydroxy group-containing compound soluble in water among the hydroxy group-containing compounds described above. That is, the hydroxy group-containing compound (3) is a hydroxy group-containing compound that is dissolved by an amount of 0.001 g or more in 100 mL of distilled water under a condition of room temperature (23° C.), among the hydroxy group-containing compounds described above.

An upper limit of a molecular weight of the hydroxy group-containing compound (3) is not particularly limited, and is preferably 10,000 or less, more preferably 5,000 or less, still more preferably 2,000 or less, even more preferably 1,000 or less, and particularly preferably 500 or less. A lower limit of the molecular weight of the hydroxy group-containing compound (3) is not particularly limited, and is, for example, 50 or more. Note that when a structure of the hydroxy group-containing compound (3) is specified, the molecular weight of the compound is a molecular weight calculated based on the structure. Alternatively, when the structure of the compound is not specified, the molecular weight is a weight average molecular weight (Mw) measured in terms of polyethylene glycol by gel permeation chromatography (GPC).

Examples of glycerol, the glycerol condensate, the partially esterified products thereof, and the partially etherified products thereof include glycerol, diglycerol, triglycerol, polyglycerin, a glycerin fatty acid ester, a polyglycerin fatty acid ester, 1,3-diethoxy-2-propanol, a polyoxypropylene glyceryl ether, a polyoxybutylene polyoxyethylene polyoxypropylene glyceryl ether, a polyoxyethylene polyoxypropylene glyceryl ether, a polyoxypropylene polyglyceryl ether, a polyoxyethylene polyglyceryl ether, and a polyoxyethylene glyceryl ether. These materials may be used alone or in combination of two or more types thereof.

That is, in a preferred embodiment of this aspect, the hydroxy group-containing compound (3) is a hydroxy group-containing compound that is selected from the group consisting of glycerol, diglycerol, triglycerol, polyglycerin, a glycerin fatty acid ester, a polyglycerin fatty acid ester, 1,3-diethoxy-2-propanol, a polyoxypropylene glyceryl ether, a polyoxybutylene polyoxyethylene polyoxypropylene glyceryl ether, a polyoxyethylene polyoxypropylene glyceryl ether, a polyoxypropylene polyglyceryl ether, a polyoxyethylene polyglyceryl ether, and a polyoxyethylene glyceryl ether, and is soluble in water.

From the viewpoint of further improving the lubricating property and the durability (lubrication retaining property), the hydroxy group-containing compound (3) is preferably a compound having two or more hydroxy groups (—OH), and more preferably a compound having 3 to 4 hydroxy groups (—OH). Alternatively, from the viewpoint of further improving the lubricating property and the durability (lubrication retaining property), the hydroxy group-containing compound (3) is preferably a compound having 2 or 3 carbon atoms between oxygen atoms. From the above viewpoint, the hydroxy group-containing compound (3) is more preferably at least one hydroxy group-containing compound that is selected from the group consisting of glycerol, diglycerol, triglycerol, and polyglycerin, and is soluble in water, and particularly preferably glycerol or diglycerol.

As the hydroxy group-containing compound (3), either a synthetic product or a commercially available product may be used. The commercially available product is available from Sigma-Aldrich Co. LLC. and the like.

In the surface lubricious layer, an abundance ratio (mixing ratio) of the hydroxy group-containing compound (3) with respect to the hydrophilic copolymer is not particularly limited. In the surface lubricious layer, for the abundance ratio (mixing ratio) of the hydroxy group-containing compound (3) with respect to the hydrophilic copolymer, the hydrophilic copolymer is preferably 0.1 parts by weight or more, more preferably 0.5 parts by weight or more, still more preferably 1 part by weight or more, and particularly preferably 2 parts by weight or more, with respect to 1 part by weight of the hydroxy group-containing compound (3). In the surface lubricious layer, for the abundance ratio (mixing ratio) of the hydroxy group-containing compound (3) with respect to the hydrophilic copolymer, the hydrophilic copolymer is preferably 1,000 parts by weight or less, more preferably 100 parts by weight or less, still more preferably 50 parts by weight or less, and particularly preferably 20 parts by weight or less, with respect to 1 part by weight of the hydroxy group-containing compound (3).

With such an abundance ratio (mixing ratio), the water retention effect of the hydroxy group-containing compound (3) and the lubricating property of the hydrophilic copolymer can be exhibited in a good balance. Note that when the surface lubricious layer contains two or more types of the hydroxy group-containing compounds (3), the above “1 part by weight” means that a total amount of these hydroxy group-containing compounds (3) is 1 part by weight. Similarly, when the surface lubricious layer contains two or more types of hydrophilic copolymers, the above amount (part by weight) of the hydrophilic copolymers means a total amount of these hydrophilic copolymers. The above abundance ratio (mixing ratio) is substantially equal to a ratio of a total charge amount (weight) of the hydrophilic copolymers with respect to a total charge amount (weight) of the hydroxy group-containing compounds (3) during formation of the surface lubricious layer.

Here, the presence and the ratio of the structural unit derived from each polymerizable monomer in the hydrophilic copolymer and the presence of the hydroxy group-containing compound (3) in the surface lubricious layer can be confirmed by the same method as described in the above <First Aspect>. The abundance ratio (mixing ratio) of the hydroxy group-containing compound (3) with respect to the hydrophilic copolymer in the surface lubricious layer is also measured by the same method as described in the above <First Aspect>.

[Method for Manufacturing Medical Device]

A method for manufacturing the medical device is not particularly limited except that the surface lubricious layer is formed using the hydrophilic copolymer and the hydroxy group-containing compound (3), and a known method can be applied in the same manner or after appropriate modification. For example, preferred is a method in which a coating liquid is prepared by dissolving the hydrophilic copolymer and the hydroxy group-containing compound (3) in a solvent, and is coated onto a substrate layer of the medical device to form a surface lubricious layer. That is, the disclosure here also provides a method for manufacturing the medical device, the method including coating a coating liquid containing the hydroxy group-containing compound (3) and the hydrophilic copolymer onto the substrate layer to form the surface lubricious layer. With such a method, the lubricating property and the durability (lubrication retaining property) can be imparted to the surface of the medical device.

Since the details of the method are the same as those in [Method for Manufacturing Medical Device] in the above <First Aspect>, description thereof is omitted here.

First Aspect (Embodiment Including Adhesive Layer)

In the above <First Aspect>, as shown in FIGS. 3 and 4, the adhesive layer 3 may be provided between the surface lubricious layer 2 and the substrate layer 1. A component of the adhesive layer 3 is not particularly limited, and it is preferable to use a hydrophilic copolymer having the same monomer composition as that of the hydrophilic copolymer used for the surface lubricious layer 2. That is, in one embodiment, an adhesive layer containing a hydrophilic copolymer containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group is formed on at least a part of the substrate layer and between the substrate layer and the surface lubricious layer. A medical device according to this embodiment includes: a substrate layer; an adhesive layer formed on at least a part of the substrate layer, and containing a hydrophilic copolymer (1) containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group; and a surface lubricious layer formed on at least a part of the adhesive layer, and containing the hydroxy group-containing compound (1), and a hydrophilic copolymer (2) containing a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group.

[Substrate Layer (Substrate)]

Since the substrate layer used in this embodiment is the same as [Substrate Layer (Substrate)] in the above <First Aspect>, description thereof is omitted here.

[Adhesive Layer (Hydrophilic Copolymer (1))]

The adhesive layer is formed on at least a part of the substrate layer, and contains the hydrophilic copolymer (1) containing the structural unit derived from the polymerizable monomer (A') having a sulfobetaine structure (structural unit (A')), the structural unit derived from the polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof (structural unit (B')), and the structural unit derived from the polymerizable monomer (C') having a photoreactive group (structural unit (C')). Here, the adhesive layer is not necessarily formed on the entire surface of the substrate layer. For example, the adhesive layer may be formed on a surface portion (a part) of the substrate layer to be in contact with a body fluid.

The hydrophilic copolymer (1) contained in the adhesive layer contains the structural unit (the structural unit (A')) derived from the polymerizable monomer (A') (hereinafter, also referred to as a “monomer A'”) having a sulfobetaine structure, the structural unit (the structural unit (B')) derived from the polymerizable monomer (B') (hereinafter, also referred to as a “monomer B'”) having at least one group selected from the group consisting of a sulfonic acid group (—$SO_3H$), a sulfuric acid group (—$OSO_3H$), a sulfurous acid group (—$OSO_2H$), and salt groups thereof, and the structural unit (the structural unit (C')) derived from the polymerizable monomer (C') (hereinafter, also referred to as a “monomer C'”) having a photoreactive group. The hydrophilic copolymer (1) (hence, the adhesive layer) can exhibit a sufficient lubricating property and sufficient durability (lubrication retaining property). The hydrophilic copolymer (1) has good bondability (adhesiveness) to the substrate layer, and the hydrophilic copolymer (2) and the hydroxy group-containing compound (1) in the surface lubricious layer described later. A mechanism by which such an effect is produced is not completely unclear, but the following mechanism is theorized. The photoreactive group contained in the structural unit derived from the monomer C generates reactive species by the irradiation with the active energy rays, and reacts with the surface of the substrate layer and the hydrophilic copolymer (2) or the hydroxy group-containing compound (1) in the surface lubricious layer described later to form a chemical bond.

Therefore, the adhesive layer containing the hydrophilic copolymer (1) is firmly immobilized on the substrate layer, and firmly immobilizes the surface lubricious layer, so that the durability (lubrication retaining property) is excellent. Note that the above mechanism is theory, and the invention is not limited to the above theory.

In this aspect, another layer may be provided between the adhesive layer and the substrate layer as long as another layer does not influence functions and effects disclosed here, and preferably, the adhesive layer is directly disposed above the substrate layer.

A thickness of the adhesive layer is not particularly limited. From the viewpoints of the adhesiveness to the substrate layer, the adhesiveness to the surface lubricious layer, the lubricating property, and the like, the thickness (dry film thickness) of the adhesive layer is preferably 0.1 m to 100 μm, and more preferably 0.2 μm to 50 μm.

Hereinafter, each polymerizable monomer constituting the hydrophilic copolymer (1) contained in the adhesive layer according to this aspect will be described.

(Polymerizable Monomer (A'))

The hydrophilic copolymer (1) contains the structural unit derived from the polymerizable monomer (A') having a sulfobetaine structure (structural unit (A')). Here, the structural unit (A') constituting the hydrophilic copolymer (1) may be one type alone or a combination of two or more types. That is, the structural unit (A') may be constituted by only one type of structural unit (A'), or may be constituted by two or more types of structural units (A'). Note that a plurality of structural units (A') may be present in a block shape or in a random shape.

The polymerizable monomer (A') (monomer A') is a polymerizable monomer having a sulfobetaine structure. The sulfobetaine structure included in the structural unit derived from the monomer A' is excellent in effect of imparting the lubricating property. Therefore, the hydrophilic copolymer (1) having the structural unit derived from the monomer A' is considered to be excellent in lubricating property. Note that the above is theory, and the invention is not limited to the above theory.

Since a specific definition and examples of the polymerizable monomer (A') are the same as those (of Polymerizable Monomer (A)) in the above <First Aspect>, description thereof is omitted here.

From the viewpoint of further improving the lubricating property and the durability (lubrication retaining property), the monomer A' is preferably a compound represented by the above formula (1). That is, in a preferred embodiment, the polymerizable monomer (A') is represented by the above formula (1).

(Polymerizable Monomer (B'))

The hydrophilic copolymer (1) contains the structural unit derived from the polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof (the structural unit (B')). Here, the structural unit (B') constituting the hydrophilic copolymer (2) may be one type alone or a combination of two or more types. That is, the structural unit (B') may be constituted by only one type of structural unit (B'), or may be constituted by two or more types of structural units (B'). Note that a plurality of structural units (B') may be present in a block shape or in a random shape.

The polymerizable monomer (B') (monomer B') is a polymerizable monomer having at least one group selected from the group consisting of a sulfonic acid group (—$SO_3H$), a sulfuric acid group (—$OSO_3H$), a sulfurous acid group (—$OSO_2H$), and salt groups thereof. By introducing such a group, anionization occurs in an aqueous solvent, and electrostatic repulsion occurs between the hydrophilic copolymers. As a result, an electrostatic interaction between the sulfobetaine structures and a hydrophobic interaction between the photoreactive groups in the hydrophilic copolymers are reduced. Therefore, the solvent solubility of the copolymer (particularly the solubility in water, a lower alcohol, or a mixed solvent of water and a lower alcohol) is improved. This improving effect is particularly remarkable when the photoreactive group of the monomer C' is a benzophenone group. Since the benzophenone group has a plurality of aromatic rings, the benzophenone groups are likely to associate with each other by a π-π interaction, which makes the polymers containing the benzophenone group to aggregate and insolubilize. Therefore, it is considered that by introducing the structural unit derived from the polymerizable monomer (B'), the electrostatic repulsion occurs as described above, and the association between the benzophenone groups is reduced, and thus the solubility or dispersibility of the polymer is rapidly improved. Note that the above mechanism is theory, and the invention is not limited to the above theory. Alternatively, even when the monomer C' has an ester group, the above improving effect can be obtained satisfactorily.

Since a specific definition and examples of the polymerizable monomer (B') are the same as those (of Polymerizable Monomer (B)) in the above <First Aspect>, description thereof is omitted here.

Among these, from the viewpoint of further improving the solvent solubility, the polymerizable monomer (B') is preferably a compound represented by the following formula (2), (3), or (4), and more preferably a compound represented by the following formula (2). That is, in a preferred embodiment, the polymerizable monomer (B') is represented by the following formula (2), (3), or (4). In a more preferred embodiment, the polymerizable monomer (B') is represented by the following formula (2).

Note that since definitions of the following formulas (2) to (4) are the same as those (of Polymerizable Monomer (B)) described above, description thereof is omitted here.

[Chem. 11]

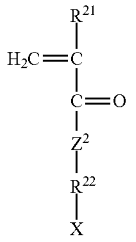

(2)

In the above formula (2), $R^{21}$ represents a hydrogen atom or a methyl group, $Z^2$ represents an oxygen atom or —NH—, $R^{22}$ represents a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof.

[Chem. 12]

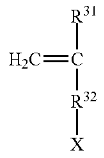

(3)

In the above formula (3), $R^{31}$ represents a hydrogen atom or a methyl group, $R^{32}$ represents a single bond or a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof.

[Chem. 13]

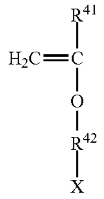

(4)

In the above formula (4), $R^{41}$ represents a hydrogen atom or a methyl group, $R^{42}$ represents a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof.

(Polymerizable Monomer (C'))

The hydrophilic copolymer (1) contains the structural unit derived from the polymerizable monomer (C') having a photoreactive group (structural unit (C')). Here, the structural unit (C') constituting the hydrophilic copolymer (2) may be one type alone or a combination of two or more types. That is, the structural unit (C') may be constituted by only one type of structural unit (C'), or may be constituted by two or more types of structural units (C'). Note that a plurality of structural units (C') may be present in a block shape or in a random shape.

The polymerizable monomer (C') (monomer C') is a polymerizable monomer having a photoreactive group. With the polymerizable monomer C', the surface lubricious layer containing the hydrophilic copolymer (2) can be firmly immobilized on the substrate layer via the adhesive layer. Therefore, the medical device can exhibit sufficient durability (lubrication retaining property).

Since a specific definition and examples of the polymerizable monomer (C') are the same as those (of Polymerizable Monomer (C)) in the above <First Aspect>, description thereof is omitted here.

From the viewpoints of forming a covalent bond with the surface lubricious layer and firmly immobilizing the surface lubricious layer on the substrate layer, the photoreactive group of the polymerizable monomer (C') is preferably the same as the photoreactive group of the polymerizable monomer (C) in the hydrophilic copolymer (2) contained in the surface lubricious layer. That is, in a preferred embodiment, the polymerizable monomer (C') has a group having a benzophenone structure.

The hydrophilic copolymer (1) may contain a structural unit derived from a polymerizable monomer other than the above monomer A', monomer B', and monomer C' (hereinafter, also referred to as "other monomer") in a range that does not impair the described effects. In the hydrophilic copolymer (1), a content of the structural unit derived from the other monomer is preferably less than 10 mol %, more preferably less than 5 mol %, and still more preferably less than 1 mol % (lower limit: more than 0 mol %), with respect to 100 mol %, which is the total of the structural units derived from all the monomers. Note that when the structural unit derived from the other monomer is constituted by two or more types of structural units, a composition of the above structural unit derived from the other monomer occupies a ratio (molar ratio (mol %)) of all the structural units derived from the other monomer with respect to the total of the structural units derived from all the monomers (100 mol %).

Preferably, the hydrophilic copolymer (1) is constituted by the monomer A', the monomer B', and the monomer C' (the composition of the other monomer=0 mol %). Note that the mol % is substantially equivalent to a ratio of a charge amount (mol) of the other monomer with respect to the total charge amount (mol) of all the monomers in the production of the polymer.

A terminal end of the hydrophilic copolymer (1) is not particularly limited, and is appropriately defined depending on types of raw materials to be used, and is usually a hydrogen atom. A structure of the copolymer is not particularly limited, and may be any of a random copolymer, an alternating copolymer, a periodic copolymer, and a block copolymer.

A weight average molecular weight (Mw) of the hydrophilic copolymer (1) is preferably several thousand to several million, more preferably 1,000 to 1,000,000, and particularly preferably 5,000 to 500,000. In the disclosure here, the "weight average molecular weight" shall be a value measured by gel permeation chromatography (GPC) using polyethylene glycol as a standard substance.

[Method for Manufacturing Hydrophilic Copolymer (1)]

A method for manufacturing the hydrophilic copolymer (1) is not particularly limited, and specific description thereof is the same as that in [Method for Manufacturing Hydrophilic Copolymer] in the above <First Aspect>, and thus description thereof is omitted here.

The presence and the ratio of the structural unit derived from each polymerizable monomer in the hydrophilic copolymer (1) in the adhesive layer can be confirmed by, for example, analyzing a peak intensity of a group contained in each structural unit using a known method such as IR, NMR, and pyrolysis GC/MS. In the present description, the presence and the ratio of the structural unit derived from each polymerizable monomer in the hydrophilic copolymer (1) in the adhesive layer are measured according to the following method.

(Method for Detecting and Measuring Presence and Ratio of Structural Unit Derived from Each Polymerizable Monomer in Hydrophilic Copolymer (1) in Adhesive Layer)

With the surface of the medical device swollen with heavy water or the like, precision diagonal cutting is performed on the medical device to prepare an inclined cross section of the medical device. From the cross section, an adhesive layer portion located near the substrate of the medical device is cut, and a material of the adhesive layer portion is collected. Next, the material of the adhesive layer portion is filled into a sample tube for solid NMR without any gap to prepare a sample, and 1H-NMR or 13C-NMR measurement is performed. Here, peaks specific to a site (for example, a sulfobetaine structure) specific to the structural unit (A), a site (for example, a salt of a sulfonic acid group) specific to the structural unit (B), and a site (for example, a benzophenone group) specific to the structural unit (C) are to be confirmed, and when these peaks are confirmed, it is determined that the corresponding structural units are present in the sample. A concentration of the site (for example, the sulfobetaine structure) specific to the structural unit (A) (concentration (a)), a concentration of the site (for example, the salt of the sulfonic acid group) specific to the structural unit (B) (concentration (b)), and a concentration of the site (for example, the benzophenone group) specific to the structural unit (C) (concentration (c)) are measured. A ratio of each of the concentrations (a), (b), and (c) is regarded as an abundance ratio of the structural unit derived from each polymerizable monomer in the hydrophilic copolymer (1). Note that an analyzer and measurement conditions used in the above measurement are as follows.

Analyzer: ECZ500R, NM080006, manufactured by JEOL Ltd.

Measurement conditions: heavy water or a mixed liquid of heavy water and a heavy solvent of a lower alcohol.

[Surface Lubricious Layer]

The surface lubricious layer in this embodiment is formed on at least a part of the adhesive layer, and contains the hydroxy group-containing compound (1), and the hydrophilic copolymer (2) containing the structural unit derived from the polymerizable monomer (A) having a sulfobetaine structure, the structural unit derived from the polymerizable monomer (B) having at least one group selected from the group consisting of a sulfonic acid group ($-SO_3H$), a sulfuric acid group ($-OSO_3H$), a sulfurous acid group ($-OSO_2H$), and salt groups thereof, and the structural unit derived from the polymerizable monomer (C) having a photoreactive group.

Since the hydrophilic copolymer (2) used in this embodiment is the same as (Hydrophilic Copolymer) in the above <First Aspect>, description thereof is omitted here.

The hydrophilic copolymer (2) contained in the surface lubricious layer may have a structure same as or different from that of the hydrophilic copolymer (1) contained in the adhesive layer. From the viewpoint of immobilization strength (hence durability) between the adhesive layer and the surface lubricious layer, the hydrophilic copolymer (1) and the hydrophilic copolymer (2) preferably have the same structure. In the above embodiment, only one process is required to manufacture the hydrophilic copolymer, and a use amount of the hydrophilic copolymer increases, therefore it is particularly preferable from the viewpoints of the number of production steps during mass production and a cost of products. Here, "the hydrophilic copolymer (1) and the hydrophilic copolymer (2) have the same structure" means that types of the structural units (A'), (B'), (C'), and, if present, a structural unit derived from another monomer constituting the hydrophilic copolymer (1) are all the same as those of the structural units (A), (B), (C), and, if present, a structural unit derived from another monomer constituting the hydrophilic copolymer (2), respectively (the hydrophilic copolymers (1) and (2) are constituted by the same structural units). From the viewpoints of further improving the immobilization strength (hence durability) between the adhesive layer and the surface lubricious layer, productivity, and the like, it is preferable that the types and compositions (content ratio (molar ratio)) of the structural units constituting the hydrophilic copolymers (1) and (2) are all the same (the hydrophilic copolymers (1) and (2) are constituted by the same structural units and the same compositions).

In the surface lubricious layer, an abundance ratio (mixing ratio) of the hydroxy group-containing compound (1) with respect to the hydrophilic copolymer (2) is not particularly limited. In the surface lubricious layer, for the abundance ratio (mixing ratio) of the hydroxy group-containing compound (1) with respect to the hydrophilic copolymer (2), the hydrophilic copolymer (2) is preferably 0.1 parts by weight or more, more preferably 0.5 parts by weight or more, still more preferably 1 part by weight or more, and particularly preferably 2 parts by weight or more, with respect to 1 part by weight of the hydroxy group-containing compound (1). In the surface lubricious layer, for the abundance ratio (mixing ratio) of the hydroxy group-containing compound (1) with respect to the hydrophilic copolymer (2), the hydrophilic copolymer (2) is preferably 1,000 parts by weight or less, more preferably 500 parts by weight or less, still more preferably 200 parts by weight or less, even more preferably 100 parts by weight or less, yet still more preferably 50 parts by weight or less, and particularly preferably 20 parts by weight or less, with respect to 1 part by weight of the hydroxy group-containing compound (1). With such an abundance ratio (mixing ratio), the water retention effect of the hydroxy group-containing compound (1) and the lubricating property of the hydrophilic copolymer (2) can be exhibited in a good balance. Note that when the surface lubricious layer contains two or more types of the hydroxy group-containing compounds (1), the above "1 part by weight" means that a total amount of these hydroxy group-containing compounds (1) is 1 part by weight. Similarly, when the surface lubricious layer contains two or more types of hydrophilic copolymers (2), the above amount (part by weight) of the hydrophilic copolymers (2) means a total amount of these hydrophilic copolymers (2). The above abundance ratio (mixing ratio) is substantially equal to a ratio of a total charge amount (weight) of the hydrophilic copolymers (2) with respect to a total charge amount (weight) of the hydroxy group-containing compounds (1) during formation of the surface lubricious layer.

[Method for Manufacturing Medical Device]

A method for manufacturing the medical device according to this embodiment is not particularly limited except that the adhesive layer is formed using the hydrophilic copolymer (1), and the surface lubricious layer is formed using the hydrophilic copolymer (2) and the hydroxy group-containing compound (1), and a known method can be applied in the same manner or after appropriate modification. For example, preferred is a method in which a coating liquid is prepared by dissolving the hydrophilic copolymer (1) in a solvent, and is coated on a substrate layer of the medical device to form an adhesive layer, and then a coating liquid is prepared by dissolving the hydrophilic copolymer (2) and the hydroxy group-containing compound (1) in a solvent, and is coated on the above adhesive layer to form a surface lubricious layer. With such a method, the lubricating property and the durability (lubrication retaining property) can be imparted to the surface of the medical device.

(Coating Step for Adhesive Layer)

In the above method, the solvent used for dissolving the hydrophilic copolymer (1) is preferably water, a lower alcohol, or a mixed solvent of water and a lower alcohol from the viewpoints of working safety (low toxicity) and solubility. Here, the lower alcohol refers to a primary alcohol having 1 to 3 carbon atoms, that is, methanol, ethanol, n-propanol, or isopropanol. The above lower alcohols may be used alone or in combination of two or more types thereof.

A concentration of the hydrophilic copolymer (1) in the coating liquid (1) is not particularly limited, and is preferably 0.01 wt % to 50 wt %, more preferably 0.05 wt % to 40 wt %, and still more preferably 0.1 wt % to 30 wt %. Within such a range, coatability of the coating liquid (1) is good, and the obtained adhesive layer has sufficient lubricating property and durability (lubrication retaining property). A uniform adhesive layer having a desired thickness can be easily obtained with single coating. Therefore, the hydrophilic copolymer (1) can form a strong and uniform chemical bond with the substrate layer by subsequent irradiation with active energy rays (immobilizing step for the adhesive layer). The range is also preferred in terms of production efficiency. Note that when the concentration of the hydrophilic copolymer (1) is less than 0.001 wt %, a sufficient amount of the hydrophilic copolymer (1) may not be immobilized on the surface of the substrate layer. When the concentration of the hydrophilic copolymer (1) is more than 50 wt %, the viscosity of the coating liquid (1) may become too high to obtain the adhesive layer having a uniform thickness. However, even when the concentration deviates from the above range, the coating liquid (1) can be sufficiently used as long as the described functions and effects are not influenced.

A coating amount of the coating liquid (1) is not particularly limited, and is preferably an amount that corresponds to the thickness of the above adhesive layer.

Before coating the coating liquid (1), the surface of the substrate layer may be treated in advance by an ultraviolet irradiation treatment, a plasma treatment, a corona discharge treatment, a flame treatment, an oxidation treatment, a silane coupling treatment, a phosphoric acid coupling treatment, or the like. When the solvent of the coating liquid (1) is only water, it is difficult to coat the coating liquid (1) to the surface of the hydrophobic substrate layer, and the surface of the substrate layer is made hydrophilic by performing a plasma treatment on the surface of the substrate layer. Accordingly, wettability of the coating liquid (1) to the surface of the substrate layer is improved, and a uniform adhesive layer can be formed. By applying the above treatment to the surface of the substrate layer, which does not have any C—H bond of a metal, a fluorine resin, or the like, a covalent bond with the photoreactive group of the hydrophilic copolymer (1) can be formed.

A method for coating the coating liquid (1) onto the surface of the substrate layer is not particularly limited, and a known method in the related art can be applied, such as a coating printing method, an immersion method (dipping method, dip coating method), a spraying method (spray method), a spin coating method, and a mixed solution impregnated sponge coating method. Among these, the immersion method (dipping method, dip coating method) is preferred.

(Drying Step for Adhesive Layer)

It is preferable that, after coating the coating liquid (1) containing the hydrophilic copolymer (1) onto the surface of the substrate layer as described above, the substrate layer is taken out from the coating liquid (1), and a coating film is dried. Drying conditions are not particularly limited as long as the solvent can be removed from the coating film, and a warm air treatment may be performed using a dryer or the like, or natural drying may be performed. A pressure condition during the drying is also not limited at all, and the drying may be performed under a normal pressure (atmospheric pressure), or under a pressure or a reduced pressure. As a drying unit (device), for example, an oven, a decompression dryer, or the like can be used, and in the case of natural drying, no drying unit (device) is particularly required.

(Immobilizing Step for Adhesive Layer)

The coating film after the drying step is irradiated with active energy rays. Accordingly, the photoreactive group in the coating film (the monomer C of the hydrophilic copolymer (1)) is activated, and a chemical bond is formed between the photoreactive group and an alkyl group (hydrocarbon group) contained in the substrate layer. More specifically, a case of a combination of the photoreactive group having a benzophenone structure and a resin (a material having a hydrocarbon group) constituting the substrate layer will be described. When the hydrophilic copolymer (1) has the photoreactive group having a benzophenone structure, two radicals are generated in the photoreactive group by irradiation with ultraviolet rays. One of these radicals abstracts the hydrogen atom from the alkyl group (hydrocarbon group) in the resin, and instead one radical is generated in the material. Then, the remaining radical in the photoreactive group and the radical generated in the material are bonded to each other, whereby a covalent bond is formed between the photoreactive group of the hydrophilic copolymer (1) in the adhesive layer and the material (resin) in the substrate layer. With such a chemical bond, the adhesive layer containing the hydrophilic copolymer (1) is firmly immobilized on the substrate layer. Therefore, the adhesive layer can exhibit the sufficient durability (lubrication retaining property).

Examples of the active energy rays include ultraviolet rays (UV), electron beams, and gamma rays, and are preferably ultraviolet rays or electron beams, and more preferably ultraviolet rays in consideration of an influence on a human body. When the active energy rays are ultraviolet rays, a wavelength at which the photoreactive group can be activated can be appropriately selected as an irradiation wavelength. Specifically, a wavelength range of the ultraviolet rays is preferably 200 nm to 400 nm, and more preferably 220 nm to 390 nm. The irradiation with ultraviolet rays is preferably performed under a temperature condition of 10° C. to 100° C., and more preferably 20° C. to 80° C. An irradiation intensity of the ultraviolet rays is not particularly limited, and is preferably 1 mW/cm2 to 5000 mW/cm2, more preferably 1 mW/cm2 to 1000 mW/cm2, and still more preferably 10 mW/cm2 to 1000 mW/cm2. An integrated light amount of the ultraviolet rays (an integrated light amount of the ultraviolet rays on the adhesive layer before coating the surface lubricious layer) is not particularly limited, and is preferably 50 mJ/cm2 to 100,000 mJ/cm2, more preferably 100 mJ/cm2 to 100,000 mJ/cm2, still more preferably 100 mJ/cm2 to 75,000 mJ/cm2, and particularly preferably 500 mJ/cm2 to 50,000 mJ/cm2. Examples of a device for emitting the ultraviolet rays include a high-pressure mercury lamp, a low-pressure mercury lamp, a metal halide lamp, a xenon lamp, and a halogen lamp. Note that a method for emitting the active energy rays is not particularly limited, and the irradiation may be performed from one direction, or from multiple directions, or the irradiation may be performed while rotating an irradiation source, or while rotating an object to be irradiated (one in which the coating film of the adhesive layer is formed on the substrate layer).

After performing the above irradiation with active energy rays, the coating film may be washed with a solvent (for example, the solvent used for preparing the coating liquid (1)) to remove the unreacted hydrophilic copolymer (1).

The immobilization of the coating film (adhesive layer) on the substrate layer can be confirmed by using a known analytical method such as FT-IR, XPS, and TOF-SIMS. For example, the immobilization can be confirmed by performing FT-IR measurement before and after the irradiation with active energy rays, and comparing ratios of a peak of bonds formed by the irradiation with active energy rays with respect to a peak of invariant bonds.

With the above method, in the medical device according to the disclosure here, the adhesive layer containing the hydrophilic copolymer (1) is formed on the surface of the substrate layer.

(Coating Step for Surface Lubricious Layer)

Here, the hydrophilic copolymer (2) and the hydroxy group-containing compound (1) are dissolved in a solvent to prepare the coating liquid (2), and the coating liquid (2) is coated onto the adhesive layer formed as above. In the above method, the solvent used for dissolving the hydrophilic copolymer (2) and the hydroxy group-containing compound (1) is preferably water, a lower alcohol, or a mixed solvent of water and a lower alcohol from the viewpoints of working safety (low toxicity) and solubility. Here, the lower alcohol refers to a primary alcohol having 1 to 3 carbon atoms, that is, methanol, ethanol, n-propanol, or isopropanol. The above lower alcohols may be used alone or in combination of two or more types thereof. Here, the hydrophilic copolymer (2) and the hydroxy group-containing compound (1) may be added to the solvent together, may be sequentially added to the same solvent (the hydrophilic copolymer (2) and then the hydroxy group-containing compound (1) or the hydroxy group-containing compound (1) and then the hydrophilic copolymer (2)), or the hydrophilic copolymer (2) and the hydroxy group-containing compound (1) may be dissolved in different solvents and then mixed with each other. Note that when the hydrophilic copolymer (2) and the hydroxy group-containing compound (1) may be dissolved in different solvents, the solvents may be the same or different from each other, and are preferably the same in consideration of ease of operation and the like.

A concentration of the hydrophilic copolymer (2) in the coating liquid (2) is not particularly limited, and is preferably more than 0.01 wt % and less than 50 wt %, more preferably 0.1 wt % to 20 wt %, and particularly preferably 0.1 wt % to 10% wt %. Within such a range, coatability of the coating liquid (2) is good, and a strong and uniform chemical bond can be formed with the adhesive layer (hydrophilic copolymer (1)) or the hydroxy group-containing compound (1) by subsequent irradiation with active energy rays (immobilizing step for surface lubricious layer) (therefore, the surface lubricious layer has excellent lubricating property and durability (lubrication retaining property)). The range is also preferred in terms of production efficiency. A concentration of the hydroxy group-containing compound (1) in the coating liquid (2) is not particularly limited, and is preferably more than 0.001 wt % and less than 1 wt %, more preferably 0.005 wt % to 0.7 wt %, and still more preferably 0.01 wt % to 0.5 wt %. Within such a range, the coatability of the coating liquid (2) is good, and the obtained surface lubricious layer can exhibit a sufficient water retention effect (therefore, the surface lubricious layer can exhibit excellent lubricating property even under a high load condition). Here, a mixing ratio of the hydrophilic copolymer (2) with respect to the hydroxy group-containing compound (1) in the coating liquid (2) is not particularly limited, and is preferably the same mixing ratio as described in the section of Surface Lubricious Layer.

A method for coating the coating liquid (2) onto the surface of the adhesive layer is not particularly limited, and a known method in the related art can be applied, such as a coating printing method, an immersion method (dipping method, dip coating method), a spraying method (spray method), a spin coating method, and a mixed solution impregnated sponge coating method. Among these, the immersion method (dipping method, dip coating method) is preferred.

(Drying Step for Surface Lubricious Layer)

As described above, it is preferable that, after immersing the substrate layer on which the adhesive layer is formed in advance in the coating liquid (2), the substrate layer is taken out from the coating liquid (2) and a coating film is dried. Drying conditions are not particularly limited as long as the solvent can be removed from the coating film, and a warm air treatment may be performed using a dryer or the like, or natural drying may be performed. A pressure condition during the drying is also not limited at all, and the drying may be performed under a normal pressure (atmospheric pressure), or under a pressure or a reduced pressure. As a drying unit (device), for example, an oven, a decompression dryer, or the like can be used, and in the case of natural drying, no drying unit (device) is particularly required.

(Immobilizing Step for Surface Lubricious Layer)

The coating film after the drying step is irradiated with active energy rays. Accordingly, the photoreactive group of the hydrophilic copolymer (1) (monomer C) in the adhesive layer and the photoreactive group of the hydrophilic copolymer (2) (monomer C') in the surface lubricious layer are activated, and a chemical bond is formed between the photoreactive group of the hydrophilic copolymer (1) and the photoreactive group of the hydrophilic copolymer (2) and the hydroxy group-containing compound (1). For example, a case of a combination of the photoreactive group having a benzophenone structure of the hydrophilic copolymer (1) in the adhesive layer and the photoreactive group having a benzophenone structure of the hydrophilic copolymer (2) and the hydroxy group-containing compound (1) in the surface lubricious layer will be described. When the hydrophilic copolymers (1) and (2) have the photoreactive group having a benzophenone structure, two radicals are generated in the photoreactive group of each hydrophilic copolymer by irradiation with ultraviolet rays. One of these radicals abstracts the hydrogen atom from an alkyl group (hydrocarbon group) in the hydroxy group-containing compound (1), and instead one radical is generated in the hydroxy group-containing compound (1). Then, the remaining radical in the photoreactive group and the radical generated in the hydroxy group-containing compound (1) are bonded to each other, whereby a covalent bond is formed between the photoreactive group of the hydrophilic copolymer (1) in the adhesive layer and the hydroxy group-containing compound (1) in the surface lubricious layer, or between the photoreactive group of the hydrophilic copolymer (2) and the hydroxy group-containing compound (1) in the surface lubricious layer. With such a chemical bond between the hydroxy group-containing compound (1) and the hydrophilic copolymer in the adhesive layer or the surface lubricious layer, the surface lubricious layer is firmly immobilized on the adhesive layer, and at the same time, the hydroxy group-containing compound (1) is firmly immobilized in the surface lubricious layer. In addition, one of the two radicals of the hydrophilic copolymer (1) generated by the irradiation with the ultraviolet rays abstracts the hydrogen atom from an alkyl group (hydrocarbon group) in the hydrophilic copolymer (2), and instead one radical is generated in the hydrophilic copolymer (2). Then, the remaining radical in the photoreactive group of the hydrophilic copolymer (1) and the radical generated in the hydrophilic copolymer (2) are bonded to each other, whereby a covalent bond is formed between the photoreactive group of the hydrophilic copolymer (1) in the adhesive layer and the hydrophilic copolymer (2) in the surface lubricious layer. Similarly, one of the two radicals of the hydrophilic copolymer (2) generated by the irradiation with the ultraviolet rays abstracts the hydrogen atom from an alkyl group (hydrocarbon group) in the hydrophilic copolymer (1), and instead one radical is generated in the hydrophilic copolymer (1). Then, the remaining radical in the photoreactive group of the hydrophilic copolymer (2) and the radical generated in the hydrophilic copolymer (1) are bonded to each other, whereby a covalent bond is formed between the photoreactive group of the hydrophilic copolymer (1) in the adhesive layer and the hydrophilic copolymer (2) in the surface lubricious layer. With the chemical bond between the hydrophilic copolymer (1) in the adhesive layer and the hydrophilic copolymer (2) in the surface lubricious layer, the surface lubricious layer is also firmly immobilized on the adhesive layer. Therefore, the surface lubricious layer can effectively exhibit the water retention effect of the hydroxy group-containing compound (1) and can exhibit excellent lubricating property. The water retention effect of the hydroxy group-containing compound (1) can be maintained for a long period of time, and the excellent durability (lubrication retaining property) can also be exhibited.

Examples of the active energy rays include ultraviolet rays (UV), electron beams, and gamma rays, and are preferably ultraviolet rays or electron beams, and more preferably ultraviolet rays in consideration of an influence on a human body. When the active energy rays are ultraviolet rays, a wavelength at which the photoreactive group can be activated can be appropriately selected as an irradiation wavelength. Specifically, a wavelength range of the ultraviolet rays is preferably 200 nm to 400 nm, and more preferably 220 nm to 390 nm. The irradiation with ultraviolet rays is preferably performed under a temperature condition of 10° C. to 100° C., and more preferably 20° C. to 80° C. An irradiation intensity of the ultraviolet rays is not particularly limited, and is preferably 1 mW/cm2 to 5000 mW/cm2, more preferably 1 mW/cm2 to 1000 mW/cm2, and still more preferably 10 mW/cm2 to 1000 mW/cm2. An integrated light amount of the ultraviolet rays (an integrated light amount of the ultraviolet rays on the adhesive layer before coating the surface lubricious layer) is not particularly limited, and is preferably 50 mJ/cm2 to 100,000 mJ/cm2, more preferably 50 mJ/cm2 to 50,000 mJ/cm2, still more preferably 100 mJ/cm2 to 75,000 mJ/cm2, and particularly preferably 100 mJ/cm2 to 10,000 mJ/cm2. Examples of a device for emitting the ultraviolet rays include a high-pressure mercury lamp, a low-pressure mercury lamp, a metal halide lamp, a xenon lamp, and a halogen lamp. Note that a method for emitting the active energy rays is not particularly limited, and the irradiation may be performed from one direction, or from multiple directions, or the irradiation may be performed while rotating an irradiation source, or while rotating an object to be irradiated (one in which the coating film of the adhesive layer is formed on the substrate layer).

After performing the above irradiation with the active energy rays, the coating film may be washed with a solvent (for example, the solvent used for preparing the coating liquid (2)) to remove the unreacted hydrophilic copolymer (2).

The immobilization of the coating film (surface lubricious layer) on the adhesive layer can be confirmed by using a known analytical method such as FT-IR, XPS, and TOF-SIMS. For example, the immobilization can be confirmed by performing FT-IR measurement before and after the irradiation with active energy rays, and comparing ratios of a peak of bonds formed by the irradiation with active energy rays with respect to a peak of invariant bonds.

With the above method, in the medical device disclosed here, the surface lubricious layer containing the hydrophilic copolymer (2) and the hydroxy group-containing compound (1) is formed on the surface of the adhesive layer.

Second Aspect (Embodiment Including Adhesive Layer)

In the above <Second Aspect>, as shown in FIGS. 3 and 4, the adhesive layer 3 may be provided between the surface lubricious layer 2 and the substrate layer 1. A component of the adhesive layer 3 is not particularly limited, and it is preferable to use a hydrophilic copolymer having the same monomer composition as that of the hydrophilic copolymer used for the surface lubricious layer 2. That is, in one embodiment, an adhesive layer containing a hydrophilic copolymer containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group is formed on at least a part of the substrate layer and between the substrate layer and the surface lubricious layer. A medical device according to this embodiment includes: a substrate layer; an adhesive layer formed on at least a part of the substrate layer, and containing a hydrophilic copolymer (1) containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group; and a surface lubricious layer formed on at least a part of the adhesive layer, and containing the hydroxy group-containing compound (2), and a hydrophilic copolymer (2) containing a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group ($—OSO_2H$), and salt groups thereof, and a structural unit derived from a polymerizable monomer (C) having a photoreactive group.

[Substrate Layer (Substrate)]

Since the substrate layer used in this embodiment is the same as [Substrate Layer (Substrate)] in the above <First Aspect>, description thereof is omitted here.

[Adhesive Layer (Hydrophilic Copolymer (1))]

Since the adhesive layer (hydrophilic copolymer (1)) used in this embodiment is the same as [Adhesive Layer (Hydrophilic Copolymer (1))] in the above <First Aspect (Embodiment Including Adhesive Layer)>, description thereof is omitted here.

[Surface Lubricious Layer]

The surface lubricious layer in this embodiment is formed on at least a part of the adhesive layer, and contains the hydroxy group-containing compound (2), and the hydrophilic copolymer (2) containing the structural unit derived from the polymerizable monomer (A) having a sulfobetaine structure, the structural unit derived from the polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and the structural unit derived from the polymerizable monomer (C) having a photoreactive group. Since the hydrophilic copolymer (2) used in this embodiment is the same as (Hydrophilic Copolymer) in the above <First Aspect>, description thereof is omitted here.

The hydrophilic copolymer (2) contained in the surface lubricious layer may have a structure same as or different from that of the hydrophilic copolymer (1) contained in the adhesive layer. From the viewpoint of immobilization strength (hence durability) between the adhesive layer and the surface lubricious layer, the hydrophilic copolymer (1) and the hydrophilic copolymer (2) preferably have the same structure. In the above embodiment, only one process is required to manufacture the hydrophilic copolymer, and a use amount of the hydrophilic copolymer increases, therefore it is particularly preferable from the viewpoints of the number of production steps during mass production and a cost of products. Here, "the hydrophilic copolymer (1) and the hydrophilic copolymer (2) have the same structure" means that types of the structural units (A'), (B'), (C'), and, if present, a structural unit derived from another monomer constituting the hydrophilic copolymer (1) are all the same as those of the structural units (A), (B), (C), and, if present, a structural unit derived from another monomer constituting the hydrophilic copolymer (2), respectively (the hydrophilic copolymers (1) and (2) are constituted by the same structural units). From the viewpoints of further improving the immobilization strength (hence durability) between the adhesive layer and the surface lubricious layer, productivity, and the like, it is preferable that the types and compositions (content ratio (molar ratio)) of the structural units constituting the hydrophilic copolymers (1) and (2) are all the same (the hydrophilic copolymers (1) and (2) are constituted by the same structural units and the same compositions).

In the surface lubricious layer, an abundance ratio (mixing ratio) of the hydroxy group-containing compound (2) with respect to the hydrophilic copolymer (2) is not particularly limited. In the surface lubricious layer, for the abundance ratio (mixing ratio) of the hydroxy group-containing compound (2) with respect to the hydrophilic copolymer (2), the hydrophilic copolymer (2) is preferably 0.1 parts by weight or more, more preferably 0.5 parts by weight or more, still more preferably 1 part by weight or more, and particularly preferably 2 parts by weight or more, with respect to 1 part by weight of the hydroxy group-containing compound (2). In the surface lubricious layer, for the abundance ratio (mixing ratio) of the hydroxy group-containing compound (2) with respect to the hydrophilic copolymer (2), the hydrophilic copolymer (2) is preferably 1,000 parts by weight or less, more preferably 500 parts by weight or less, still more preferably 200 parts by weight or less, even more preferably 100 parts by weight or less, yet still more preferably 50 parts by weight or less, and particularly preferably 20 parts by weight or less, with respect to 1 part by weight of the hydroxy group-containing compound (2). With such an abundance ratio (mixing ratio), the water retention effect of the hydroxy group-containing compound (2) and the lubricating property of the hydrophilic copolymer (2) can be exhibited in a good balance. Note that when the surface lubricious layer contains two or more types of the hydroxy group-containing compounds (2), the above "1 part by weight" means that a total amount of these hydroxy group-containing compounds (2) is 1 part by weight. Similarly, when the surface lubricious layer contains two or more types of hydrophilic copolymers (2), the above amount (part by weight) of the hydrophilic copolymers (2) means a total amount of these hydrophilic copolymers (2). The above abundance ratio (mixing ratio) is substantially equal to a ratio of a total charge amount (weight) of the hydrophilic copolymers (2) with respect to a total charge amount (weight) of the hydroxy group-containing compounds (2) during formation of the surface lubricious layer.

[Method for Manufacturing Medical Device]

A method for manufacturing the medical device according to this embodiment is not particularly limited except that the adhesive layer is formed using the hydrophilic copolymer (1), and the surface lubricious layer is formed using the hydrophilic copolymer (2) and the hydroxy group-containing compound (2), and a known method can be applied in the same manner or after appropriate modification. For example, the medical device according to this embodiment can be manufactured in the same manner as the method described in [Method for Manufacturing Medical Device] in the above <First Aspect (Embodiment Including Adhesive Layer)>.

Third Aspect (Embodiment Including Adhesive Layer)

In the above <Third Aspect>, as shown in FIGS. 3 and 4, the adhesive layer 3 may be provided between the surface lubricious layer 2 and the substrate layer 1. A component of the adhesive layer 3 is not particularly limited, and it is preferable to use a hydrophilic copolymer having the same monomer composition as that of the hydrophilic copolymer used for the surface lubricious layer 2. That is, in one embodiment, an adhesive layer containing a hydrophilic copolymer containing a structural unit derived from a polymerizable monomer (A') having a sulfobetaine structure, a structural unit derived from a polymerizable monomer (B') having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C') having a photoreactive group is formed on at least a part of the substrate layer and between the substrate layer and the surface lubricious layer. A medical device according to this embodiment includes: a substrate layer; an adhesive layer formed on at least a part of the substrate layer, and containing a hydrophilic copolymer (1) containing a structural unit derived from a polymerizable monomer (A') having a sulfobetaine structure, a structural unit derived from a polymerizable monomer (B') having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C') having a photoreactive group; and a surface lubricious layer formed on at least a part of the adhesive layer, and containing the hydroxy group-containing compound (3), and a hydrophilic copolymer (2) containing a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group.

[Substrate Layer (Substrate)]

Since the substrate layer used in this embodiment is the same as [Substrate Layer (Substrate)] in the above <First Aspect>, description thereof is omitted here.

[Adhesive Layer (Hydrophilic Copolymer (1))]

Since the adhesive layer (hydrophilic copolymer (1)) used in this embodiment is the same as [Adhesive Layer (Hydrophilic Copolymer (1))] in the above <First Aspect (Embodiment Including Adhesive Layer)>, description thereof is omitted here.

[Surface Lubricious Layer]

The surface lubricious layer in this embodiment is formed on at least a part of the adhesive layer, and contains the hydroxy group-containing compound (3), and the hydrophilic copolymer (2) containing the structural unit derived from the polymerizable monomer (A) having a sulfobetaine structure, the structural unit derived from the polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and the structural unit derived from the polymerizable monomer (C) having a photoreactive group. Since the hydrophilic copolymer (2) used in this embodiment is the same as (Hydrophilic Copolymer) in the above <First Aspect>, description thereof is omitted here.

The hydrophilic copolymer (2) contained in the surface lubricious layer may have a structure same as or different from that of the hydrophilic copolymer (1) contained in the adhesive layer. From the viewpoint of immobilization strength (hence durability) between the adhesive layer and the surface lubricious layer, the hydrophilic copolymer (1) and the hydrophilic copolymer (2) preferably have the same structure. In the above embodiment, only one process is required to manufacture the hydrophilic copolymer, and a use amount of the hydrophilic copolymer increases, therefore it is particularly preferable from the viewpoints of the number of production steps during mass production and a cost of products. Here, "the hydrophilic copolymer (1) and the hydrophilic copolymer (2) have the same structure" means that types of the structural units (A'), (B'), (C'), and, if present, a structural unit derived from another monomer constituting the hydrophilic copolymer (1) are all the same as those of the structural units (A), (B), (C), and, if present, a structural unit derived from another monomer constituting the hydrophilic copolymer (2), respectively (the hydrophilic copolymers (1) and (2) are constituted by the same structural units). From the viewpoints of further improving the immobilization strength (hence durability) between the adhesive layer and the surface lubricious layer, productivity, and the like, it is preferable that the types and compositions (content ratio (molar ratio)) of the structural units constituting the hydrophilic copolymers (1) and (2) are all the same (the hydrophilic copolymers (1) and (2) are constituted by the same structural units and the same compositions).

In the surface lubricious layer, an abundance ratio (mixing ratio) of the hydroxy group-containing compound (3) with respect to the hydrophilic copolymer (2) is not particularly limited. In the surface lubricious layer, for the abundance ratio (mixing ratio) of the hydroxy group-containing compound (3) with respect to the hydrophilic copolymer (2), the hydrophilic copolymer (2) is preferably 0.1 parts by weight or more, more preferably 0.5 parts by weight or more, still more preferably 1 part by weight or more, and particularly preferably 2 parts by weight or more, with respect to 1 part by weight of the hydroxy group-containing compound (3). In the surface lubricious layer, for the abundance ratio (mixing ratio) of the hydroxy group-containing compound (3) with respect to the hydrophilic copolymer (2), the hydrophilic copolymer (2) is preferably 1,000 parts by weight or less, more preferably 500 parts by weight or less, still more preferably 200 parts by weight or less, even more preferably 100 parts by weight or less, yet still more preferably 50 parts by weight or less, and particularly preferably 20 parts by weight or less, with respect to 1 part by weight of the hydroxy group-containing compound (3). With such an abundance ratio (mixing ratio), the water retention effect of the hydroxy group-containing compound (3) and the lubricating property of the hydrophilic copolymer (2) can be exhibited in a good balance. Note that when the surface lubricious layer contains two or more types of the hydroxy group-containing compounds (3), the above "1 part by weight" means that a total amount of these hydroxy group-containing compounds (3) is 1 part by weight. Similarly, when the surface lubricious layer contains two or more types of hydrophilic copolymers (2), the above amount (part by weight) of the hydrophilic copolymers (2) means a total amount of these hydrophilic copolymers (2). The above abundance ratio (mixing ratio) is substantially equal to a ratio of a total charge amount (weight) of the hydrophilic copolymers (2) with respect to a total charge amount (weight) of the hydroxy group-containing compounds (3) during formation of the surface lubricious layer.

[Method for Manufacturing Medical Device]

A method for manufacturing the medical device according to this embodiment is not particularly limited except that the adhesive layer is formed using the hydrophilic copolymer (1), and the surface lubricious layer is formed using the hydrophilic copolymer (2) and the hydroxy group-containing compound (3), and a known method can be applied in the same manner or after appropriate modification. For example, the medical device according to this embodiment can be manufactured in the same manner as the method described in [Method for Manufacturing Medical Device] in the above <First Aspect (Embodiment Including Adhesive Layer)>.

<Use of Medical Device>

The medical device can be used in contact with a body fluid, blood, and the like. The surface thereof has a lubricating property in an aqueous liquid such as a body fluid or physiological saline, and can enhance operability and reduce damage to tissue mucosa. Specific examples include a catheter, a stent, and a guide wire to be used in blood vessels. That is, in one embodiment, the medical device is a catheter, a stent, or a guide wire. The medical device is also exemplified by the following.

(a) Catheters to be orally or nasally inserted or allowed to indwell in a digestive organ, such as stomach tube catheters, feeding catheters, and tubes for tube feeding.

(b) Catheters to be orally or nasally inserted or allowed to indwell in a respiratory tract or trachea, such as oxygen catheters, oxygen cannulas, tubes and cuffs of tracheal tubes, tubes and cuffs of tracheotomy tubes, and tracheal aspiration catheters.

(c) Catheters to be inserted or allowed to indwell in a urethra or ureter, such as urethra catheters, urinary catheters, and catheters and balloons of urethra balloon catheters.

(d) Catheters to be inserted or allowed to indwell in various lumens in living bodies, organs, and tissues, such as suction catheters, drain catheters, and rectum catheters.

(e) Catheters to be inserted or allowed to indwell in a blood vessel, such as indwelling needles, IVH catheters, thermodilution catheters, angiography catheters, vasodilation catheters, and dilators or introducers, or guide wires, stylets, and the like for the catheters.

(f) Artificial tracheae, artificial bronchi, and the like.

(g) Medical devices for extracorporeal circulation therapy (artificial lungs, artificial hearts, artificial kidneys, and the like) and circuits therefor.

EXAMPLES

Hereinafter, the medical device and manufacturing method will be specifically described with reference to Examples, but the invention is not limited to these Examples. Note that parts and % in Examples are all by weight. In the following examples, unless otherwise defined, conditions for allowing to stand at room temperature are all at 23° C. and 55% RH.

Production Example 1: Production of Hydrophilic Copolymer (A)

In 10 mL of a 2,2,2-trifluoroethanol/water (9/1 v/v) mixed solvent, 1.82 g (6.5 mmol) of [2-(methacryloyloxy)ethyl] dimethyl-(3-sulfopropyl)ammonium hydroxide (MSPB) manufactured by Sigma-Aldrich Co. LLC., 1.46 g (3.2 mmol) of a 50 wt % aqueous solution of sodium 2-acrylamide-2-methyl-1-propanesulfonate (AMPS(Na)) manufactured by Sigma-Aldrich Co. LLC., and 0.080 g (0.3 mmol) of 4-methacryloyloxybenzophenone (MBP) manufactured by MCC UNITEC Co., Ltd. were dissolved to prepare a reaction solution. Next, the reaction solution was charged into a 30 mL eggplant-shaped flask, oxygen was removed by sufficient nitrogen bubbling, 2.8 mg (0.010 mmol) of a polymerization initiator 4,4'-azobis(4-cyanovaleric acid) was added, followed by immediate sealing, and polymerization was carried out in a water bath at 75° C. for 3 hours. Next, the solution was subjected to reprecipitation in acetone, and the supernatant was removed by decantation to obtain a copolymer (A).

The composition of the obtained copolymer (A) was MSPB:AMPS(Na):MPB=65:32:3 in terms of mol %. Here, the obtained copolymer (A) corresponds to the hydrophilic copolymer contained in the adhesive layer according to the disclosure here and the hydrophilic copolymer contained in the surface lubricious layer according to the disclosure here. The weight average molecular weight (Mw) of the obtained copolymer (A) was measured by GPC, and was 180,000 in terms of polyethylene glycol.

Production Example 2: Production of Hydrophilic Copolymer (B)

In 10 mL of a 2,2,2-trifluoroethanol/water (9/1 v/v) mixed solvent, 1.82 g (6.5 mmol) of [2-(methacryloyloxy)ethyl] dimethyl-(3-sulfopropyl)ammonium hydroxide (MSPB) manufactured by Sigma-Aldrich Co. LLC., 1.46 g (3.2 mmol) of a 50 wt % aqueous solution of sodium 2-acrylamide-2-methyl-1-propanesulfonate (AMPS(Na)) manufactured by Sigma-Aldrich Co. LLC., and 0.083 g (0.3 mmol) of 2-methacryloyloxyethyl-4-azidobenzoate (MAB) were dissolved to prepare a reaction solution. Next, the reaction solution was charged into a 30 mL eggplant-shaped flask, oxygen was removed by sufficient nitrogen bubbling, 2.8 mg (0.010 mmol) of a polymerization initiator 4,4'-azobis(4-cyanovaleric acid) was added, followed by immediate sealing, and polymerization was carried out in a water bath at 75° C. for 3 hours. Next, the solution was subjected to reprecipitation in acetone, and the supernatant was removed by decantation to obtain a copolymer (B).

The composition of the obtained copolymer (B) was MSPB:AMPS (Na):MAB=65:32:3 in terms of mol %. Here, the obtained copolymer (B) corresponds to the hydrophilic copolymer contained in the adhesive layer according to the disclosure here and the hydrophilic copolymer contained in the surface lubricious layer according to the disclosure here. The weight average molecular weight (Mw) of the obtained copolymer (B) was measured by GPC, and was 180,000 in terms of polyethylene glycol.

Example 1

The copolymer (A) obtained in Production Example 1 (corresponding to the hydrophilic copolymer according to the disclosure here) and polyethylene glycol 200 (weight average molecular weight: 180 to 220, boiling point: 250° C. or higher) manufactured by Sigma-Aldrich Co. LLC. were dissolved in ethanol/water (3/7 w/w) so as to be 7 wt % and 0.7 wt % respectively, to prepare a coating liquid (1). Note that the polyethylene glycol 200 is dissolved by an amount of 0.001 g or more in 100 mL of distilled water under a condition of room temperature (23° C.). Next, a polyamide tube (having an outer diameter of 2.4 mm and a length of 70 mm) was dipped in the coating liquid (1), and was taken out at a rate of 5 mm/sec. Next, the polyamide tube was dried at room temperature for 5 minutes to remove the solvent. Next, the polyamide tube was irradiated with UV having a wavelength of 365 nm and an irradiation output of 33 mW/cm2 under conditions of an irradiation distance of 250 mm and a sample rotation rate of 3 mm/s for 15 minutes, so as to form a surface lubricious layer on the polyamide tube (polyamide tube (1)). A mixing ratio (weight ratio) of the polyethylene glycol 200 to the hydrophilic copolymer in the surface lubricious layer of the polyamide tube (1) is 1:10. As the UV irradiation device, ECE2000 (high-pressure mercury lamp) manufactured by Dymax Corporation was used. Next, the obtained sample (polyamide tube (1)) was evaluated for the lubricating property and durability (lubrication retaining property) using a friction meter (Handy Tribo Master TL201 manufactured by Trinity-Lab Inc.) shown in FIG. 5 according to the following method. Results are shown in FIG. 6.

That is, a core material 18 was inserted into the above sample (polyamide tube (1)) to prepare a sample 16. The sample 16 was laid down in a length direction and fixed in a petri dish 12, and was immersed in physiological saline 17 having a depth that the entire sample 16 was immersed in the physiological saline. The petri dish 12 was placed on a moving table 15 of the friction meter 20 shown in FIG. 5. A silicon terminal (diameter: 10 mm) 13 was brought into contact with the sample, and a load 14 of 450 g was applied on the terminal. While the moving table 15 was subjected to 10 horizontal reciprocations under a sliding distance set to 25 mm and a sliding rate set to 16.7 mm/sec, a frictional force (sliding resistance value) (gf) was measured. An average value of friction forces in forward ways was defined as a sliding resistance value for each reciprocation, and sliding resistance values during the reciprocations from the first time to the 10th time were plotted on a graph to thereby evaluate a variation in sliding resistance value during the 10 repeated slides.

When the obtained sample (polyamide tube (1)) was evaluated for the lubricating property (sliding resistance value) and the durability (lubrication retaining property) according to the following method, the sample was "A". That is, the core material 18 was inserted into the above sample (polyamide tube (1)) to prepare the sample 16. The sample 16 was laid down in the length direction and fixed in the petri dish 12, and was immersed in the physiological saline 17 having the depth that the entire sample 16 was immersed in the physiological saline. The petri dish 12 was placed on the moving table 15 of the friction meter (Handy Tribo Master TL201 manufactured by Trinity-Lab Inc.) 20 shown in FIG. 5. The silicon terminal (diameter: 10 mm) 13 was brought into contact with the sample, and the load 14 of 450 g was applied on the terminal. While the moving table 15 was subjected to 10 horizontal reciprocations under the sliding distance set to 25 mm and the sliding rate set to 16.7 mm/sec, the frictional force (gf) was measured. The average value of the friction forces in the forward ways was defined as the sliding resistance value for each reciprocation, the sliding resistance values during the reciprocations from the first time to the 10th time were measured, and the lubricating property and the durability (lubrication retaining property) were evaluated according to the following evaluation criteria on the basis of an average value of the sliding resistance values of the first time to the 10th time in Comparative Example 1. Results are shown in Table 1. The lubricating property and the durability (lubrication retaining property) in Table 1 show results when the number of samples is 2 (n=2). When both samples are A, the lubricating property and the durability (lubrication retaining property) is indicated as "A", and when one sample is A and the other sample is B, the lubricating property and the durability (lubrication retaining property) is indicated as "B to A".

(Evaluation Criteria)

A: The sliding resistance value for each reciprocation and the average value of the sliding resistance values during the reciprocations from the first time to the 10th time are less than 50% of the average value of the sliding resistance values during the reciprocations from the first time to the 10th time in Comparative Example 1.

B: The sliding resistance value for each reciprocation and the average value of the sliding resistance values during the reciprocations from the first time to the 10th time are 50% or more and less than 90% of the average value of the sliding resistance values during the reciprocations from the first time to the 10th time in Comparative Example 1.

C: The sliding resistance value for each reciprocation and the average value of the sliding resistance values during the reciprocations from the first time to the 10th time are 90% or more and 100% or less of the average value of the sliding resistance values during the reciprocations from the first time to the 10th time in Comparative Example 1.

Example 2

A sample (polyamide tube (2)) was prepared in the same manner as in Example 1 except that the UV irradiation time was changed to 3 minutes. The obtained sample (polyamide tube (2)) was evaluated for the lubricating property and the durability (lubrication retaining property) in the same manner as in Example 1. Results are shown in FIG. 6. In addition, the obtained sample (polyamide tube (2)) was evaluated for the lubricating property and the durability (lubrication retaining property) in the same manner as in Example 1. Results are shown in Table 1.

Example 3

A sample (polyamide tube (3)) was prepared in the same manner as in Example 1 except that the copolymer (A) obtained in Production Example 1 (corresponding to the hydrophilic copolymer according to the disclosure here) and glycerol (molecular weight: 92.09, boiling point: 290° C.) manufactured by Sigma-Aldrich Co. LLC. were dissolved in ethanol/water (3/7 w/w) so as to be 7 wt % and 0.7 wt % respectively, to prepare a coating liquid. Note that the glycerol used in this example is dissolved by an amount of 0.001 g or more in 100 mL of distilled water under a condition of room temperature (23° C.). A mixing ratio (weight ratio) of the glycerol to the hydrophilic copolymer in the surface lubricious layer of the polyamide tube (3) is 1:10. The obtained sample (polyamide tube (3)) was evaluated for the lubricating property and the durability (lubrication retaining property) in the same manner as in Example 1. Results are shown in FIG. 7. In addition, the obtained sample (polyamide tube (3)) was evaluated for the lubricating property and the durability (lubrication retaining property) in the same manner as in Example 1. Results are shown in Table 1.

Example 4

A sample (polyamide tube (4)) was prepared in the same manner as in Example 3 except that the UV irradiation time was changed to 3 minutes. The obtained sample (polyamide tube (4)) was evaluated for the lubricating property and the durability (lubrication retaining property) in the same manner as in Example 1. Results are shown in FIG. 7. In addition, the obtained sample (polyamide tube (4)) was evaluated for the lubricating property and the durability (lubrication retaining property) in the same manner as in Example 1. Results are shown in Table 1.

Comparative Example 1

A sample (comparative polyamide tube (1)) was prepared in the same manner as in Example 1 except that a coating liquid was prepared without blending the polyethylene glycol 200. The obtained sample (comparative polyamide tube (1)) was evaluated for the lubricating property and the durability (lubrication retaining property) in the same manner as in Example 1. Results are shown in FIGS. 6 and 7. In addition, for the obtained sample (comparative polyamide tube (1)), an average value of friction forces in forward ways was defined as a sliding resistance value for each reciprocation, and an average value of the sliding resistance values during the reciprocations from the first time to the 10th time was evaluated in the same manner as in Example 1.

According to FIG. 6, the polyamide tubes (1) and (2) according to the disclosure here have a low initial (the first reciprocation) sliding resistance value (excellent in lubricating property), and sliding resistance values thereof hardly change until the 10th reciprocation (excellent in durability (lubrication retaining property)). In contrast, the comparative polyamide tube (1) is excellent in durability (lubrication retaining property), but an initial sliding resistance value thereof is higher than that of the polyamide tube (1) according to the disclosure here. Similarly, according to FIG. 7, the polyamide tubes (3) and (4) according to the disclosure here have a low initial (the first reciprocation) sliding resistance value (excellent in lubricating property), and sliding resistance values thereof hardly change until the 10th reciprocation (excellent in durability (lubrication retaining property)). In contrast, the comparative polyamide tube (1) is excellent in durability (lubrication retaining property), but the initial sliding resistance value thereof is higher than that of the polyamide tube (1) according to the disclosure here.

This evaluation method is a method on assumption of a high load condition where a clearance between a catheter and an inner surface of a lumen in a living body is small. That is, the sliding resistance value is measured using the tube as a sample. The tube-shaped sample has a contact area with the terminal smaller than that of a sheet-shaped sample. Therefore, the tube-shaped sample has a force per unit area applied from the terminal (a larger load) larger than that of the sheet-shaped sample. Therefore, it is considered that the medical device disclosed here can exhibit excellent lubricating property and durability (lubrication retaining property) even under a high load condition where the clearance between the catheter and the inner surface of the lumen in the living body is small. Note that although the comparative polyamide tube (1) in Comparative Example 1 has a sliding resistance value at an initial stage (the first reciprocation) and up to the 10th reciprocation higher than those of the polyamide tubes (1) to (4), it is considered that the comparative polyamide tube (1) also exhibits sufficient lubricating property and durability (lubrication retaining property) under normal conditions.

Further, in FIG. 6, the polyamide tube (2), which has a UV irradiation time of 3 minutes, showed the same level of lubricating property and durability (lubrication retaining property) as those of the polyamide tube (1), which has a UV irradiation time of 15 minutes. Similarly, in FIG. 7, the polyamide tube (4), which has a UV irradiation time of 3 minutes, showed the same level of lubricating property and durability (lubrication retaining property) as those of the polyamide tube (3), which has a UV irradiation time of 15 minutes. It is considered that a hydroxy group contained in polyethylene glycol or glycerol promoted the formation of the chemical bond via the photoreactive group, and a surface lubricious layer excellent in lubricating property and durability (lubrication retaining property) was obtained even though the UV irradiation time was short.

Example 5

A sample (polyamide tube (5)) was prepared in the same manner as in Example 1 except that the copolymer (B) obtained in Production Example 2 (corresponding to the hydrophilic copolymer according to the disclosure here) and glycerol (molecular weight: 92.09, boiling point: 290° C.) manufactured by Sigma-Aldrich Co. LLC. were dissolved in ethanol/water (3/7 w/w) so as to be 10 wt % and 1 wt % respectively, to prepare a coating liquid. Note that the glycerol used in this example is dissolved by an amount of 0.001 g or more in 100 mL of distilled water under a condition of room temperature (23° C.). A mixing ratio (weight ratio) of the glycerol to the hydrophilic copolymer (2) in the surface lubricious layer of the polyamide tube (5) is 1:10. The obtained sample (polyamide tube (5)) was evaluated for the lubricating property and the durability (lubrication retaining property) in the same manner as in Example 1. Results are shown in Table 1.

Example 6

A sample (polyamide tube (6)) was prepared in the same manner as in Example 5 except that the UV irradiation time was changed to 3 minutes. The obtained sample (polyamide tube (6)) was evaluated for the lubricating property and the durability (lubrication retaining property) in the same manner as in Example 1. Results are shown in Table 1.

Example 7

A sample (polyamide tube (7)) was prepared in the same manner as in Example 1 except that the copolymer (A) obtained in Production Example 1 (corresponding to the hydrophilic copolymer according to the disclosure here) and glycerol 1,2-carbonate (molecular weight: 118.09, boiling point: 160° C.) manufactured by Tokyo Chemical Industry Co., Ltd. were dissolved in ethanol/water (3/7 w/w) so as to be 10 wt % and 0.1 wt % respectively, to prepare a coating liquid. Note that the glycerol 1,2-carbonate used in this example is dissolved by an amount of 0.001 g or more in 100 mL of distilled water under a condition of room temperature (23° C.). A mixing ratio (weight ratio) of the glycerol 1,2-carbonate to the hydrophilic copolymer in the surface lubricious layer of the polyamide tube (7) is 1:100. The obtained sample (polyamide tube (7)) was evaluated for the lubricating property and the durability (lubrication retaining property) in the same manner as in Example 1. Results are shown in Table 1.

Example 8

A sample (polyamide tube (8)) was prepared in the same manner as in Example 7 except that the UV irradiation time was changed to 3 minutes. The obtained sample (polyamide tube (8)) was evaluated for the lubricating property and the durability (lubrication retaining property) in the same manner as in Example 1. Results are shown in Table 1.

Example 9

A sample (polyamide tube (9)) was prepared in the same manner as in Example 1 except that the copolymer (A) obtained in Production Example 1 (corresponding to the hydrophilic copolymer according to the disclosure here) and diglycerol (molecular weight: 166.17, boiling point: 270° C.) manufactured by Tokyo Chemical Industry Co., Ltd. were dissolved in ethanol/water (3/7 w/w) so as to be 10 wt % and 2 wt % respectively, to prepare a coating liquid. Note that the diglycerol used in this example is dissolved by an amount of 0.001 g or more in 100 mL of distilled water under a condition of room temperature (23° C.). A mixing ratio (weight ratio) of the diglycerol to the hydrophilic copolymer in the surface lubricious layer of the polyamide tube (9) is 1:5. The obtained sample (polyamide tube (9)) was evaluated for the lubricating property and the durability (lubrication retaining property) in the same manner as in Example 1. Results are shown in Table 1.

Example 10

A sample (polyamide tube (10)) was prepared in the same manner as in Example 9 except that the UV irradiation time was changed to 3 minutes. The obtained sample (polyamide tube (10)) was evaluated for the lubricating property and the durability (lubrication retaining property) in the same manner as in Example 1. Results are shown in Table 1.

Example 11

A sample (polyamide tube (11)) was prepared in the same manner as in Example 1 except that the copolymer (A) obtained in Production Example 1 (corresponding to the hydrophilic copolymer according to the disclosure) and trehalose (molecular weight: 342.3, boiling point: 398° C.) manufactured by FUJIFILM Wako Pure Chemical Corporation were dissolved in ethanol/water (3/7 w/w) so as to be 10 wt % and 1 wt % respectively, to prepare a coating liquid. Note that the trehalose used in this example is dissolved by an amount of 0.001 g or more in 100 mL of distilled water under a condition of room temperature (23° C.). A mixing ratio (weight ratio) of the trehalose to the hydrophilic copolymer in the surface lubricious layer of the polyamide tube (11) is 1:10. The obtained sample (polyamide tube (11)) was evaluated for the lubricating property and the durability (lubrication retaining property) in the same manner as in Example 1. Results are shown in Table 1.

Example 12

A sample (polyamide tube (12)) was prepared in the same manner as in Example 11 except that the UV irradiation time was changed to 3 minutes. The obtained sample (polyamide tube (12)) was evaluated for the lubricating property and the durability (lubrication retaining property) in the same manner as in Example 1. Results are shown in Table 1.

Example 13

A sample (polyamide tube (13)) was prepared in the same manner as in Example 1 except that the copolymer (A) obtained in Production Example 1 (corresponding to the hydrophilic copolymer according to the disclosure here) and erythritol (molecular weight: 122.12, boiling point: 331° C.) manufactured by Tokyo Chemical Industry Co., Ltd. were dissolved in ethanol/water (3/7 w/w) so as to be 10 wt % and 0.5 wt % respectively, to prepare a coating liquid. Note that the erythritol used in this example is dissolved by an amount of 0.001 g or more in 100 mL of distilled water under a condition of room temperature (23° C.). A mixing ratio (weight ratio) of the erythritol to the hydrophilic copolymer in the surface lubricious layer of the polyamide tube (13) is 1:20. The obtained sample (polyamide tube (13)) was evaluated for the lubricating property and the durability (lubrication retaining property) in the same manner as in Example 1. Results are shown in Table 1.

Example 14

A sample (polyamide tube (14)) was prepared in the same manner as in Example 13 except that the UV irradiation time was changed to 3 minutes. The obtained sample (polyamide tube (14)) was evaluated for the lubricating property and the durability (lubrication retaining property) in the same manner as in Example 1. Results are shown in Table 1.

Example 15

A sample (polyamide tube (15)) was prepared in the same manner as in Example 1 except that the copolymer (A) obtained in Production Example 1 (corresponding to the hydrophilic copolymer according to the disclosure here) and tripropylene glycol (molecular weight: 192.26, boiling point: 270° C.) manufactured by FUJIFILM Wako Pure Chemical Corporation were dissolved in ethanol/water (3/7 w/w) so as to be 10 wt % and 2 wt % respectively, to prepare a coating liquid. Note that the tripropylene glycol used in this example is dissolved by an amount of 0.001 g or more in 100 mL of distilled water under a condition of room temperature (23° C.). A mixing ratio (weight ratio) of the tripropylene glycol to the hydrophilic copolymer in the surface lubricious layer of the polyamide tube (15) is 1:5. The obtained sample (polyamide tube (15)) was evaluated for the lubricating property and the durability (lubrication retaining property) in the same manner as in Example 1. Results are shown in Table 1.

Example 16

A sample (polyamide tube (16)) was prepared in the same manner as in Example 15 except that the UV irradiation time was changed to 3 minutes. The obtained sample (polyamide tube (16)) was evaluated for the lubricating property and the durability (lubrication retaining property) in the same manner as in Example 1. Results are shown in Table 1.

Example 17

A sample (polyamide tube (17)) was prepared in the same manner as in Example 1 except that the copolymer (A) obtained in Production Example 1 (corresponding to the hydrophilic copolymer according to the disclosure) and polyethylene glycol 400 (weight average molecular weight: 380 to 420, boiling point: 250° C. or higher) manufactured by Sigma-Aldrich Co. LLC. were dissolved in ethanol/water (3/7 w/w) so as to be 10 wt % and 0.5 wt % respectively, to prepare a coating liquid. Note that the polyethylene glycol 400 used in this example is dissolved by an amount of 0.001 g or more in 100 mL of distilled water under a condition of room temperature (23° C.). A mixing ratio (weight ratio) of the polyethylene glycol 400 to the hydrophilic copolymer in the surface lubricious layer of the polyamide tube (17) is 1:20. The obtained sample (polyamide tube (17)) was evaluated for the lubricating property and the durability (lubrication retaining property) in the same manner as in Example 1. Results are shown in Table 1.

Example 18

A sample (polyamide tube (18)) was prepared in the same manner as in Example 17 except that the UV irradiation time was changed to 3 minutes. The obtained sample (polyamide tube (18)) was evaluated for the lubricating property and the durability (lubrication retaining property) in the same manner as in Example 1. Results are shown in Table 1.

Example 19

A sample (polyamide tube (19)) was prepared in the same manner as in Example 1 except that the copolymer (A)

obtained in Production Example 1 (corresponding to the hydrophilic copolymer according to the disclosure) and Triton X-100 (molecular weight: 646.85, boiling point: 200° C. or higher) manufactured by Sigma-Aldrich Co. LLC. were dissolved in ethanol/water (3/7 w/w) so as to be 10 wt % and 0.4 wt % respectively, to prepare a coating liquid. Note that Triton X-100 used in this example is dissolved by an amount of 0.001 g or more in 100 mL of distilled water under a condition of room temperature (23° C.). A mixing ratio (weight ratio) of Triton X-100 to the hydrophilic copolymer in the surface lubricious layer of the polyamide tube (19) is 1:25. The obtained sample (polyamide tube (19)) was evaluated for the lubricating property and the durability (lubrication retaining property) in the same manner as in Example 1. Results are shown in Table 1.

Example 20

A sample (polyamide tube (20)) was prepared in the same manner as in Example 19 except that the UV irradiation time was changed to 3 minutes. The obtained sample (polyamide tube (20)) was evaluated for the lubricating property and the durability (lubrication retaining property) in the same manner as in Example 1. Results are shown in Table 1.

Example 21

The copolymer (A) obtained in Production Example 1 (corresponding to the hydrophilic copolymer (1) according to the disclosure) was dissolved in ethanol/water (3/7 w/w) so as to be 10 wt %, to prepare a coating liquid (21'). Next, a polyamide tube (having an outer diameter of 2.4 mm and a length of 70 mm) was dipped in the coating liquid (21'), and was taken out at a rate of 1 mm/sec. Next, the polyamide tube was dried at room temperature for 60 seconds to remove the solvent. Next, the polyamide tube was irradiated with ultraviolet rays (UV) having a wavelength of 365 nm and an irradiation output of 33 mW/cm2 under conditions of an irradiation distance of 250 mm and a sample rotation rate of 3 mm/sec for 3 minutes, so as to form an adhesive layer on the polyamide tube (polyamide tube (21')). Note that as a UV irradiation device, ECE2000 (high-pressure mercury lamp) manufactured by Dymax Corporation was used.

Next, glycerol (molecular weight: 92.09, boiling point: 290° C.) manufactured by Sigma-Aldrich Co. LLC. and the copolymer (A) obtained in Production Example 1 (corresponding to the hydrophilic copolymer (2) according to the disclosure here) were dissolved in water so as to be 0.05 wt % and 1 wt % respectively, to prepare a coating liquid (21). A mixing ratio (weight ratio) of the glycerol to the hydrophilic copolymer (1) in the coating liquid (21) is 1:20. Next, the polyamide tube (21') prepared as above was dipped in the coating liquid (21), and was taken out at a rate of 5 mm/sec. Next, the polyamide tube (21') was dried at room temperature for 5 minutes to remove the solvent. Next, the polyamide tube (21') was irradiated with ultraviolet rays (UV) having a wavelength of 365 nm and an irradiation output of 33 mW/cm2 under conditions of an irradiation distance of 250 mm and a sample rotation rate of 3 mm/sec for 15 minutes, so as to form a surface lubricious layer on the adhesive layer of the polyamide tube (21') (polyamide tube (21)). Note that as a UV irradiation device, ECE2000 (high-pressure mercury lamp) manufactured by Dymax Corporation was used. A mixing ratio (weight ratio) of the glycerol to the hydrophilic copolymer (1) in the surface lubricious layer of the polyamide tube (21) is 1:20. The obtained sample (polyamide tube (21)) was evaluated for the lubricating property and the durability (lubrication retaining property) in the same manner as in Example 1. Results are shown in Table 2.

Example 22

A sample (polyamide tube (22)) was prepared in the same manner as in Example 21 except that the UV irradiation time after dipping of the coating liquid (21) was changed to 3 minutes. The obtained sample (polyamide tube (22)) was evaluated for the lubricating property and the durability (lubrication retaining property) in the same manner as in Example 1. Results are shown in Table 2.

Example 23

The copolymer (A) obtained in Production Example 1 (corresponding to the hydrophilic copolymer (1) according to the disclosure) was dissolved in ethanol/water (3/7 w/w) so as to be 10 wt %, to prepare a coating liquid (23'). Next, a polyamide tube (having an outer diameter of 2.4 mm and a length of 70 mm) was dipped in the coating liquid (23'), and was taken out at a rate of 1 mm/sec. Next, the polyamide tube was dried at room temperature for 60 seconds to remove the solvent. Next, the polyamide tube was irradiated with ultraviolet rays (UV) having a wavelength of 365 nm and an irradiation output of 33 mW/cm2 under conditions of an irradiation distance of 250 mm and a sample rotation rate of 3 mm/sec for 3 minutes, so as to form an adhesive layer on the polyamide tube (polyamide tube (23')). Note that as a UV irradiation device, ECE2000 (high-pressure mercury lamp) manufactured by Dymax Corporation was used.

Next, glycerol (molecular weight: 92.09, boiling point: 290° C.) manufactured by Sigma-Aldrich Co. LLC. and the copolymer (B) obtained in Production Example 2 (corresponding to the hydrophilic copolymer (2) according to the disclosure here) were dissolved in water so as to be 0.01 wt % and 1 wt % respectively, to prepare a coating liquid (23). A mixing ratio (weight ratio) of the glycerol to the hydrophilic copolymer (2) in the coating liquid (23) is 1:100. Next, the polyamide tube (23') prepared as above was dipped in the coating liquid (23), and was taken out at a rate of 5 mm/sec. Next, the polyamide tube (23') was dried at room temperature for 5 minutes to remove the solvent. Next, the polyamide tube (23') was irradiated with ultraviolet rays (UV) having a wavelength of 365 nm and an irradiation output of 33 mW/cm2 under conditions of an irradiation distance of 250 mm and a sample rotation rate of 3 mm/sec for 15 minutes, so as to form a surface lubricious layer on the adhesive layer of the polyamide tube (23') (polyamide tube (23)). Note that as a UV irradiation device, ECE2000 (high-pressure mercury lamp) manufactured by Dymax Corporation was used. A mixing ratio (weight ratio) of the glycerol to the hydrophilic copolymer (2) in the surface lubricious layer of the polyamide tube (23) is 1:100. The obtained sample (polyamide tube (23)) was evaluated for the lubricating property and the durability (lubrication retaining property) in the same manner as in Example 1. Results are shown in Table 2.

Example 24

A sample (polyamide tube (24)) was prepared in the same manner as in Example 23 except that the UV irradiation time after dipping of the coating liquid (23) was changed to 3 minutes. The obtained sample (polyamide tube (24)) was evaluated for the lubricating property and the durability (lubrication retaining property) in the same manner as in Example 1. Results are shown in Table 2.

The results of Examples 1 to 20 are summarized in the following Table 1. The results of Examples 21 to 24 are summarized in the following Table 2. Note that in the following Tables 1 and 2, the mixing ratio indicates a weight ratio of hydrophilic copolymer:water-retaining material (hydroxy group-containing compounds (1), (2), and (3)) in the surface lubricious layer. For example, the mixing weight ratio in Example 1 indicates a mixing weight ratio of hydrophilic copolymer (A):polyethylene glycol 200 (PEG200). Columns for each hydrophilic copolymer and each water-retaining material indicate concentrations of the hydrophilic copolymer and the water-retaining material (hydroxy group-containing compounds (1), (2), and (3)) in the coating liquid.

TABLE 1

| | Surface lubricious layer | | | | Lubricating |
|---|---|---|---|---|---|
| | Hydrophilic copolymer (A) | PEG200 | Mixing weight ratio | UV irradiation time (min) | property and durability (lubrication retaining property) |
| Example 1 | 7 wt % | 0.7 wt % | 10:1 | 15 | A |
| Example 2 | 7 wt % | 0.7 wt % | 10:1 | 3 | A |
| | Hydrophilic copolymer (A) | Glycerol | Mixing weight ratio | UV irradiation time (min) | Lubricating property and durability (lubrication retaining property) |
| Example 3 | 7 wt % | 0.7 wt % | 10:1 | 15 | A |
| Example 4 | 7 wt % | 0.7 wt % | 10:1 | 3 | A |
| Comparative Example 1 | 7 wt % | — | — | 15 | — |
| | Hydrophilic copolymer (B) | Glycerol | Mixing weight ratio | UV irradiation time (min) | Lubricating property and durability (lubrication retaining property) |
| Example 5 | 10 wt % | 1 wt % | 10:1 | 15 | B to A |
| Example 6 | 10 wt % | 1 wt % | 10:1 | 3 | B to A |
| | Hydrophilic copolymer (A) | Glycerol 1,2-carbonate | Mixing weight ratio | UV irradiation time (min) | Lubricating property and durability (lubrication retaining property) |
| Example 7 | 10 wt % | 0.1 wt % | 100:1 | 15 | B |
| Example 8 | 10 wt % | 0.1 wt % | 100:1 | 3 | B |
| | Hydrophilic copolymer (A) | Diglycerol | Mixing weight ratio | UV irradiation time (min) | Lubricating property and durability (lubrication retaining property) |
| Example 9 | 10 wt % | 2 wt % | 5:1 | 15 | A |
| Example 10 | 10 wt % | 2 wt % | 5:1 | 3 | A |
| | Hydrophilic copolymer (A) | Trehalose | Mixing weight ratio | UV irradiation time (min) | Lubricating property and durability (lubrication retaining property) |
| Example 11 | 10 wt % | 1 wt % | 10:1 | 15 | A |
| Example 12 | 10 wt % | 1 wt % | 10:1 | 3 | A |
| | Hydrophilic copolymer (A) | Erythritol | Mixing weight ratio | UV irradiation time (min) | Lubricating property and durability (lubrication retaining property) |
| Example 13 | 10 wt % | 0.5 wt % | 20:1 | 15 | A |
| Example 14 | 10 wt % | 0.5 wt % | 20:1 | 3 | A |
| | Hydrophilic copolymer (A) | Tripropylene glycol | Mixing weight ratio | UV irradiation time (min) | Lubricating property and durability (lubrication retaining property) |
| Example 15 | 10 wt % | 2 wt % | 5:1 | 15 | A |
| Example 16 | 10 wt % | 2 wt % | 5:1 | 3 | A |

TABLE 1-continued

| | Hydrophilic copolymer (A) | PEG400 | Mixing weight ratio | UV irradiation time (min) | Lubricating property and durability (lubrication retaining property) |
|---|---|---|---|---|---|
| Example 17 | 10 wt % | 0.5 wt % | 20:1 | 15 | A |
| Example 18 | 10 wt % | 0.5 wt % | 20:1 | 3 | A |

| | Hydrophilic copolymer (A) | Triton X-100 | Mixing weight ratio | UV irradiation time (min) | Lubricating property and durability (lubrication retaining property) |
|---|---|---|---|---|---|
| Example 19 | 10 wt % | 0.4 wt % | 25:1 | 15 | B |
| Example 20 | 10 wt % | 0.4 wt % | 25:1 | 3 | B |

TABLE 2

| | Adhesive layer | Surface lubricious layer | | | | Lubricating property |
|---|---|---|---|---|---|---|
| | Hydrophilic copolymer (A) | Hydrophilic copolymer (A) | Glycerol | Mixing weight ratio | UV irradiation time (min) | and durability (lubrication retaining property) |
| Example 21 | 10 wt % | 1 wt % | 0.05 wt % | 20:1 | 15 | A |
| Example 22 | 10 wt % | 1 wt % | 0.05 wt % | 20:1 | 3 | A |

| | Hydrophilic copolymer (A) | Hydrophilic copolymer (B) | Glycerol | Mixing weight ratio | UV irradiation time (min) | Lubricating property and durability (lubrication retaining property) |
|---|---|---|---|---|---|---|
| Example 23 | 10 wt % | 1 wt % | 0.01 wt % | 100:1 | 15 | B to A |
| Example 24 | 10 wt % | 1 wt % | 0.01 wt % | 100:1 | 3 | B to A |

What is claimed is:

1. A medical device, comprising:

a substrate layer;

a surface lubricious layer formed on at least a part of the substrate layer, the surface lubricious layer containing: i) a hydrophilic copolymer that exhibits a lubricating property when in contact with an aqueous liquid, the hydrophilic copolymer containing a structural unit derived from a polymerizable monomer (A) having a sulfobetaine structure, a structural unit derived from a polymerizable monomer (B) having at least one group selected from a group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group; and ii) a hydroxy group-containing compound that retains the aqueous liquid to improve lubrication retaining properties of the medical device, the hydroxy group-containing compound being selected from a group consisting of a non-volatile alcohol, a partially esterified product thereof, and a partially etherified product thereof, and being soluble in water; and the hydrophilic copolymer being present in an amount ranging from 2 parts to 20 parts by weight with respect to 1 part by weight of the hydroxy group-containing compound.

2. The medical device according to claim 1, wherein the hydroxy group-containing compound is at least one hydroxy group-containing compound selected from a group consisting of ethylene glycol, polyethylene glycol, propylene glycol, polypropylene glycol, glycerol, diglycerol, triglycerol, dipropylene glycol, tripropylene glycol, polyvinyl alcohol, trehalose, and erythritol, and that is soluble in water.

3. The medical device according to claim 1, further comprising an adhesive layer formed on at least a part of the substrate layer, the adhesive layer being between the substrate layer and the surface lubricious layer, the adhesive layer containing a hydrophilic copolymer containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group.

4. The medical device according to claim 1, wherein the polymerizable monomer (A) is represented by the following formula (1):

[Chem. 1]

(1)

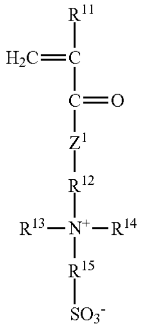

in the above formula (1),
$R^{11}$ represents a hydrogen atom or a methyl group,
$Z^1$ represents an oxygen atom or —NH—,
$R^{12}$ and $R^{15}$ each independently represent a linear or branched alkylene group having 1 to 20 carbon atoms, and
$R^{13}$ and $R^{14}$ each independently represent a linear or branched alkyl group having 1 to 20 carbon atoms.

5. The medical device according to claim 1, wherein the polymerizable monomer (B) is represented by the following formula (2), (3), or (4):

[Chem. 2]

(2)

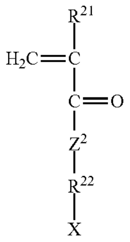

in the above formula (2),
$R^{21}$ represents a hydrogen atom or a methyl group,
$Z^2$ represents an oxygen atom or —NH—,
$R^{22}$ represents a linear or branched alkylene group having 1 to 20 carbon atoms, and
X represents a group selected from the group consisting of a sulfonic acid group ($—SO_3H$), a sulfuric acid group ($—OSO_3H$), a sulfurous acid group ($—OSO_2H$), and salt groups thereof,

[Chem. 3]

(3)

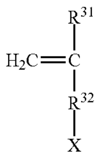

in the above formula (3),
$R^{31}$ represents a hydrogen atom or a methyl group,
$R^{32}$ represents a single bond or a linear or branched alkylene group having 1 to 20 carbon atoms, and
X represents a group selected from the group consisting of a sulfonic acid group ($—SO_3H$), a sulfuric acid group ($—OSO_3H$), a sulfurous acid group ($—OSO_2H$), and salt groups thereof,

[Chem. 4]

(4)

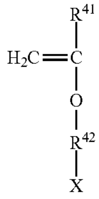

in the above formula (4),
$R^{41}$ represents a hydrogen atom or a methyl group,
$R^{42}$ represents a linear or branched alkylene group having 1 to 20 carbon atoms, and
X represents a group selected from the group consisting of a sulfonic acid group ($—SO_3H$), a sulfuric acid group ($—OSO_3H$), a sulfurous acid group ($—OSO_2H$), and salt groups thereof.

6. The medical device according to claim 1, wherein the polymerizable monomer (C) has a group having a benzophenone structure.

7. A medical device, comprising:
a substrate layer; and
a surface lubricious layer formed on at least a part of the substrate layer, the surface lubricious layer containing: i) a hydrophilic copolymer that exhibits a lubricating property when in contact with an aqueous liquid, the hydrophilic copolymer containing a structural unit derived from a polymerizable monomer (A) having a sulfobetaine structure, a structural unit derived from a polymerizable monomer (B) having at least one group selected from a group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group; and ii) a hydroxy group-containing compound that retains the aqueous liquid to improve lubrication retaining properties of the medical device, the hydroxy group-containing compound being represented by the following formula and being soluble in water,
the hydrophilic copolymer being present in an amount ranging from 2 parts to 20 parts by weight with respect to 1 part by weight of the hydroxy group-containing compound, $$X—O\text{-}(\text{-}A\text{-}O\text{-})_n\text{-}Y$$ [Chem. 5]

in the above formula,
X represents a hydrogen atom or a substituted or unsubstituted monovalent hydrocarbon group having 1 to 22 carbon atoms,
A represents a group represented by $—CH_2—$, $—(CH_2)_2—$, $—(CH_2)_3—$, or $—CH_2—CH(CH_3)—$,
n represents a number of 1 or more,
Y represents a hydrogen atom or an acyl group, and when Y represents an acyl group, X represents a hydrogen atom or a monovalent hydrocarbon group having 1 to 7 carbon atoms substituted with a hydroxy group.

8. The medical device according to claim 7, wherein the hydroxy group-containing compound is at least one hydroxy group-containing compound selected from a group consisting of ethylene glycol, propylene glycol, diethylene glycol, dipropylene glycol, triethylene glycol, tripropylene glycol, polyethylene glycol, polypropylene glycol, and a polyoxyethylene monoalkyl phenyl ether, and that is soluble in water.

9. The medical device according to claim 7, further comprising an adhesive layer formed on at least a part of the substrate layer, the adhesive layer being between the substrate layer and the surface lubricious layer, the adhesive layer containing a hydrophilic copolymer containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group.

10. The medical device according to claim 7, wherein the polymerizable monomer (A) is represented by the following formula (1):

[Chem. 6]

(1)

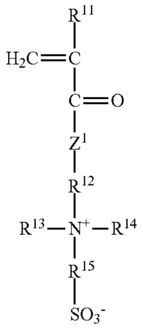

in the above formula (1), $R^{11}$ represents a hydrogen atom or a methyl group, $Z^1$ represents an oxygen atom or —NH—, $R^{12}$ and $R^{15}$ each independently represent a linear or branched alkylene group having 1 to 20 carbon atoms, and $R^{13}$ and $R^{14}$ each independently represent a linear or branched alkyl group having 1 to 20 carbon atoms.

11. The medical device according to claim 7, wherein the polymerizable monomer (B) is represented by the following formula (2), (3), or (4):

[Chem. 7]

(2)

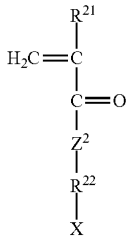

in the above formula (2), $R^{21}$ represents a hydrogen atom or a methyl group, $Z^2$ represents an oxygen atom or —NH—, $R^{22}$ represents a linear or branched alkylene group having 1 to 20 carbon atoms, and X represents a group selected from the group consisting of a sulfonic acid group (—$SO_3H$), a sulfuric acid group (—$OSO_3H$), a sulfurous acid group (—$OSO_2H$), and salt groups thereof,

[Chem. 8]

(3)

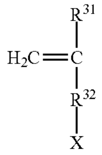

in the above formula (3), $R^{31}$ represents a hydrogen atom or a methyl group, $R^{32}$ represents a single bond or a linear or branched alkylene group having 1 to 20 carbon atoms, and X represents a group selected from the group consisting of a sulfonic acid group (—$SO_3H$), a sulfuric acid group (—$OSO_3H$), a sulfurous acid group (—$OSO_2H$), and salt groups thereof,

[Chem. 9]

(4)

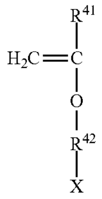

in the above formula (4), $R^{41}$ represents a hydrogen atom or a methyl group, $R^{42}$ represents a linear or branched alkylene group having 1 to 20 carbon atoms, and X represents a group selected from the group consisting of a sulfonic acid group (—$SO_3H$), a sulfuric acid group (—$OSO_3H$), a sulfurous acid group (—$OSO_2H$), and salt groups thereof.

12. The medical device according to claim 7, wherein the polymerizable monomer (C) has a group having a benzophenone structure.

13. A medical device, comprising:

a substrate layer; and a surface lubricious layer formed on at least a part of the substrate layer, the surface lubricious layer containing:

i) a hydrophilic copolymer that exhibits a lubricating property when in contact with an aqueous liquid, the hydrophilic copolymer containing a structural unit derived from a polymerizable monomer (A) having a sulfobetaine structure, a structural unit derived from a polymerizable monomer (B) having at least one group selected from a group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group; and ii) a hydroxy group-containing compound that retains the aqueous liquid to improve lubrication retaining properties of the medical device, the hydroxy group-containing compound being selected from a group consisting of glycerol, a glycerol condensate, partially esterified products thereof, and partially etherified products thereof, and being soluble in water, the hydrophilic copolymer being present in an amount ranging from 2 parts to 20 parts by weight with respect to 1 part by weight of the hydroxy group-containing compound.

14. The medical device according to claim 13, wherein the hydroxy group-containing compound is at least one hydroxy group-containing compound selected from a group consisting of glycerol, diglycerol, triglycerol, and polyglycerin, and that is soluble in water.

15. The medical device according to claim 13, further comprising an adhesive layer formed on at least a part of the substrate layer, the adhesive layer being between the substrate layer and the surface lubricious layer, the adhesive layer containing a hydrophilic copolymer containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group is formed on at least a part of the substrate layer and between the substrate layer and the surface lubricious layer.

16. The medical device according to claim 13, wherein the polymerizable monomer (A) is represented by the following formula (1):

[Chem. 10]

(1)

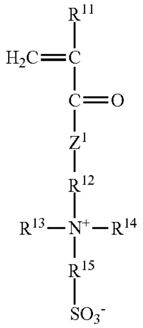

in the above formula (1), $R^{11}$ represents a hydrogen atom or a methyl group, $Z^1$ represents an oxygen atom or —NH—, $R^{12}$ and $R^{15}$ each independently represent a linear or branched alkylene group having 1 to 20 carbon atoms, and $R^{13}$ and $R^{14}$ each independently represent a linear or branched alkyl group having 1 to 20 carbon atoms.

17. The medical device according to claim 13, wherein the polymerizable monomer (B) is represented by the following formula (2), (3), or (4):

[Chem. 11]

(2)

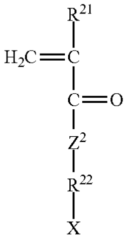

in the above formula (2), $R^{21}$ represents a hydrogen atom or a methyl group, $Z^2$ represents an oxygen atom or —NH—, $R^{22}$ represents a linear or branched alkylene group having 1 to 20 carbon atoms, and X represents a group selected from the group consisting of a sulfonic acid group (—$SO_3H$), a sulfuric acid group (—$OSO_3H$), a sulfurous acid group (—$OSO_2H$), and salt groups thereof,

[Chem. 12]

(3)

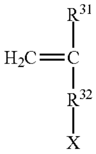

in the above formula (3), $R^{31}$ represents a hydrogen atom or a methyl group, $R^{32}$ represents a single bond or a linear or branched alkylene group having 1 to 20 carbon atoms, and X represents a group selected from the group consisting of a sulfonic acid group (—$SO_3H$), a sulfuric acid group (—$OSO_3H$), a sulfurous acid group (—$OSO_2H$), and salt groups thereof,

[Chem. 13]

(4)

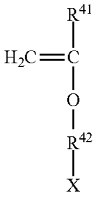

in the above formula (4), $R^{41}$ represents a hydrogen atom or a methyl group, $R^{42}$ represents a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof.

18. The medical device according to claim 13, wherein the polymerizable monomer (C) has a group having a benzophenone structure.

19. The medical device according to claim 13, wherein the medical device is a catheter, a stent, or a guide wire.

20. A method for manufacturing the medical device according to claim 13, the method comprising:

coating a coating liquid containing the hydroxy group-containing compound and the hydrophilic copolymer onto the substrate layer to form a surface lubricious layer.

21. The medical device according to claim 1, wherein the medical device, when subjected to ten horizontal reciprocations under a sliding distance of 25 mm and a sliding rate of 16.7 mm/sec, has an average sliding resistance value that is less than 50% of an average sliding resistance value of a comparative medical device prepared without a hydroxy group-containing compound.

* * * * *